US008686865B2

(12) United States Patent
Hyde et al.

(10) Patent No.: US 8,686,865 B2
(45) Date of Patent: Apr. 1, 2014

(54) INTERACTIVE TECHNIQUE TO REDUCE IRRADIATION FROM EXTERNAL SOURCE

(75) Inventors: Roderick A. Hyde, Redmond, WA (US); Muriel Y. Ishikawa, Livermore, CA (US); Jordin T. Kare, Seattle, WA (US); Clarence T. Tegreene, Bellevue, WA (US); Thomas A. Weaver, San Mateo, CA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 817 days.

(21) Appl. No.: 12/925,254

(22) Filed: Oct. 15, 2010

(65) Prior Publication Data

US 2011/0309941 A1 Dec. 22, 2011

Related U.S. Application Data

(63) Continuation-in-part of application No. 12/803,143, filed on Jun. 18, 2010, now Pat. No. 8,463,288, and a continuation-in-part of application No. 12/803,142, filed on Jun. 18, 2010, now Pat. No. 8,462,002.

(51) Int. Cl.
*G08B 17/12* (2006.01)

(52) U.S. Cl.
USPC .......................................................... 340/600

(58) Field of Classification Search
USPC ......... 340/600, 545.3, 552, 567; 702/19, 127; 343/841
See application file for complete search history.

(56) References Cited

U.S. PATENT DOCUMENTS

| | | |
|---|---|---|
| 3,764,819 A | 10/1973 | Muller |
| 5,440,290 A | 8/1995 | McCullough et al. |
| 5,459,405 A | 10/1995 | Wolff et al. |
| 5,532,681 A | 7/1996 | Peters et al. |
| 5,729,604 A | 3/1998 | Van Schyndel |
| 5,802,445 A | 9/1998 | Wiedeman et al. |
| 5,805,067 A | 9/1998 | Bradley et al. |
| 5,877,630 A | 3/1999 | Kraz |
| 5,905,262 A | 5/1999 | Spanswick |
| 5,956,626 A | 9/1999 | Kaschke et al. |
| 6,134,423 A | 10/2000 | Wiedeman et al. |
| 6,272,325 B1 | 8/2001 | Wiedeman et al. |
| 6,456,856 B1 | 9/2002 | Werling et al. |
| 6,492,957 B2 | 12/2002 | Carillo, Jr. et al. |

(Continued)

FOREIGN PATENT DOCUMENTS

| | | |
|---|---|---|
| WO | WO 95/03549 | 2/1995 |
| WO | WO 2007/023264 A1 | 3/2007 |

OTHER PUBLICATIONS

PCT International Search Report; International App. No. PCT/US 11/01086; Oct. 13, 2011; 2 pages.

(Continued)

*Primary Examiner* — Phung Nguyen

(57) ABSTRACT

Exemplary methods, systems and components enable detection and/or monitoring and/or control of electromagnetic radiation (EMR) exposure of target body-related portions of a user operating a telecommunication device. In some embodiments a risk-assessment output is provided based on a safety threshold or predetermined intrusion level of EMR exposure. A further aspect may include interaction with external EMR sources regarding possible modification of emissions as well as possible arrangements for other types of remedial action.

58 Claims, 44 Drawing Sheets

(56) References Cited

U.S. PATENT DOCUMENTS

| | | | |
|---|---|---|---|
| 6,603,981 | B1 | 8/2003 | Carillo, Jr. et al. |
| 6,650,896 | B1 | 11/2003 | Haymes et al. |
| 6,674,491 | B2 | 1/2004 | Tsou |
| 6,693,536 | B2 * | 2/2004 | Bauer, Jr. et al. ............. 340/561 |
| 6,871,139 | B2 | 3/2005 | Liu et al. |
| 6,919,845 | B2 | 7/2005 | Ozaki et al. |
| 6,934,515 | B2 | 8/2005 | Wallach |
| 6,947,764 | B2 | 9/2005 | Carillo, Jr. et al. |
| 7,035,609 | B1 | 4/2006 | Fry |
| 7,053,629 | B2 | 5/2006 | Nevermann |
| 7,084,819 | B2 | 8/2006 | De La Torre Barreiro et al. |
| 7,088,999 | B2 | 8/2006 | Shih et al. |
| 7,113,811 | B2 | 9/2006 | Goris et al. |
| 7,117,024 | B1 | 10/2006 | Dorfman |
| 7,146,139 | B2 | 12/2006 | Nevermann |
| 7,248,995 | B2 | 7/2007 | Itsuji et al. |
| 7,319,889 | B2 | 1/2008 | Goris et al. |
| 7,417,580 | B2 | 8/2008 | Abe et al. |
| 7,467,049 | B2 | 12/2008 | Hayes et al. |
| 7,495,224 | B2 | 2/2009 | Widener et al. |
| 7,522,065 | B2 | 4/2009 | Falcon |
| 7,557,353 | B2 | 7/2009 | Black et al. |
| 7,610,027 | B2 | 10/2009 | Alapuranen |
| 8,090,445 | B2 * | 1/2012 | Ginggen ......................... 607/27 |
| 2002/0016155 | A1 | 2/2002 | Charbonnier |
| 2002/0075189 | A1 | 6/2002 | Carillo, Jr. et al. |
| 2002/0118118 | A1 | 8/2002 | Myllymaki et al. |
| 2003/0064761 | A1 | 4/2003 | Nevermann |
| 2003/0080277 | A1 | 5/2003 | Bauer, Jr. et al. |
| 2004/0039684 | A1 | 2/2004 | Sandor |
| 2004/0121795 | A1 | 6/2004 | Shih et al. |
| 2005/0103978 | A1 | 5/2005 | Yang et al. |
| 2005/0153754 | A1 | 7/2005 | Shanks et al. |
| 2005/0246088 | A1 | 11/2005 | Doherty et al. |
| 2005/0288038 | A1 | 12/2005 | Kim |
| 2006/0093161 | A1 | 5/2006 | Falcon |
| 2006/0139034 | A1 * | 6/2006 | Nevermann ................... 324/644 |
| 2006/0151709 | A1 | 7/2006 | Hahl |
| 2006/0227340 | A1 | 10/2006 | Shioda et al. |
| 2007/0038402 | A1 | 2/2007 | Zhang |
| 2007/0096933 | A1 | 5/2007 | Enitan et al. |
| 2007/0106775 | A1 | 5/2007 | Wong |
| 2007/0185553 | A1 | 8/2007 | Kennedy |
| 2007/0241863 | A1 | 10/2007 | Udagawa et al. |
| 2007/0276270 | A1 | 11/2007 | Tran |
| 2008/0014872 | A1 | 1/2008 | Tucek et al. |
| 2008/0046286 | A1 | 2/2008 | Halsted |
| 2008/0072439 | A1 | 3/2008 | Steffen et al. |
| 2008/0103834 | A1 | 5/2008 | Reiner |
| 2008/0150699 | A1 | 6/2008 | Ohara et al. |
| 2008/0158172 | A1 | 7/2008 | Hotelling et al. |
| 2008/0224917 | A1 | 9/2008 | Kim et al. |
| 2008/0262714 | A1 | 10/2008 | Abramovich Ettinger |
| 2008/0292192 | A1 | 11/2008 | Seki |
| 2008/0311967 | A1 | 12/2008 | Ronen et al. |
| 2009/0012745 | A1 | 1/2009 | Longman et al. |
| 2009/0135003 | A1 | 5/2009 | Charlier et al. |
| 2009/0138244 | A1 | 5/2009 | Schuler et al. |
| 2009/0254971 | A1 | 10/2009 | Herz et al. |
| 2009/0262078 | A1 | 10/2009 | Pizzi |
| 2009/0272192 | A1 | 11/2009 | Killion et al. |
| 2010/0046766 | A1 | 2/2010 | Gregg et al. |
| 2012/0010836 | A1 | 1/2012 | Shemesh et al. |

OTHER PUBLICATIONS

PCT International Search Report; International App. No. PCT/US2011/001085; Oct. 21, 2011; pp. 1-2.

"10 Tips: Cell Phones & Limiting Radiation Exposure"; bearing a date of Jul. 23, 2008; 2 pages; MMIX, CBS Broadcasting Inc.

"BreezeNET PRO.11 Series Reference Guide"; bearing a date of Jul. 1998; 59 pages; BreezeCOM Ltd.

"Cell Phone & Tower RF Radiation Meter"; Natural Energy Works; printed Sep. 2009; pp. 1-8; Natural Energy Works.

"Cell Phone Radiation Science Review on Cancer Risks and Children's Health"; Environmental Working Group; bearing a date of Sep. 2009; pp. 1-42; Environmental Working Group; located at www.ewg.org/cellphoneradiation/fullreport.

"Choosing a Low Radiation Cell Phone"; PhysOrg.com; bearing a date of Sep. 10, 2009; pp. 1-2; located at http://www.physorg.com/print171788291.html.

"FDA Unveils Initiative to Reduce Unnecessary Radiation Exposure from Medical Imaging"; FDA News Release; bearing date of Feb. 9, 2010; pp. 1-2; FDA U.S. Food and Drug Administration; located at http://www.fda.gov/NewsEvents/Newsroom/PressAnnouncements/ucm200085.htm.

Grove, Bob; "Zap Checker 270"; MT Review; bearing a date of Jun. 2005; pp. 68-69; Monitoring Times.

Haas, Jane Glenn; "Our Health: Breast cancer linked to cell phones?"; The Orange County Register; bearing a date of Apr. 7, 2010; pp. 1-2; Deseret News Publishing Company; located at http://www.deseretnews.com/article/print/700022713/Our-Health-Bre . . . .

"Microalert 2 Radio/Microwave Alarm"; Natural Energy Works; printed on Sep. 9, 2009; pp. 1-5; located at http://www.orgonelab.org/cart/ymicroalert.htm.

"Radiation Protection from electromagnetic fields emitted by cell phones, computer monitors, and other common sources of EMF"; EMF Safety Products; printed on Jun. 18, 2010; pp. 1-6; Less EMF, Inc.; located at http://www.howweheal.com/emf.htm.

Smith, Chris Silver; "Cell Phone Triangulation Accuracy Is All Over the Map"; bearing a date of Sep. 22, 2008; pp. 1-5; Search Engine Land.

Strock, Jud; "Evaluating Cell-Phone Safety"; EE-Evaluation Engineering; printed on Aug. 6, 2009; pp. 1-5; Nelson Publishing Inc.; located at http://archive.evaluation engineering.com/archive/articles/0501deal.htm.

"Trifield Broadband Electromagnetic Field / Electrosmog Meter"; Natural Energy Works; printed on Sep. 9, 2009; pp. 1-4; located at http://www.orgonelab.org/cart/ytrifield.htm.

"Understanding the Effect of the Human Body on RF Signal Propagation"; Effect of RF on Human Body—An On-Line Tutorial; printed on Nov. 5, 2009; 1 page; located at http://www.connect802.com/human_body_rf.htm.

Walsh, Bryan; "Spotlight a Study on Cell Phones and Cancer"; Time; bearing a date of May 31, 2010; p. 15.

"Zap Checker"; bearing a date of 2005; pp. 1-8; Alan Broadband Company.

Zeiler, David; "San Francisco Approves Cellphone Radiation Law"; PC World; bearing a date of Jun. 16, 2010; pp. 1-2.

Cleveland, Robert F. Jr. et al.; "Questions and Answers about Biological Effects and Potential Hazards of Radiofrequency Electromagnetic Fields"; OET Bulletin 56 Fourth Edition; bearing a date of Aug. 1999; 38 pages (including cover pages); Federal Communications Commission, Office of Engineering & Technology.

Classic, Kelly; "Radiofrequency (RF) Radiation"; bearing a date of Dec. 18, 2009; pp. 1-6; located at www.hps.org/hbspublications/articles/rfradiation.html (cached version).

"Consumer Information About Radio Frequency Emissions and Responsible Driving"; Verizon Wireless; bearing a date of 2010; 2 pages; © 2010 Verizon.

"Do cell phones cause behavioral problems?"; bearing a date of Dec. 7, 2010; 1 page; located at http://pagingtdrgupta.blogs.cnn.com/2010/12/07/do-cell-phones-cause-behavioral-problems/.

U.S. Appl. No. 12/803,142, Hyde et al.
U.S. Appl. No. 12/803,143, Hyde et al.
U.S. Appl. No. 12/925,938, Hyde et al.
U.S. Appl. No. 12/928,939, Hyde et al.

Greene, Kate; "Hyperlinking Reality via Phones"; Technology Review; bearing a date of Nov. 20, 2006; pp. 1-4; MIT.

Jonietz, Erika; "TR10: Augmented Reality"; Technology Review; bearing a date of Mar. 12, 2007; pp. 1-3; MIT.

Livescience Staff; "Cell Phone Radiation Might Improve Memory"; University of South Florida; bearing a date of Jan. 6, 2010; pp. 1-3.

"Microsoft Demos Augmented Vision"; Technology Review; bearing a date of Mar. 3, 2009; 2 pages; located at http://www.technologyreview.com/computing/22218/?a—f.

(56) References Cited

OTHER PUBLICATIONS

Nigam, Anil; "Electromagnetic Radiation (EMR) and Its Effects"; bearing a date of Oct. 18, 2006; pp. 1-4; located at http.ezinearticles.com/?electromagnetic-radiation-(EMR)-and-its-effects.

Osterhout, Jacob E.; "Exposure to radiation from cell phones could help protect against Alzheimer's memory loss: study"; Daily News; bearing a date of Jan. 7, 2010; 1 page.

"Radiology benefit management programs can protect from radiation patients exposure"; bearing a date of Apr. 1, 2010; 1 page; located at http://www.news-medical.net/news/20100401/Radiology-benefit-management-programs-can-protect-patients-from-radiation-exposure.aspx.

Scherer, Michael; "Cell-Phone Safety: What the FCC Didn't Test"; Time; bearing a date of Oct. 26, 2010; 3 pages; Time Inc.; located at http://www.time.com/time/printout/0,8816,2027523,00.html.

PCT International Search Report; International App. No. PCT/US2011/001082; Sep. 29, 2011; 13 pages.

* cited by examiner

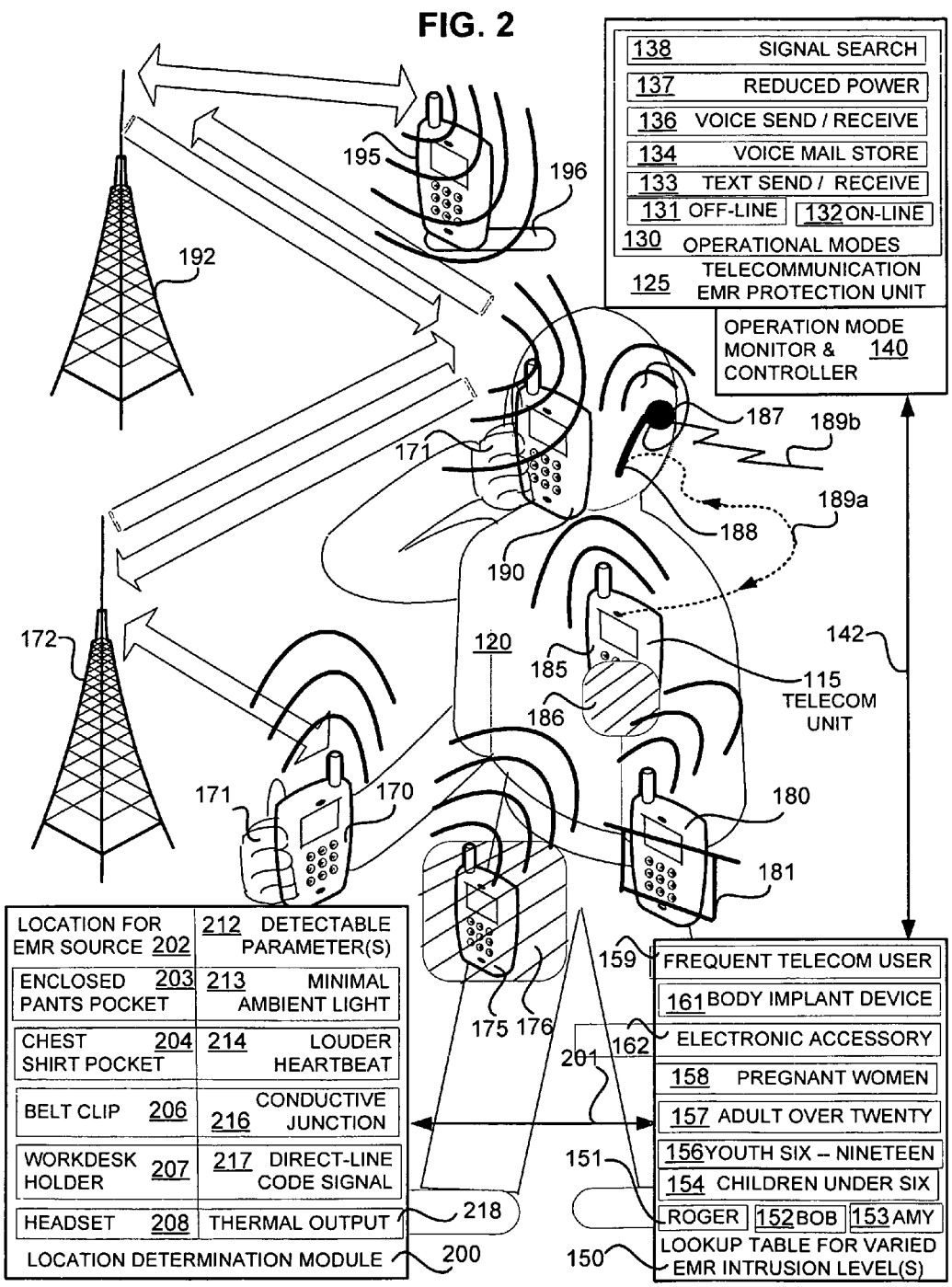

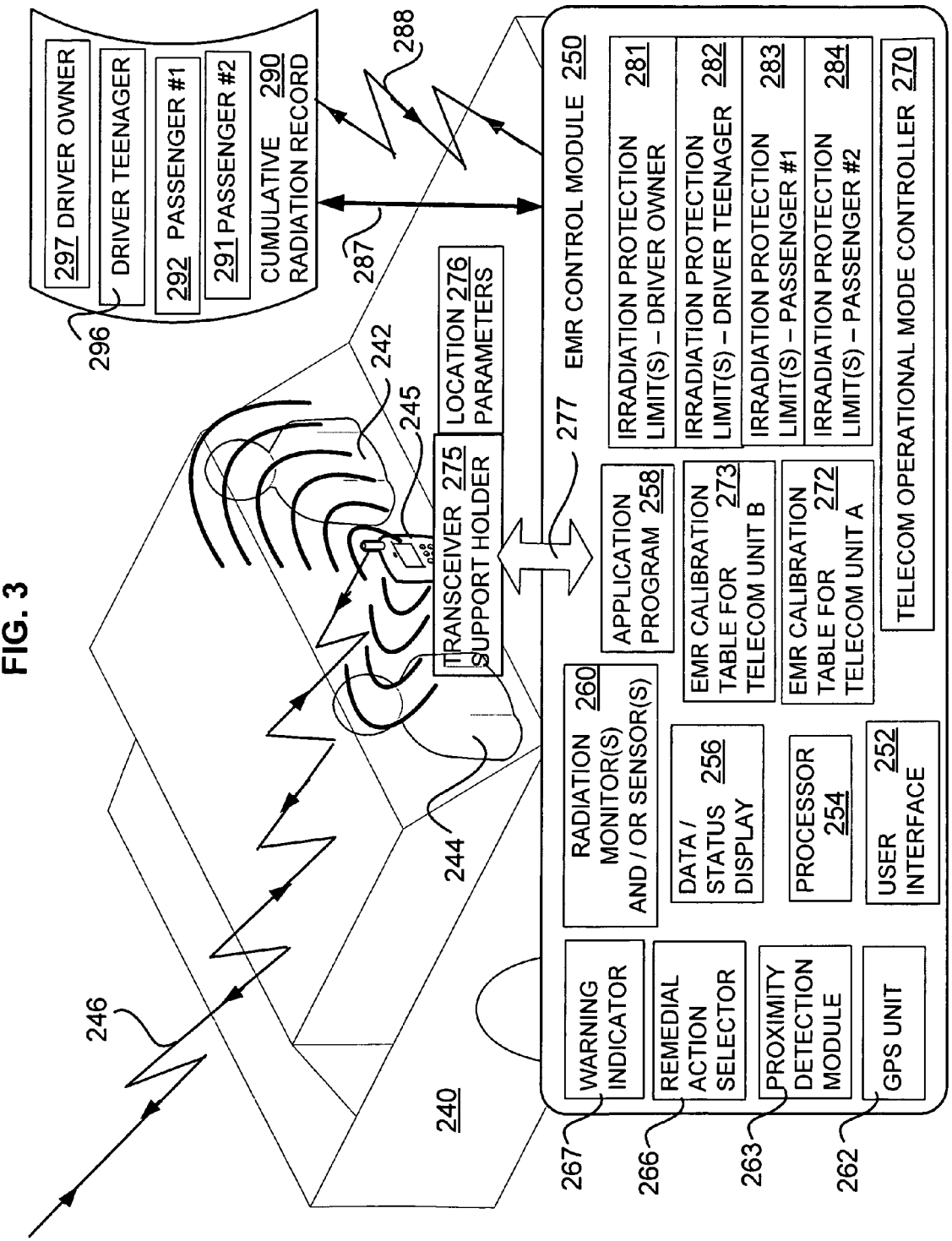

FIG. 4

IRRADIATION EXPOSURE PRIORITY TABLE 365

| User-Related Target Region 370 | User Telecom Device(s) 375 | Real-Time Exposure Threshold Limit 380 | Cumulative Exposure Threshold Limit 385 | Responsive Action 390 |
|---|---|---|---|---|
| Any Body Surface 371 | Mobile Unit CC (fixed location) with Onboard Radiation Sensor 376 | User-Choice SAR 1.6 - 4.0 watts/kg 381 | 386 | Modify Unit Power Mode 391 |
| Heart Appliance 372 (e.g., pacemaker) | Cell Phone DD (variable location) with Offboard Chest Sensor 377 | Per Device Safety Spec 382 | 387 | Turn Off Cell Phone 392 |
| Head, Eyes and / or Ears 373 | Portable Landline phone EE (fixed & variable location) with Proximity Module 378 | SAR 1.6 watts/kg 383 | 388 | Activate Warning Alarm 393 |

RADIATION EMISSION PRIORITY TABLE 310

| Telecom Device Model 320 | User IDs 325 | Operation Mode 330 | Radiation Emissions Range Cap 335 | Actual Radiation Value 340 | User Intrusion Level 345 | Target Region 350 | Real-Time Radiation Limit 355 | Cumulative Radiation Limit 360 |
|---|---|---|---|---|---|---|---|---|
| Mobile BB 323 | Bob Age 65 328 | Searching 334 | #xx microwatts/cm2 339 | 344 | 347 | Heart/Lungs | 358 | 363 |
| | | Transmit/Receive 333 | #yy microwatts/cm2 338 | 343 | | Hearing Aid 353 | 357 | 362 |
| Cell Phone AA 321 | Amy Pregnant 326 | Searching 331 | #qq microwatts/cm2 337 | 342 | 346 | Torso & Reproductive Organs 351 | 356 | 361 |
| | | Transmit/Receive 332 | #zz microwatts/cm2 336 | 341 | | | | |

DATA TABLES FOR VARIED EMISSION & EXPOSURE VALUES

801: provide a method of facilitating irradiation protection for a specified target body region 802: identifying the specified target body region of a user that is proximate to a particular communication device capable of generating electromagnetic emissions that subject the specified target body region to irradiation exposure 803: establishing whether such irradiation exposure does exceed or is predicted to exceed a safety threshold correlated with the specified target body region 804: if such irradiation exposure has a dosage value above the safety threshold, providing a responsive output based on a possible risk relative to such irradiation exposure 806: enabling a user to choose the safety threshold correlated with the specified target body region 808: enabling a user to choose the specified target body region correlated with the safety threshold 807: establishing an automatic or programmed safety threshold that is correlated with the specified target body region 812: sending the responsive output to a third party for monitoring, and / or record keeping, and / or decision making regarding possible remedial action 814: sending the responsive output to the particular communication device, wherein the particular device suggests to the user a time limit for a call and / or a change in body location relative to the particular communication device and / or a change in orientation of the particular communication device 813: sending the responsive output to one or more of the following types of third party: parent, family member, friend, insurance entity, physician, nurse, health care entity 811: sending the responsive output to a base station or cell tower or service provider or network node or other off-device destination

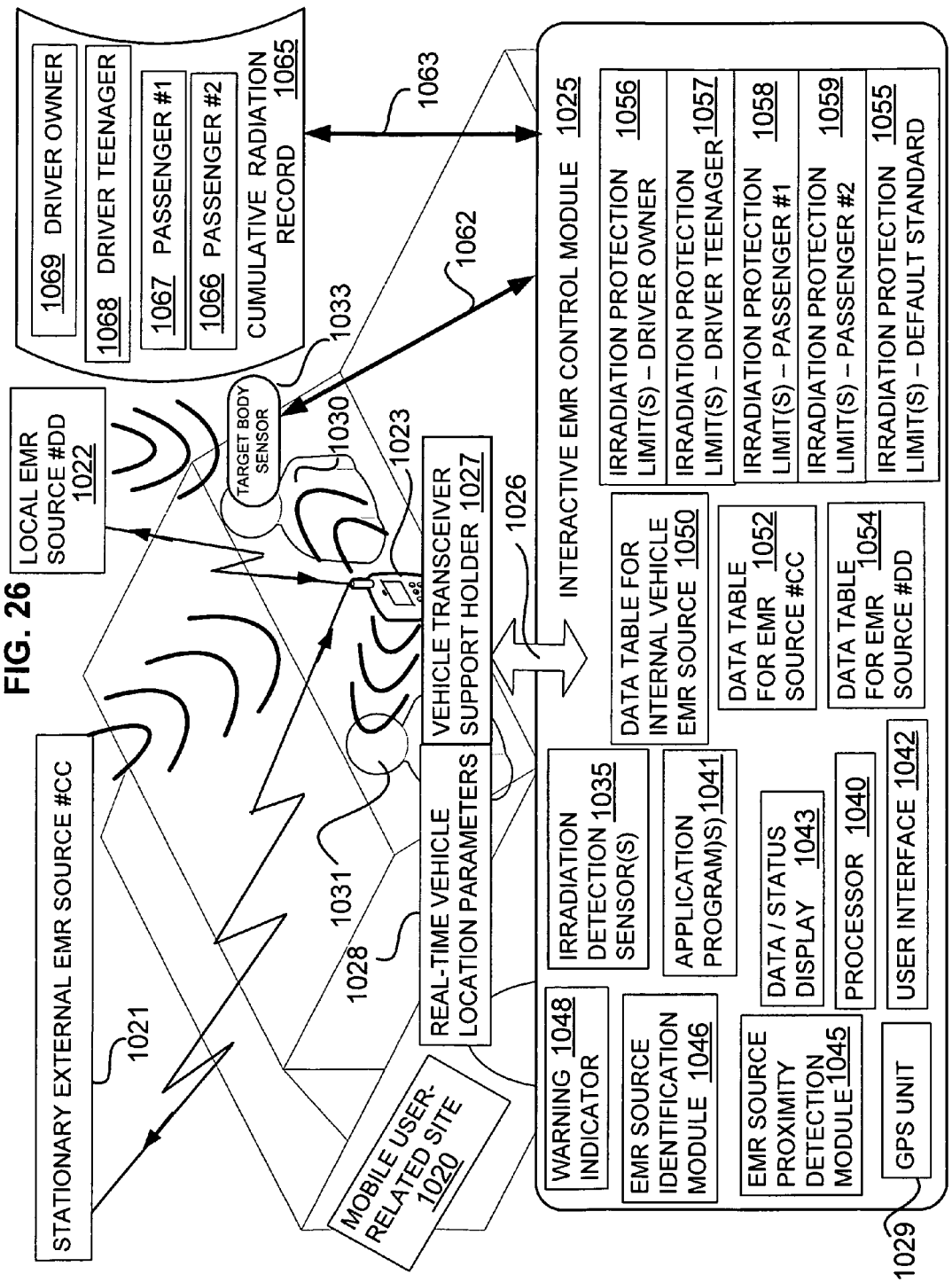

FIG. 27

| EMR SOURCE IDENTITY 1080 | EMR SOURCE LOCALE 1081 | CONTACT ADDRESS 1082 | TYPE OF DEVICE 1083 | RADIATION RISK 1084 | TIME VARIATION 1086 | REQUESTED REMEDIAL ACTION 1087 | POSSIBLE RECIPROCATION TERMS 1088 |
|---|---|---|---|---|---|---|---|
| ENTRY SECURITY SCANNER 1090 | FEDERAL OFFICE BUILDING 1091 | SCAN #123@ct.com 1092 | X-RAY & METAL DETECTOR 1093 | LOW LEVEL 1094 | WEEKDAYS 9AM-6PM 1095 | BYPASS SCANNER PER KEYCARD 1096 | FEES ASSESSED TO LAW FIRM ATTYS & STAFF 1097 |
| CLINICAL TREATMENT APPARATUS 1099 | COLLEGE MEDICAL CENTER 1101 | SAFETY @ umd.edu 1102 | RADIATION THERAPY UNITS 1103 | HIGH LEVEL 1104 | RANDOM 1105 | TEMPORARY DORMANT MODE 1106 | BECOME HEALTH PLAN MEMBER 1107 |
| HI-VOLUME COMPUTER SYSTEM 1109 | CENTRAL DATA CENTER 1111 | DEPT WEB PAGE 1112 | SATELLITE MICROWAVE UNITS 1113 | VARIABLE LEVELS 1114 | MEGA PROJECT USAGE 1115 | REMOTE TEMP OFFICE USAGE 1116 | PAY EXTRA HEALTH PLAN FEE 1117 |
| CELLPHONE BASE STATION 1118 | NEARBY TOWER 1119 | 1-888-445-5444 1120 | HIGH POWER ANTENNA 1121 | VARIABLE LEVELS 1122 | PEAK DAYTIME HOURS 1123 | NO EMR CHANGE REQUIRED 1124 | RECEIVE DISCOUNT CELLPHONE SERVICE 1125 |
| NEARBY ACTIVATED PHONES 1126 | WI-FI HOTSPOT AREA 1127 | WI-FI WEBPAGE 1128 | WI-FI RELAY UNIT 1129 | VARIABLE LEVELS 1130 | RANDOM 1131 | ACCESS TO LOW EMR WI-FI ROOM 1132 | PAYMENT OF TIME-BASED USER FEE 1133 |
| UNKNOWN EMR SOURCES 1134 | MEDICAL WAITING ROOMS 1135 | HOSPITAL HOT LINE 1-800-## 1136 | MULTIPLE TREATMENT DEVICES 1137 | UNKNOWN 1138 | ALL HOURS 24/7 1139 | NO EMR CHANGE REQUIRED 1140 | REIMBURSEMENT OF PARKING FEES 1141 |

DATA TABLE OF VARIOUS EMR SOURCES

FIG. 28

| 1145 EMR SOURCE TYPE | 1146 APPROXIMATE SEPARATION DISTANCE | 1147 IDENTIFIED LOCATION | 1148 EMISSION LEVEL | 1149 MOVING OR NON-MOVING SOURCE | 1150 REAL-TIME ACTION STATUS | 1151 REMEDIAL ACTION TERMS | 1152 CUMULATIVE RISK STATUS |
|---|---|---|---|---|---|---|---|
| KNOWN SOURCE #FF 1153 | LESS THAN TWO FEET 1154 | NORTHWEST DIRECTION 1155 | SPORADIC BETWEEN LOW & HIGH LEVEL 1156 | MOVING 1157 | IGNORE 1158 | PRE-ARRANGED LOW POWER MODE 1159 | CUMULATIVE DAILY DOSAGE FOR 1190 USER PHIL ALREADY EXCEEDS EVALUATION GUIDELINES |
| KNOWN SOURCE #GG 1160 | MORE THAN TWO FEET 1161 | UPPER OFFICE 1162 | LOW & INCREASING 1163 | NOT MOVING 1164 | SEND ACTION REQUEST TO SOURCE 1165 | PRE-ARRANGED MONETARY CREDIT 1166 | CUMULATIVE HOURLY DOSAGE FOR 1192 USER ERIN IS BELOW EVALUATION GUIDELINES |
| UNKNOWN SOURCE #HH 1167 | MORE THAN TEN FEET 1168 | ADJACENT STREET 1169 | ABOVE USER THRESHOLD LEVEL 1170 | MOVING 1171 | TRANSMIT WARNING ALARM TO USER 1172 | NOT ANY REMEDY AVAILABLE 1173 | |
| UNKNOWN SOURCE #JJ 1174 | ABOUT SEVENTY FEET 1175 | POWER TRANSMISSION STATION ON STATE STREET 1176 | HIGH & CONSTANT 1177 | NOT MOVING 1178 | SHOW OPTIONAL ROUTE MAP 1179 TO USER | NOT ANY REMEDY AVAILABLE 1180 | CUMULATIVE WEEKLY DOSAGE FOR THIS USER SITE IS BELOW PREFERRED GOVT 1194 HEALTH STD |
| KNOWN SOURCE #KK 1181 | N/A 1182 | HIGH VOLTAGE TOWER 1183 | LOW & CONSTANT 1184 | NOT MOVING 1185 | IGNORE 1186 | NEW 1187 REQUEST IS REQUIRED | |

DATA TABLE OF VARIOUS EMR SOURCES

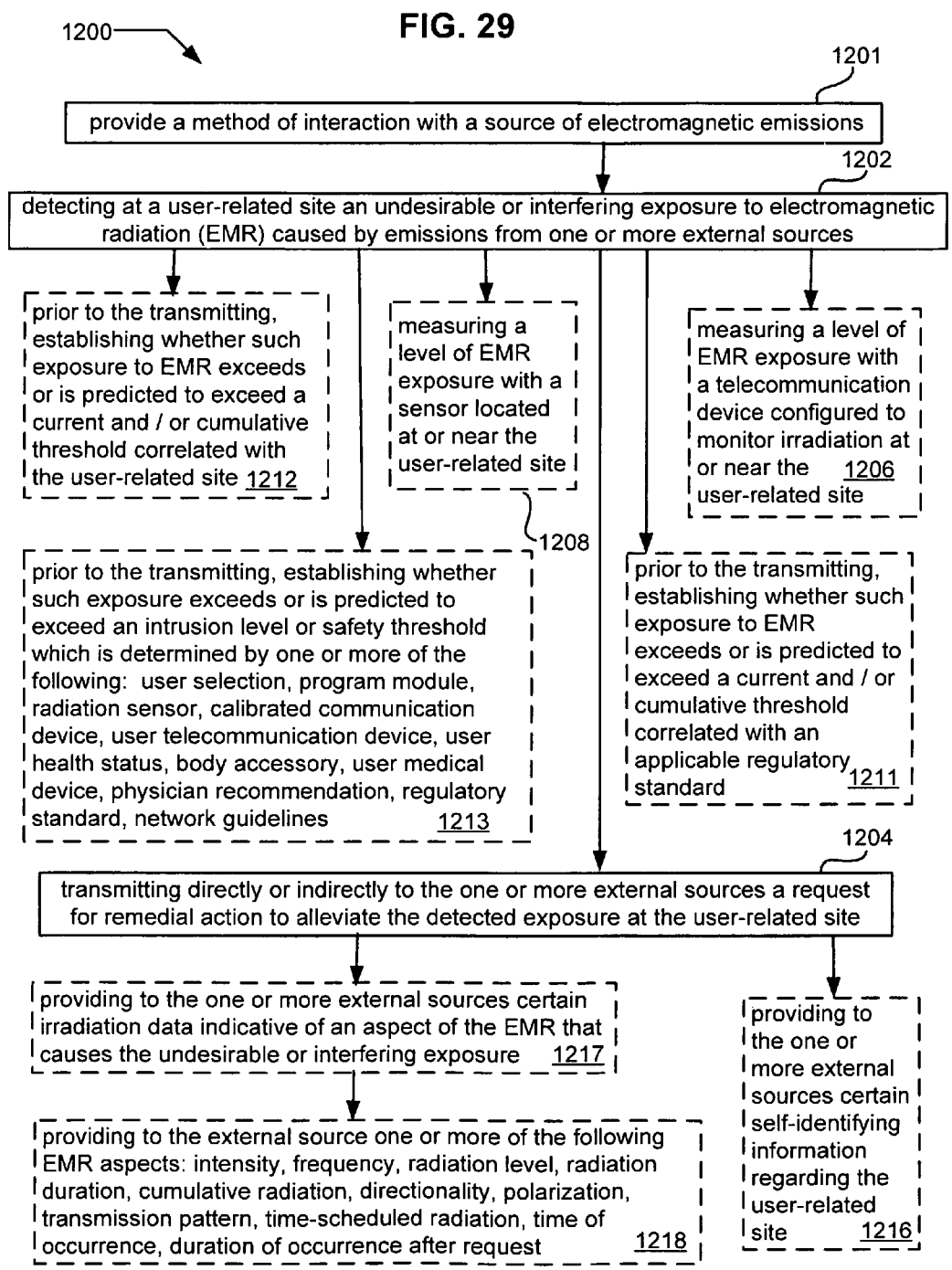

INTERACTIVE TECHNIQUE TO REDUCE IRRADIATION FROM EXTERNAL SOURCE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/803,143 entitled IRRADIATION SELF-PROTECTION FROM USER TELECOMMUNICATION DEVICE, naming Roderick A. Hyde, Muriel Y. Ishikawa, Jordin T. Kare, Thomas J. Nugent, Jr., Clarence T. Tegreene, Thomas A. Weaver, Lowell L. Wood, Jr., Victoria Y. H. Wood as inventors, filed 18 Jun. 2010 now U.S. Pat. No. 8,863,288, an application of which a currently application is entitled to the benefit of the filing date.

For purposes of the USPTO extra-statutory requirements, the present application constitutes a continuation-in-part of U.S. patent application Ser. No. 12/803,142 entitled PERSONAL TELECOMMUNICATION DEVICE WITH TARGET-BASED EXPOSURE CONTROL, naming Roderick A. Hyde, Muriel Y. Ishikawa, Jordin T. Kare, Thomas J. Nugent, Jr., Clarence T. Tegreene, Thomas A. Weaver, Lowell L. Wood, Jr., Victoria Y. H. Wood as inventors, filed 18 Jun. 2010 now U.S. Pat. No. 8,462,002, an application of which a currently application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

BACKGROUND

The present application relates to electromagnetic radiation monitoring and control devices and related methods, systems, components, computerized apparatus, software program products, and communication techniques.

SUMMARY

In one aspect, an exemplary method of interaction with a source of electromagnetic emissions may include detecting at a user-related site an undesirable or interfering exposure to electromagnetic radiation (EMR) caused by emissions from one or more external sources, and transmitting directly or indirectly to the one or more external sources a request for remedial action to alleviate the detected exposure at the user-related site.

In a further aspect, an exemplary method of interaction responsive to a request concerning electromagnetic radiation (EMR) may include receiving informational data regarding undesirable or interfering EMR exposure detected at a user-related site; evaluating the informational data regarding the EMR exposure to establish whether or not any remedial action is appropriate; and in response to the evaluation, authorizing remedial action that is deemed appropriate with respect to the user-related site.

In another aspect, an exemplary method for facilitating responsive action regarding electromagnetic irradiation may include receiving a communication from or on behalf of a user-related site that is subject to irradiation exposure from undesirable or interfering electromagnetic emissions, determining a possible source of the undesirable or interfering electromagnetic emissions, and sending a request for remedial action to an entity associated with the possible source.

In an additional aspect, an exemplary method for obtaining responsive action regarding electromagnetic irradiation may include detecting a level of irradiation exposure at a user-related site; transmitting empirical data regarding the level of irradiation to a designated entity for evaluation; and based on a result of the evaluation, authorizing the designated entity to send a request for remedial action to be implemented by an identified source of the undesirable or interfering electromagnetic emissions.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In another aspect, an exemplary system includes but is not limited to computerized components for managing interaction with a source of electromagnetic emissions, which system has the capability to implement the various process features disclosed herein. Examples of various system aspects are described in the claims, drawings, and text forming a part of the present disclosure.

Some system embodiments for obtaining responsive action regarding electromagnetic irradiation may include sensor means for detecting at a user-related site an undesirable or interfering exposure to electromagnetic radiation (EMR) caused by emissions from one or more external sources; and a communication module operably coupled to the sensor means, wherein the communication module is configured for transmitting directly or indirectly to the one or more external sources a request for remedial action to alleviate or otherwise compensate for the detected exposure at the user-related site.

Other system embodiments for providing interaction concerning electromagnetic radiation (EMR) may include communication interface means for receiving informational data regarding undesirable or interfering EMR exposure detected at a user-related site, and computerized processing means for evaluating the informational data regarding the EMR exposure in accordance with applicable guidelines to establish whether or not any remedial action is appropriate. A related system component may include a communication module operably coupled to the computerized processing means and configured to implement remedial action based on the evaluation of the informational data.

Further system embodiments for facilitating responsive action regarding electromagnetic irradiation may include interface means for receiving a communication from or on behalf of a user-related site that is subject to irradiation exposure from undesirable or interfering electromagnetic emissions, data processing means for determining a possible source of the undesirable or interfering electromagnetic emissions, and a communication module configured to send a request for remedial action to an entity associated with the possible source.

Additional system embodiments for obtaining responsive action regarding electromagnetic irradiation may include sensor means for detecting a level of irradiation exposure at a user-related site, and communication means configured for transmitting empirical data regarding the level of irradiation to a designated entity for evaluation. Related possible system features may include computer processing means operably linked to receive the transmitted empirical data and configured for evaluation of the level of irradiation, and based on a result of such evaluation the computer processing means further configured to request remedial action for implementation by an identified source of the undesirable or interfering electromagnetic emissions.

In a further aspect, a computer program product may include computer-readable media having encoded instructions for executing a method of interaction with a source of electromagnetic emissions, wherein the method may include detecting at a user-related site an undesirable or interfering exposure to electromagnetic radiation (EMR) caused by emissions from one or more external sources, and transmitting to an entity associated with the one or more external sources a request for remedial action to alleviate and/or provide offsetting consideration for the detected exposure at the user-related site.

In another aspect, a computer program product may include computer-readable media having encoded instructions for executing a method of interaction responsive to a request concerning electromagnetic radiation (EMR), wherein the method may include receiving informational data regarding undesirable or interfering EMR exposure detected at a user-related site, and evaluating the informational data regarding the EMR exposure to establish whether or not any remedial action is appropriate. A related method aspect may include based on one or more evaluation guidelines, authorizing remedial action that is deemed appropriate with respect to the user-related site.

In an additional aspect, a computer program product may include computer-readable media having encoded instructions for executing a method of obtaining responsive action regarding electromagnetic irradiation, wherein the method may include detecting a level of irradiation exposure at a user-related site, and transmitting empirical data regarding the level of irradiation to a designated entity for evaluation. A related aspect may include based on one or, more evaluation guidelines, authorizing a request for remedial action to be sent to an identified source of the undesirable or interfering electromagnetic emissions.

In some aspects, a computer program product may include computer-readable media having encoded instructions for executing a method of facilitating responsive action regarding electromagnetic irradiation, wherein the method may include receiving a communication regarding a user-related site that is subject to irradiation exposure from undesirable or interfering electromagnetic emissions, determining a possible source of the undesirable or interfering electromagnetic emissions, and sending a request for remedial action to an entity associated with the possible source.

In addition to the foregoing, various other method and/or system and/or program product aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2 is a schematic block diagram depicting exemplary irradiation protection aspects regarding telecommunication units at fixed or variable locations relative to a user.

FIG. 3 is a schematic block diagram depicting exemplary irradiation protection aspects regarding telecommunication units associated with a vehicle.

FIG. 4 shows exemplary data tables for varied emission and exposure values.

FIG. 15 is a high level flow chart for additional exemplary irradiation protection features.

FIG. 26 is a schematic block diagram depicting additional exemplary embodiment features regarding alleviation of irradiation exposure at a moving user-related site.

FIGS. 27-28 show representative data tables regarding interactive aspects of various EMR sources.

FIG. 29 is a high level flow chart illustrating additional possible interactive techniques for irradiation protection.

DETAILED DESCRIPTION

Figure 1:
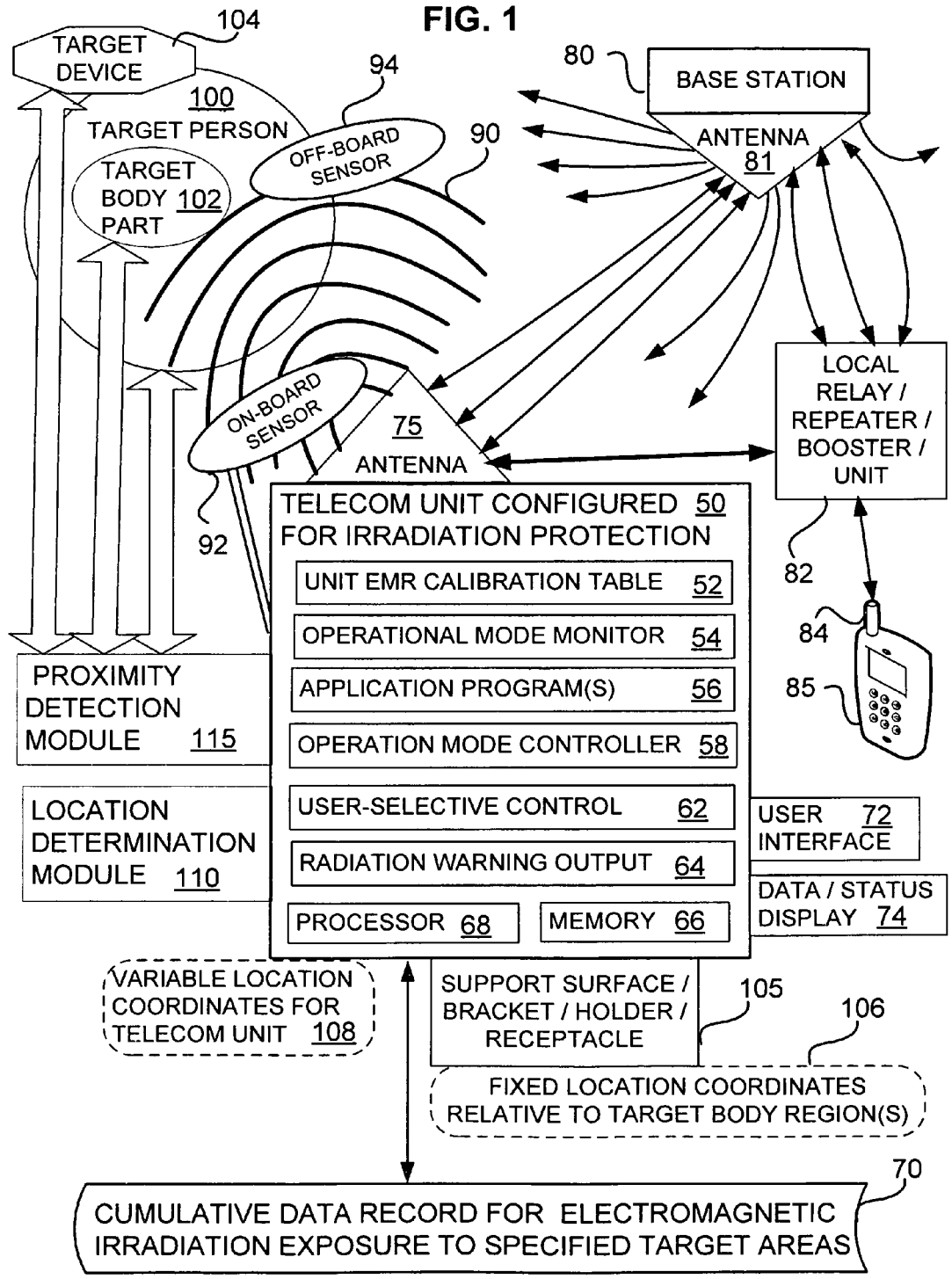
FIG. 1 is a schematic block diagram illustrating exemplary embodiment features for a telecommunication unit configured to provide irradiation protection.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences.

In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory or location even if components are located outside the territory or location. For example, in a distributed computing context, use of a distributed computing system may occur in a territory or location even though parts of the system may be located outside of the territory or location (e.g., relay, server, processor, signal-bearing medium, transmitting computer, receiving computer, etc. located outside the territory or location).

A sale of a system or method may likewise occur in a territory even if components of the system or method are located and/or used outside the territory. Further, implementation of at least part of a system for performing a method in one territory does not preclude use of the system in another territory.

As used herein, the term "vehicle" encompasses devices for conveying persons or objects, including without limitation automobiles, trucks, motorcycles, buses, trains, and other land conveyances, boats, ferries, ships, submarines, underwater vehicles, and other watergoing vessels, aircraft, spacecraft, and other airborne transports.

FIG. 1 is a schematic block diagram illustrating exemplary embodiment features for an irradiation protection system regarding attenuated electromagnetic radation emissions 90 generated from a telecommunication unit 50 toward a target person 100, a target body part 102, and/or a target device 104 associated with the target person 100. One or more user telecommunication units 50, 85 may respectively include antennas 75, 84 for data transmissions directly to or from antenna 81 of base station 80. In some instances such data transmissions may be facilitated indirectly via a local relay or repeater or booster unit 82.

The illustrated embodiment for telecommunication (telecom) unit 50 is configured to include various components that facilitate irradiation protection, include an eletromagnetic radiation (EMR) calibration table 52, operation mode monitor 54, one or more application programs 56, operation mode controller 58, user-selective control 62, radiation warning output 64, memory 66 and processor 68. Additional features may include user interface 72 and data/status display 74.

Some system embodiments may provide a receptacle 105 (e.g., surface, bracket, holder, etc.) adapted to position the telecommunication unit 50 for functional availability to a user. It will be understood that an evaluation of irradiation risks regarding the target person 100 or target body part 102 or target device 104 may be at least partially dependent on determining an approximate location for the telecommunication unit 50 during an active operation mode. Accordingly a system feature may include a location determination module 110 for obtaining fixed telecom unit location coordinates relative to one or more target body regions 106, as well as obtaining variable telecom location coordinates relative to one or more target body regions 106. The location determination module may be incorporated with or otherwise linked with the telecom unit 50 for appropriate data processing regarding irradiation risks.

It will be understood that in some circumstances the telecom location coordinates may already be known or predetermined (e.g., mounted in an identifiable given location relative to a user's body). However in other circumstances variable telecom location coordinates may be obtained in real time (e.g., a hand-held mobile telecom unit) in order to evaluate an irradiation exposure risk for a target body region of a user.

It will be further understood that an evaluation of irradiation risks may be at least partially dependent on determining an approximate separation distance between the telecom unit 50 and the target person 100 or target body part 102 or target device 104. Accordingly an exemplary system feature may include a proximity detection module 115 for detecting and/or monitoring such approximate separation distance. In some instances the separation distance may be determined relative to the antenna 75 (e.g., internal or external antenna) of the telecom unit 50, or relative to the receptacle 105 for the telecom unit 50, or relative to another identifiable aspect of the telecom unit 50.

Additional possible system components for detection and/or monitoring of electromagnetic emissions generated from the telecom unit 50 may include an on-board sensor 92 incorporated with the telecom unit 50 as well as in some instances an off-board sensor 94 preferably located in close proximity to one or more targeted body regions 100, 102, 104. Such sensors 92, 94 may be desirable for some embodiments to transmit pertinent data via communication links to the telecom unit 50 as well as transmit pertinent data via communication links to a cumulative data record 70 for electromagnetic irradiation exposure to specified target areas. In some embodiments where a calibrated radiation value for the telecom unit 50 has already been determined (e.g., by the manufacturer or seller or user or third party, etc.), the sensors 92, 94 may not be required to provide real-time irradiation data. In other embodiments a previously calibrated radiation value may provide a sufficient basis for suggesting or implementing remedial action that minimizes excessive irradiation exposure of a targeted body region of a user.

FIG. 2 is a schematic block diagram depicting exemplary system components configured to provide electromagnetic radiation protection (e.g., risk assessment, output data, warning signal, remedial action, etc.) to a user 120 of a telecom unit 115 (e.g., mobile phone, etc.) that may be operated in various locations relative to the user 120 while sending and/or receiving communication signals directly with another communication transceiver or via a local network or via one or more transmission towers 172, 192. Typical locations for the telecom unit 115 may be handheld 171 (e.g., displaced body location 170, adjacent head location 171) as well as receptacle-type locations in an enclosed pants pocket 175 or partially exposed chest shirt pocket 185 or on a belt 180. Another possible location may be head-mounted with an earpiece 187 and microphone 188 having wired 189a or wireless 189b connections. In some instances the telecom unit 115 may be positioned at a location 195 separate and independent of the user 120 such as on a desk or table 196. Of course other locations are possible, and the depicted locations are for purposes of illustration only.

An exemplary system embodiment for a telecommunication EMR protection unit 125 may include an operation mode monitor & controller 140 configured to monitor and/or control various operational modes 130 of the telecom unit 115 that are related to the generation of radiation emissions. Exemplary operational modes may include off-line 131, on-line 132, text send and/or receive 133, voice mail store 134, voice send and/or receive 136, signal search 137, and reduced power 138. It will be understood that other operational modes could be related to radiation emissions, and the depicted examples are for purposes of illustration only.

The telecommunication EMR protection unit 125 and its operation mode monitor & controller 140 may be operably coupled to a lookup table that includes data for varied EMR intrusion levels 150, wherein one or more such EMR intrusion level may be associated with different target body regions and/or different types of users. As illustrated in FIG. 2, exemplary target body regions may include a body implant device 161, and may further include an electronic body unit 162. Exemplary identifiable individual users of the telecom unit 115 having different irradiation risks as well as in some instance having different selective or consequential remedial actions may include Roger 151, Bob 152 and Amy 153. Exemplary categories of telecom users having different irradiation profiles (e.g. target body region, type of remedial action, cumulative irradiation limits, etc.) may include children under six years of age 154, youngsters in the age range six through sixteen 156, adults over twenty years of age 157, pregnant women 158, and frequent telecom users 159. Depending on the circumstances, some target body regions and some user types may not be applicable, and additional target body regions and other user types may be included in order to customize the irradiation protection.

The telecommunication EMR protection unit 125 and its operation mode monitor & controller 140 may also be operably coupled with a location determination module 200 configured for confirmation of a predetermined and/or real-time location for an EMR source (e.g., mobile telecom unit 115). As illustrated in FIG. 2, such locations may include an enclosed pants pocket 203, chest shirt pocket 204, belt clip 206, workdesk holder 207 and head set 208. The location determination module 200 may be incorporated in the telecom unit 115 or located separately, and is configured to recognize and process a detectable parameter 212 that is associated with and identifies each location.

It will be understood that some system embodiments may include location coordinates for a known location (e.g., receptacle-type location), yet nevertheless require additional confirmation that a mobile version of the telecom unit 115 is currently positioned at such known location. In other system embodiments, a non-mobile version of the telecom unit 115 may always be fixedly attached at such known location (e.g., desktop transceiver, permanent vehicle transceiver, etc.)

For example, detection of minimal ambient light 213 could confirm the real-time location of a mobile version of telecom unit 115 in the enclosed pants pocket 203; detection of a louder heartbeat 214 could confirm the real-time location of a mobile version of the telecom unit 115 in the chest shirt pocket 204, and detection of a conductive junction could confirm the real-time location of a mobile version the telecom unit 115 attached to the belt clip 206.

Other examples may include detection of an activated direct-line code signal 217 as confirmation of the real-time location of the telecom unit 115 in the workdesk holder, and may further include detection of a thermal output 218 as confirmation of the real-time location of the telecom unit 115 as part of the headset 208. Depending on the circumstances, the workdesk holder for some users may constitute a permanent attachment for the telecom unit 115, or may constitute for other users an optional location for a mobile version of the telecom unit 115. Similarly in some circumstances the headset location may be an optional telecom unit location for some users (e.g., only used when driving a vehicle, etc.), or in other circumstances may be a virtually permanent telecom unit location (e.g., telemarketer employee continually making calls while keyboarding results, etc.).

Various technology techniques may be incorporated in the system components depicted in FIG. 2, including circuitry configured to ascertain a separation distance between the EMR source and a targeted body region by processing data obtained by one or more of the following types of proximity measurement and/or location detection techniques: ultrasound, infrared (IR), ultraviolet (UV), radio frequency (RF), radio frequency identification (RFID) tag, capacitive sensor, electromagnetic reflection, phase-change, charge-coupled device (CCD) light detection, thermal sensor, image recognition, and audio time of flight.

An EMR source located in the enclosed pants pocket 203 may provide increased irradiation risk to reproductive organs. An EMR source located in the chest shirt pocket 204 may provide increased irradiation risk to the cardiovascular region (e.g., heart, lungs, heart pacemaker, etc.). An EMR source located on the belt clip 206 may provide increased irradiation risks to the abdomen and to reproductive organs. An EMR source located on a workdesk holder 207 have provide increased cumulative irradiation risk to the entire body. An EMR source located in a headset 208 may provide increased irradiation risk to the cerebral area (e.g. eyes, ears, brain, etc.). It will be understood that in some system embodiments, various types of intrusions level or warnings or remedial action or the like may be customized to provide appropriate irradiation protection for a particular user of the telecommunication unit 115.

Referring to exemplary features depicted in the schematic block diagram of FIG. 3, a vehicle 240 may have a driver 242 and a passenger 244 who are each potential users of a transceiver 245 capable of sending and or receiving data signals 246 via wireless transmissions. During operational usage, the transceiver 245 may during certain time periods be held in a fixed position by a transceiver support holder 275 have predetermined location parameter 276. The transceiver 245 may have a communication link directly or indirectly with an EMR control module 250 that could be incorporated as part of the transceiver 245 or situated in the vehicle 240 or located remotely from the vehicle 240 depending on the circumstances.

The EMR control module 250 may include a user interface 252, processor 254, data/status display 256, as well as additional components including GPS unit 262, proximity detection module 263, remedial action selector 266, and warning indicator 267 (e.g., visual, aural, musical, etc.). Further possible components may include one or more radiation monitors and/or sensors 260 for detection of radiation emissions generated by the transceiver 245 and/or for monitoring operational modes of transceiver 245 that generate radiation emissions above one or more predetermined intrusion levels. A further component may include a telecom operation mode controller 270 for implementing remedial action such as a modification and/or termination of a currently active operational mode.

Additional reference data features may be provided for different types of transceivers. For example, the EMR control module 250 may include an EMR calibration table for a telecom unit "B" 273 as well as a different EMR calibration table for a telecom unit "A" 272. As a further example, the EMR control module 250 may include radiation profile data for different users, including one or more irradiation protection limits for a driver owner 281, one or more irradiation protection limits for a driver teenager 282, one or more irradiation protection limits for a passenger #1 (see 283), and one or more irradiation protection limits for a passenger #2 (see 284).

Some exemplary embodiments may further provide wired 287 and/or wireless 288 communication links between the EMR control module 250 and a cumulative radiation record 290 for maintaining updated irradiation exposure data applicable to driver owner 297, driver teenager 296, passenger #1 (see 292), and passenger #2 (see 291).

It will be understood that a transceiver 245 that is utilized in variable rather than fixed locations within vehicle 240 may also be subjected to the monitoring and/or control techniques disclosed herein to provide protection to a driver or passenger against excessive irradiation exposure.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

FIG. 4 is a schematic representation of exemplary data tables for varied emission & exposure values. It will be understood that some embodiments may provide emphasis on EMR emission values that are monitored or measured at or in close proximity to a radiation source (e.g., a user's telecom unit). Other embodiments may provide emphasis on irradiation dosage values that are monitored or measured at or in close proximity to a body-related target region (e.g., head, medical appliance, reproductive organs, etc.) Other embodiments may provide current or cumulative irradiation protection information and/or remedial action based on processing EMR radiation and dosage values obtained from diverse sensors and/or monitors and/or data records.

A radiation emission priority table 310 may include data for multiple user IDs 325 associated with one or more particular telecommunication device models 320. For purposes of illustration, reference is made to a commonly used power density measurement unit for characterizing an electromagnetic field. As used herein, power density measurements per unit area are expressed in terms of microwatts per square centimeter. Such measurements may provide reasonable accuracy when the point of measurement is a sufficient distance away from EMR emitter (e.g., more than several wavelengths distance from a typical EMR source).

As a first example, a cell phone "AA" (see 321) for a user identified as "Amy pregnant" (see 326) may include a searching 331 operation mode having a pre-calibrated radiation emissions range cap 335 with a value or "#qq microwatts/square cm" (see 337). Amy may have a user intrusion level 345 that applies to her individually (see 346). In addition, actual radiation values 340 for Amy may be obtained by detection or monitoring (see 342) during the searching 331. With respect to a target region 350 for Amy that includes her torso & reproductive organs (see 351), a correlated real-time radiation limit 355 may be selected or automatically determined (see 356), and a correlated cumulative radiation limit 360 may be selected or automatically determined (see 361).

As another example for Amy, a transmit/receive 332 operation mode may have a pre-calibrated radiation emissions range cap 335 with a value or "#zz microwatts/square cm" (see 338). In addition, actual radiation values 340 for Amy may be obtained by detection or monitoring (see 343) during the transmit/receive 333. With respect to a same target region 350 for Amy that includes her torso & reproductive organs (see 351), a same correlated real-time radiation limit 355 may be selected or automatically determined (see 356), and a same correlated cumulative radiation limit 360 may be selected or automatically determined (see 361).

As a second example, a mobile unit "BB" (see 323) for a user identified as "Bob age 65" (see 328) may include a searching 334 operation mode having a pre-calibrated radiation emissions range cap 335 with a value or "#xx microwatts/square cm" (see 339). Bob may have a user intrusion level 345 that applies to him individually (see 347). In addition, actual radiation values 340 for Bob may be obtained by detection or monitoring (see 344) during the searching mode 334. With respect to a target region 350 for Bob that includes his heart/lungs (see 354), a correlated real-time radiation limit 355 may be selected or automatically determined (see 358), and a correlated cumulative radiation limit 360 may be selected or automatically determined (see 363).

As another example for Bob, a transmit/receive 333 operation mode may have a pre-calibrated radiation emissions range cap 335 with a value or "#yy microwatts/square cm" (see 338). In addition, actual radiation values 340 for Bob may be obtained by detection or monitoring (see 343) during the transmit/receive mode 333. With respect to a target region 350 for Bob that includes his hearing aid (see 353), a correlated real-time radiation limit 355 may be selected or automatically determined (see 357), and a correlated cumulative radiation limit 360 may be selected or automatically determined (see 362).

Further exemplary system embodiments shown in FIG. 4 include an irradiation exposure priority table 365 for various user-related target regions 370 associated with one or more particular telecommunication devices 375. For purposes of illustration, reference is made to an irradiation exposure standard adopted by the FCC (Federal Communications Commission), which standard is based on a specific absorption rate (SAR) measured by the amount of a telecom unit's radiation energy in watts absorbed per kilogram of tissue.

As a first example, an applicable user-related target region 370 may includes any body surface (see 371) of the user. An applicable user telecom device 375 may include a fixed location mobile unit "CC" with an onboard radiation sensor (see 376) having a real-time exposure threshold limit 380 based on user-choice in a range of SAR 1.6-4.0 watts per kilogram (see 381). A related cumulative exposure threshold limit 385 that is selected or otherwise determined may have a particular dosage exposure value (see 386). In a situation wherein one or the other of the predetermined threshold limits 381, 386 is exceeded, an appropriate responsive action 390 may cause a selective or consequential remedial action such as "modify telecom unit power mode" (see 391).

As another example, an applicable user-related target region 370 may include a heart appliance such as a pacemaker (see 372) of the user. An applicable user telecom device 375 may include a variable location cell phone "DD" with an offboard chest sensor (see 377) having a real-time exposure threshold limit 380 based on the heart applicance device safety specification (see 382). A related cumulative exposure threshold limit 385 that is selected or otherwise determined may have a particular dosage exposure value (see 387). In a situation wherein one or the other of the predetermined threshold limits 381, 386 is exceeded, an appropriate responsive action 390 may cause a selective or consequential remedial action such as "turn off cell phone" (see 392).

As an additional example, an applicable user-related target region 370 may include the head, eyes and/or ears (see 373) of the user. An applicable user telecom device 375 may include a fixed and variable location portable landline phone "EE" (see 3778) having a real-time exposure threshold limit 380 that is selected or otherwise determined to be SAR 1.6 watts per kilogram (see 383). A related cumulative exposure threshold limit 385 that is selected or otherwise determined may have a particular dosage exposure value (see 388). In a situation wherein one or the other of the predetermined threshold limits 383, 388 is exceeded, an appropriate responsive action 390 may cause a selective or consequential remedial action such as "activate warning alarm" (see 393).

It will be understood that the specific types of radiation protection information depicted in the exemplary data tables of FIG. 4 are for purposes of illustration and are not intended to be limiting. Additional categories and applicable data values and remedial actions may be provided in accordance with a user's preference or to a third party's decision or a product manufacturer's specification or other entity which may be responsible for administering the various irradiation protection schemes disclosed herein.

It will be understood that the exemplary system embodiments disclosed herein facilitate managing electromagnetic irradiation from a telecommunication device, and may include proximity determination means for acquiring estimated location parameters for a particular telecommunication device relative to a target body region of a user, as well as monitoring means for determining whether the particular telecommunication device is in an active operation mode that generates or is predicted to generate electromagnetic irradiation above a predetermined intrusion level. Additional system components may include control module means configured to be responsive to confirmation of the determined active operation mode in order to implement consequential or selective remedial action with respect to exposure of the target body region to attenuated electromagnetic emissions received from the particular telecommunication device.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry, having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

Figure 5:
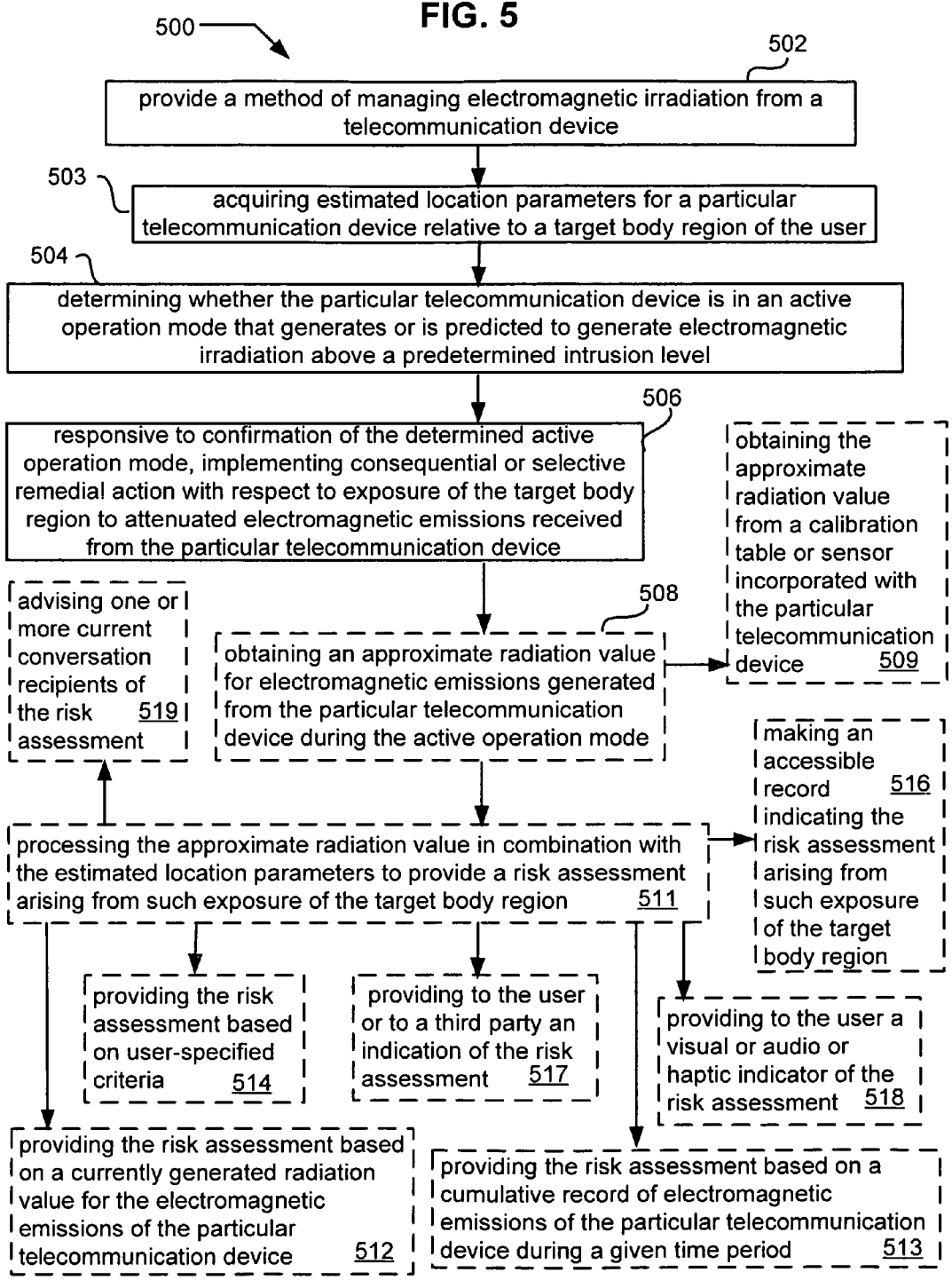
FIG. 5 is a high level flow chart for exemplary irradiation protection features.

Referring to the high level flow chart of FIG. 5, an exemplary process embodiment 500 provides a method of managing electromagnetic irradiation from a telecommunication device (block 502) that may include acquiring estimated location parameters for a particular telecommunication device relative to a target body region of a user (block 503), determining whether the particular telecommunication device is in an active operation mode that generates or is predicted to generate electromagnetic irradiation above a predetermined intrusion level (block 504); and responsive to confirmation of the determined active operation mode, implementing consequential or selective remedial action with respect to exposure of the target body region to attenuated electromagnetic emissions received from the particular telecommunication device (block 506).

Other possible process components may include obtaining an approximate radiation value for electromagnetic emissions generated from the particular telecommunication device during the active operation mode (block 508), and obtaining the approximate radiation value from a calibration table or sensor incorporated with the particular telecommunication device (block 509). Additional process aspects may include processing the approximate radiation value in combination with the estimated location parameters to provide a risk assessment arising from such exposure of the target body region (block 511). Further related risk assessment aspects may include providing the risk assessment based on a currently generated radiation value for the electromagnetic emissions of the particular telecommunication device (block 512), providing the risk assessment based on a cumulative record of electromagnetic emissions of the particular telecommunication device during a given time period (block 513), and providing the risk assessment based on user-specified criteria (block 514.

Other risk assessment features may include making an accessible data record indicating the risk assessment arising from such exposure of the target body region (block 516), providing to the user or to a third party an indication of the risk assessment (block 517), and providing to the user a visual or audio or haptic indicator of the risk assessment (block 518). Another possible risk assessment feature may include advising one or more current conversation recipients of the risk assessment (block 519).

Figure 6:
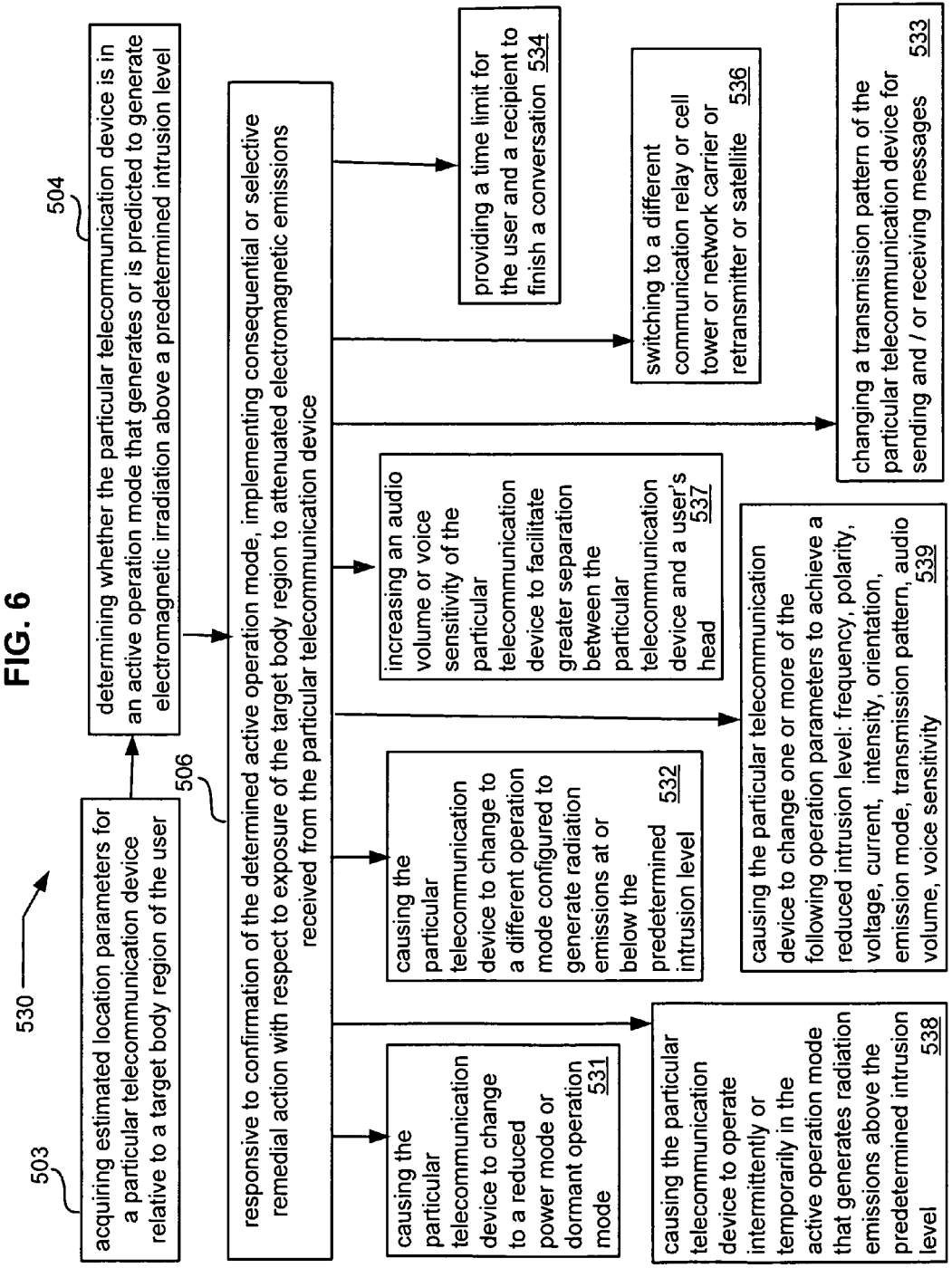
FIGS. 6-12 are more detailed flow charts illustrating further exemplary process features that may be incorporated in irradiation protection embodiments.

The process embodiment features 530 illustrated in the detailed flow chart of FIG. 6 may include previously described features 503, 504, 506 along with implementing various types of consequential or selective remedial action regarding irradiation risks. For example, such remedial action may include causing the particular telecommunication device to change to a reduced power mode or dormant operation mode (block 531), and in some instances may include causing the particular telecommunication device to change to a different operation mode configured to generate radiation emissions at or below the predetermined intrusion level (block 532).

Other possible remedial actions may include changing a transmission pattern of the particular telecommunication device for sending and/or receiving messages (block 533), providing a time limit for the user and a recipient to finish a conversation (block 534), and switching to a different communication relay or cell tower or network carrier or retransmitter or satellite (block 536). Some exemplary embodiments may further provide for increasing an audio volume or voice sensitivity of the particular telecommunication device to facilitate greater separation between the particular telecommunication device and a user's head (block 537).

FIG. 6 also depicts additional exemplary types of remedial action such as causing the particular telecommunication device to operate intermittently or temporarily in the active operation mode that generates radiation emissions above the predetermined intrusion level (block 538), as well as causing the particular telecommunication device to change one or more of the following operation parameters to achieve a reduced intrusion level: frequency, polarity, voltage, current, intensity, orientation, emission mode, transmission pattern, audio volume, voice sensitivity (block 539).

Figure 7:
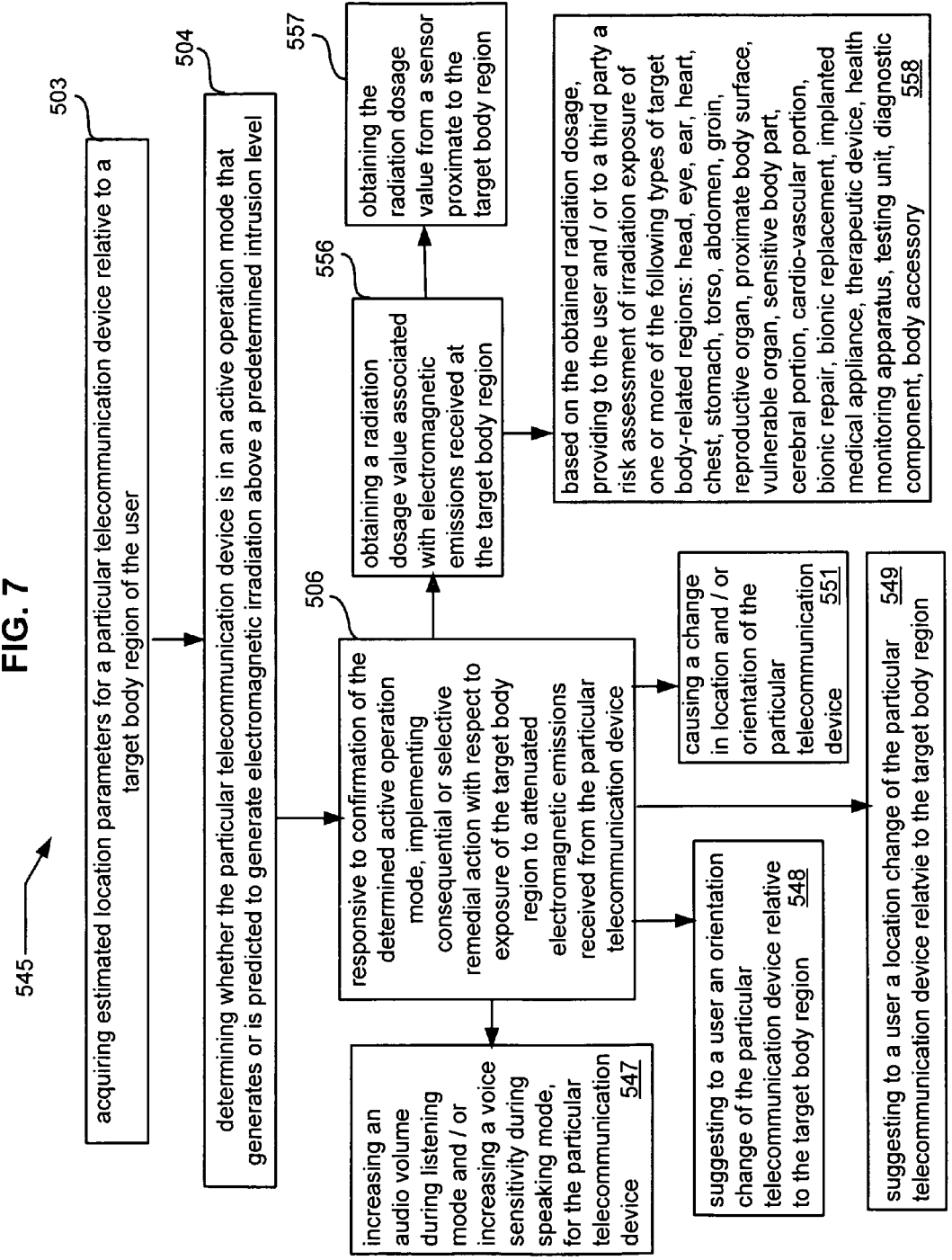

Referring to the various embodiment features 545 illustrated in FIG. 7, a possible process implementation may include previously described operations 503, 504, 506 as well as implementing consequential or selective remedial action such as increasing an audio volume during listening mode and/or increasing a voice sensitivity during speaking mode, for the particular telecommunication device (block 547). Other types of remedial action may include suggesting to a user an orientation change (block 548) or suggesting to a user a location change (block 549) of the particular telecommunication device, relative to the target body region. A further remedial action aspect may include causing a change in location and/or orientation of the particular telecommunication device (block 551).

Some exemplary embodiments may further include obtaining a radiation dosage value associated with electromagnetic emissions received at the target body region (block 556), and obtaining the radiation dosage value from a sensor proximate to the target body region (block 557). Another possible aspect may include based on the obtained radiation dosage, providing to the user and/or to a third party a risk assessment of irradiation exposure of one or more of the following types of target body-related regions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory (block 558).

Figure 8:
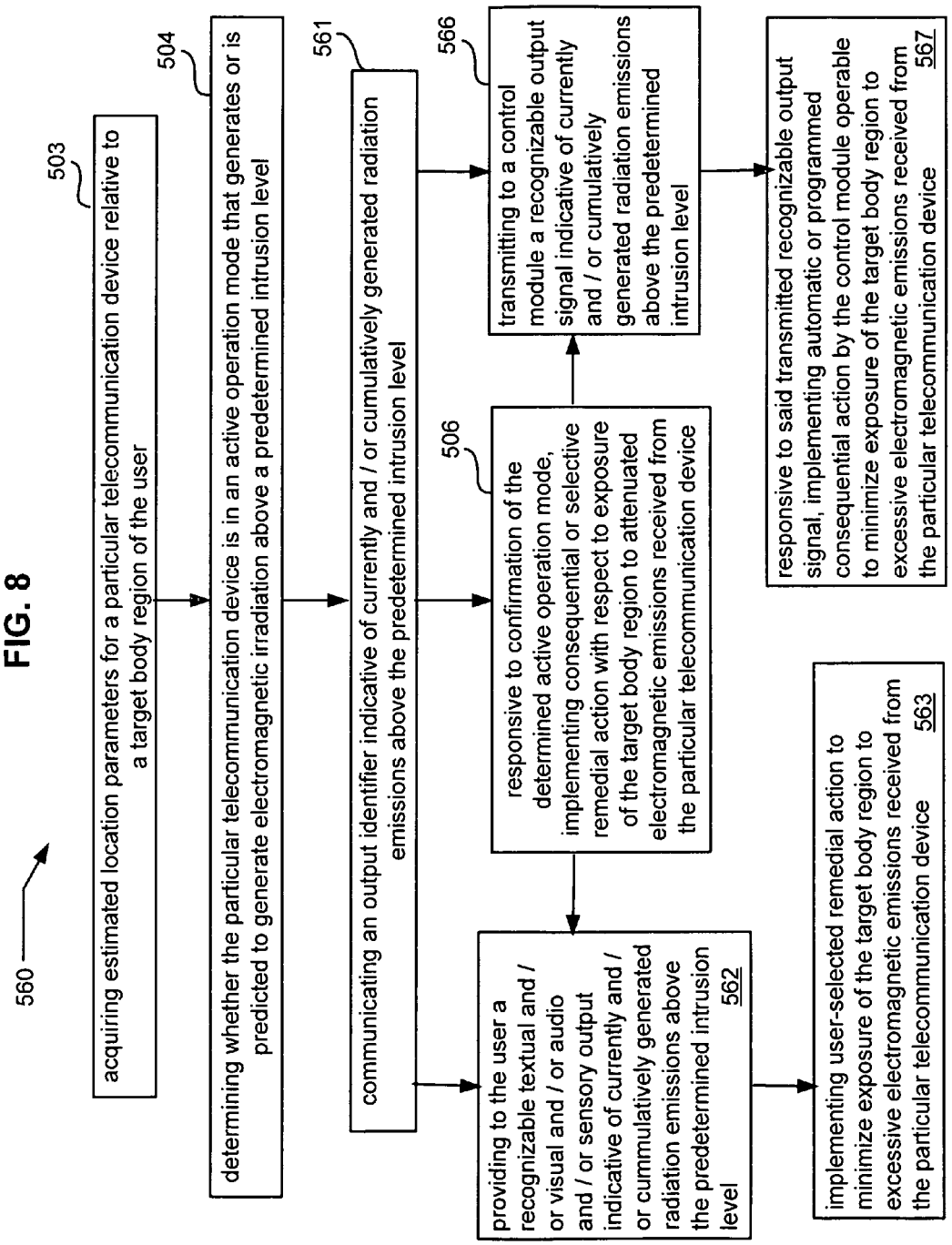

Various exemplary process embodiment features 560 disclosed in the flow chart of FIG. 8 may include previously described components 503, 504, 506 in combination with communicating an output identifier indicative of currently and/or cumulatively generated radiation emissions above the predetermined intrusion level (block 561). A related process aspect may provide to the user the output identifier that includes a recognizable textual and/or visual and/or audio and/or sensory output indicative of currently and/or cumulatively generated radiation emissions above the predetermined intrusion level (block 562). A further related possible aspect may include implementing user-selected remedial action to minimize exposure of the target body region to excessive electromagnetic emissions received from the particular telecommunication device (block 563).

In some instance an exemplary embodiment may include transmitting to a control module a recognizable output signal indicative of currently and/or cumulatively generated radiation emissions above the predetermined intrusion level (block 566), and may further include responsive to said transmitted recognizable output signal, implementing automatic or programmed consequential action by the control module operable to minimize exposure of the target body region to excessive electromagnetic emissions received from the particular telecommunication device (block 567).

Figure 9:
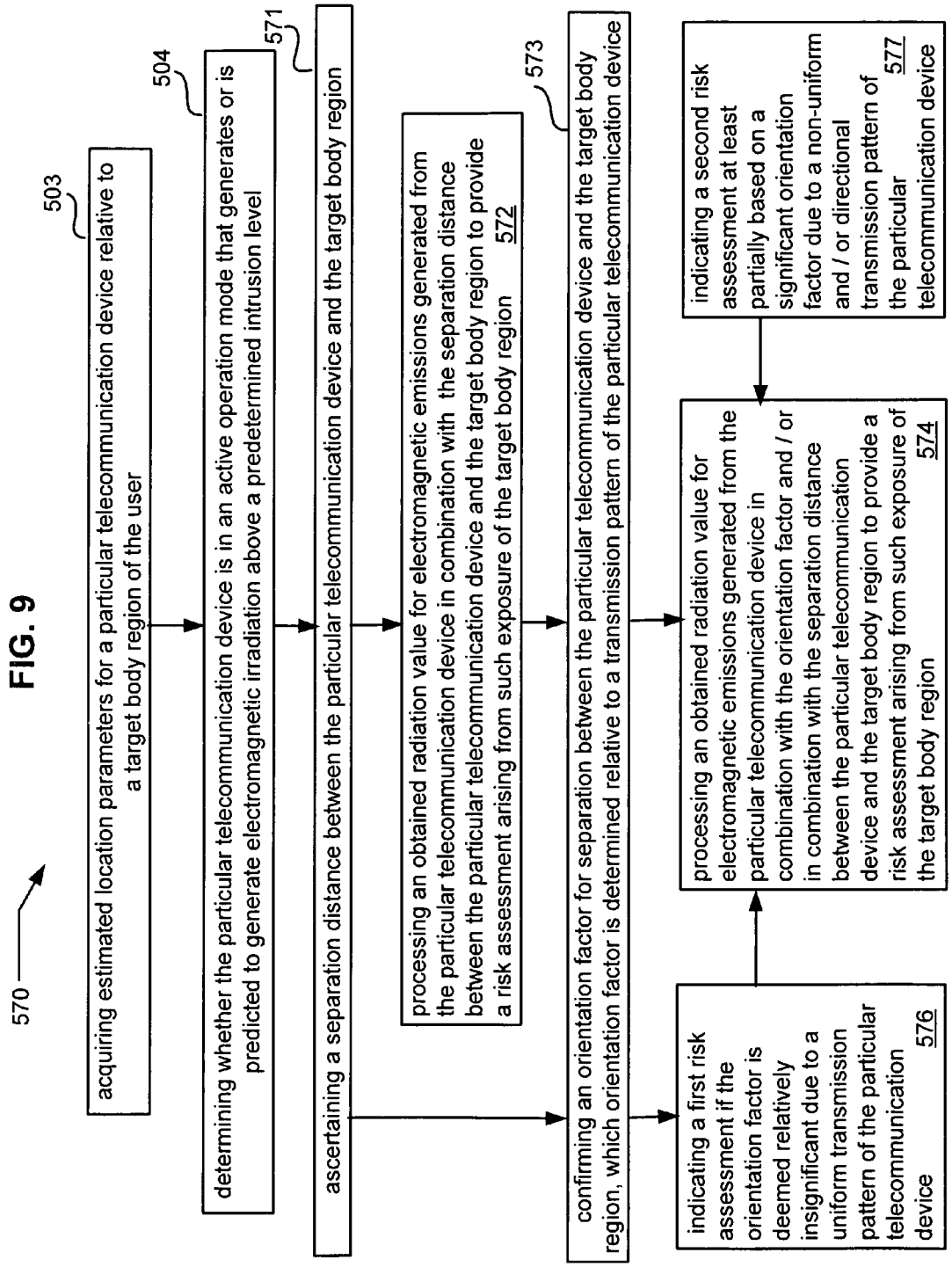

Referring to the detailed flow chart of FIG. 9, exemplary process features 570 may include previously described aspects 503, 504 along with ascertaining a separation distance between the particular telecommunication device and the target body region (block 571). A related aspect may include processing an obtained radiation value for electromagnetic emissions generated from the particular telecommunication device in combination with the separation distance between the particular telecommunication device and the target body region to provide a risk assessment arising from such exposure of the target body region (block 572).

Another possible process feature may include confirming an orientation factor for separation between the particular telecommunication device and the target body region, which orientation factor is determined relative to a transmission pattern of the particular telecommunication device (block 573). A related aspect may include processing an obtained radiation value for electromagnetic emissions generated from the particular telecommunication device in combination with the orientation factor to provide a risk assessment arising from such exposure of the target body region (block 574).

Additional possible risk assessment factors may include indicating a first risk assessment if the orientation factor is deemed relatively insignificant due to a uniform transmission pattern of the particular telecommunication device (block 576), and indicating a second risk assessment at least partially based on a significant orientation factor due to a non-uniform and/or directional transmission pattern of the particular device (block 577).

Figure 10:
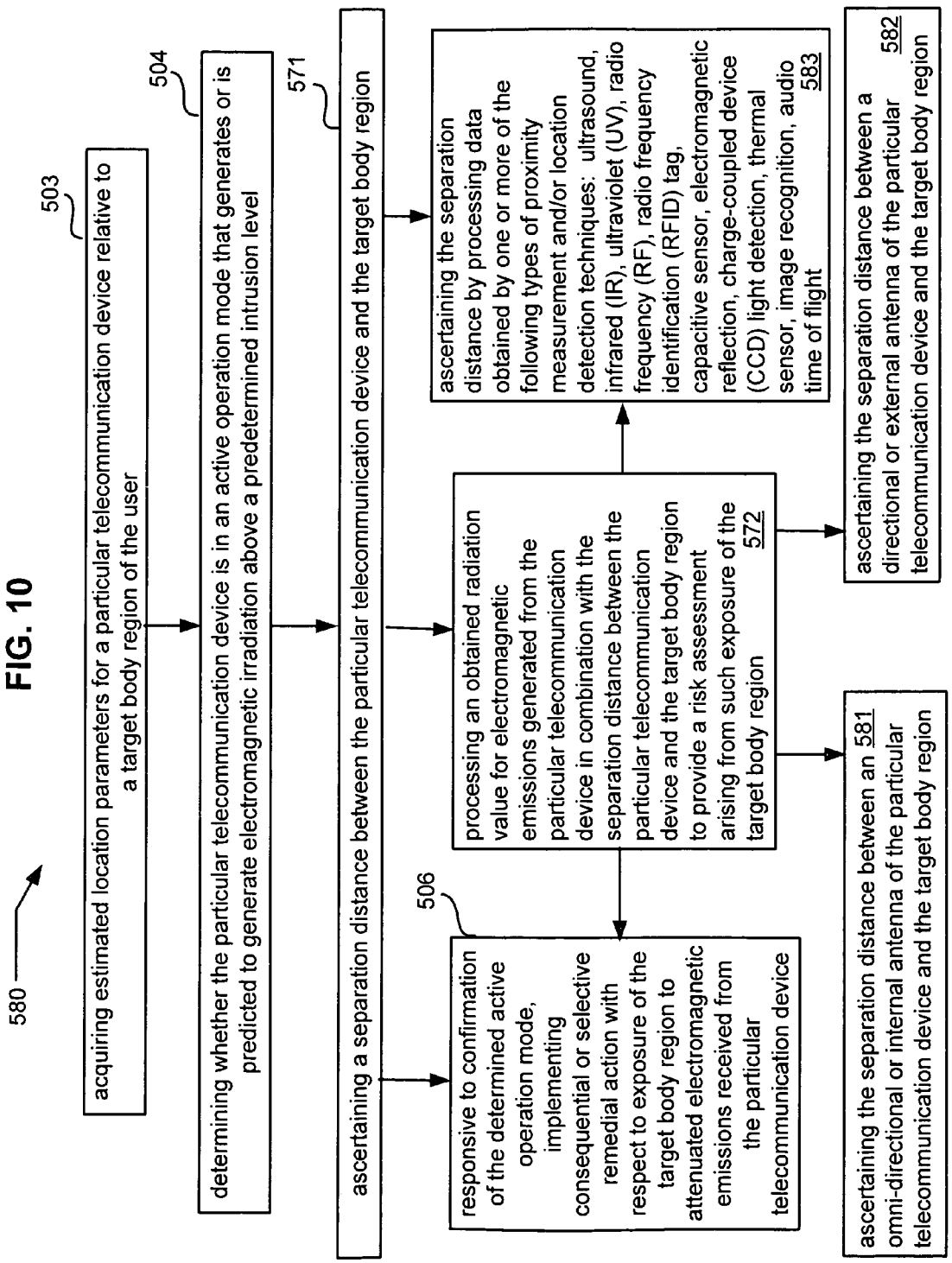

The detailed flow chart of FIG. 10 depicts various exemplary process features 580 including previously described components 503, 504, 506, 571, 572 in combination with various aspects related to the ascertained distance between the particular telecommunication device and the target body region. For example, some possible aspects may include ascertaining the separation distance by one or more of the following types of proximity measurement techniques: ultrasound, infrared (IR), ultraviolet (UV), radio frequency (RF), radio frequency identification (RFID) tag, capacitive sensor, electromagnetic reflection, phase-change, charge-coupled device (CCD) light detection, thermal sensor, image recognition, audio time of flight (block 583).

Additional exemplary embodiments may include ascertaining the separation distance between an omni-directional or internal antenna of the particular telecommunication device and the target body region (block 581). A further possible embodiment feature may include ascertaining the separation distance between a directional or external antenna of the particular telecommunication device and the target body region (block 582).

Figure 11:
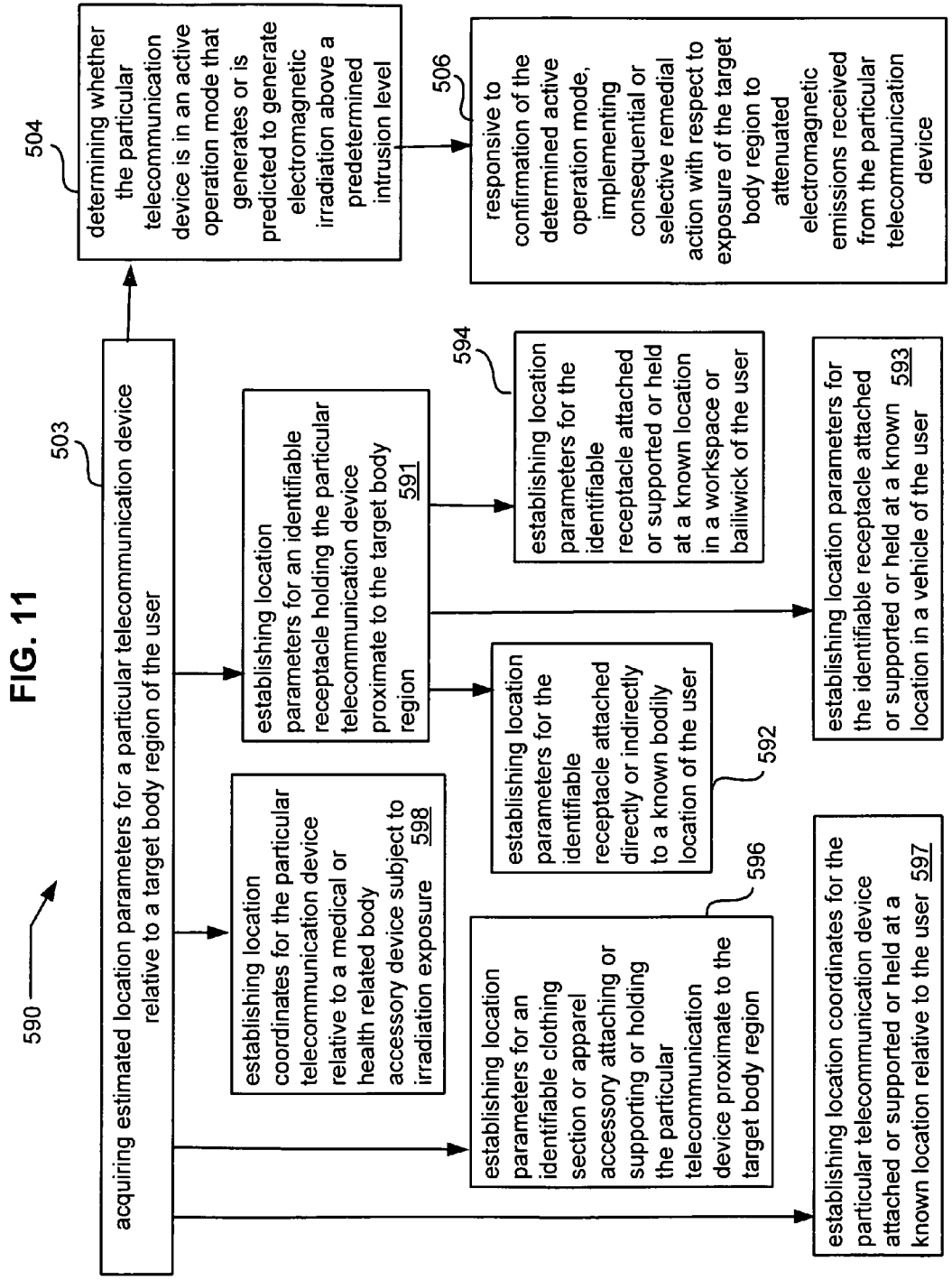

The exemplary process embodiment features 590 of FIG. 11 include previously described operations 503, 504, 506 along with establishing location parameters for an identifiable receptacle holding the particular telecommunication device proximate to the target body region (block 591). Related possible process features may include establishing location parameters for the identifiable receptacle attached directly or indirectly to a known bodily location of the user (block 592), and establishing location parameters for the identifiable receptacle attached or supported or held at a known location in a vehicle of the user (block 593). Additional possible aspects may include establishing location parameters for the identifiable receptacle attached or supported or held at a known location in a workspace or bailiwick of the user (block 594).

Some exemplary embodiment may include establishing location parameters for an identifiable clothing section or apparel accessory attaching or supporting or holding the particular telecommunication device proximate to the target body region (block 596). Other possible features may include establishing location parameters for the particular telecommunication device attached or supported or held at a known location relative to the user (block 597. Further possible enhancements may include establishing location coordinates for the particular telecommunication device relative to a medical or health related body accessory device subject to irradiation exposure (block 598).

Figure 12:
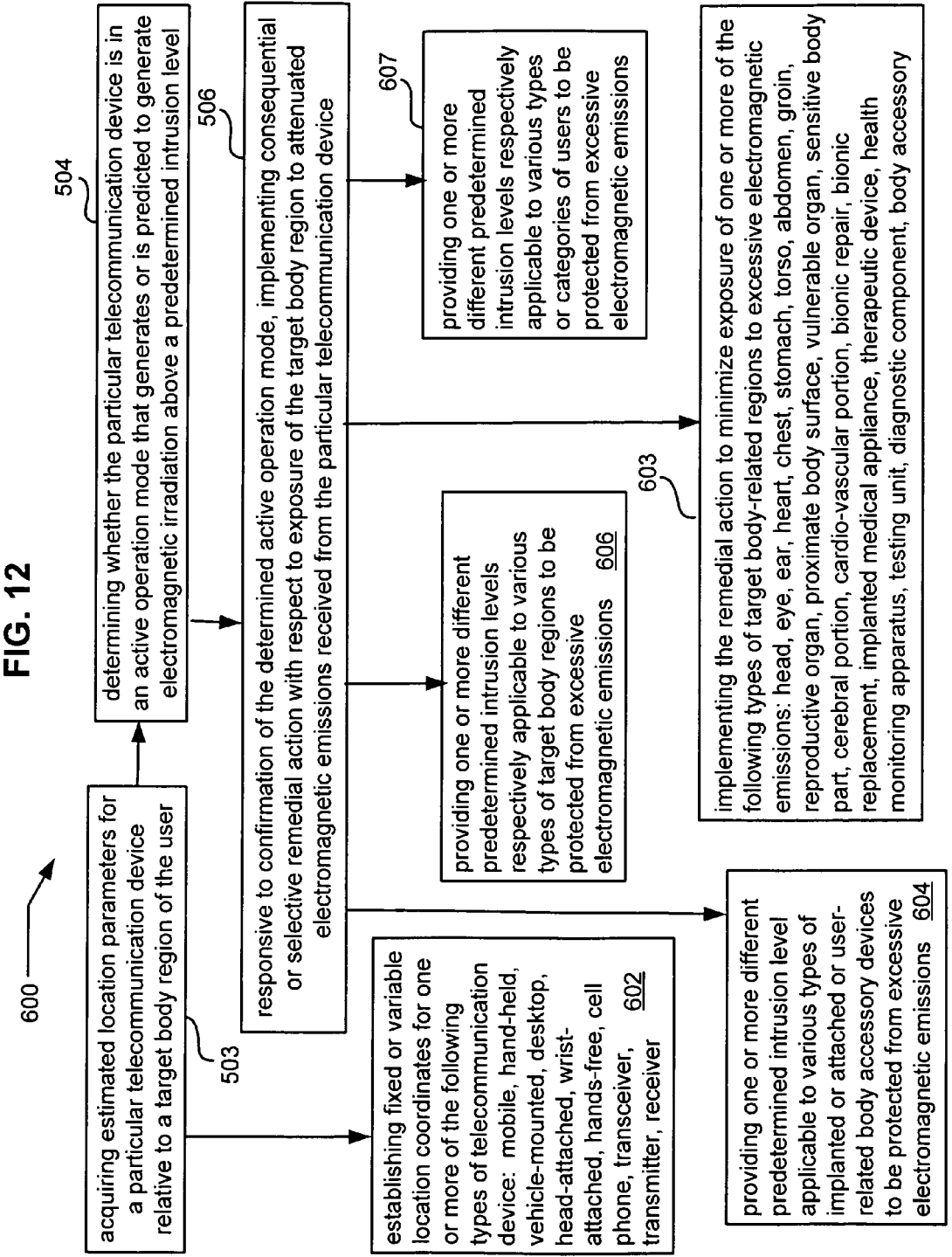

Referring to the detailed flow chart of FIG. 12, variously illustrated embodiment features 600 include previously described process aspects 503, 504, 506 in combination with establishing location parameters for one or more of the following types of telecommunication device: mobile, handheld, vehicle-mounted, desktop, head-attached, wrist-attached, hands-free, cell phone, transceiver, transmitter, receiver (block 602). Other possible process aspects may include implementing the remedial action to minimize exposure of one or more of the following types of target body-related regions to excessive electromagnetic emissions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory (block 603).

Additional possible process features depicted in FIG. 12 may include providing one or more different predetermined intrusion levels respectively applicable to various types of implanted or attached or user-related body accessory devices to be protected from excessive electromagnetic emissions (block 604). Other exemplary embodiment features may include providing one or more different predetermined intrusion levels respectively applicable to various types of target body regions to be protected from excessive electromagnetic emissions (block 606), and providing one or more different predetermined intrusion levels respectively applicable to various types or categories of users to be protected from excessive electromagnetic emissions (block 607).

Figure 13:
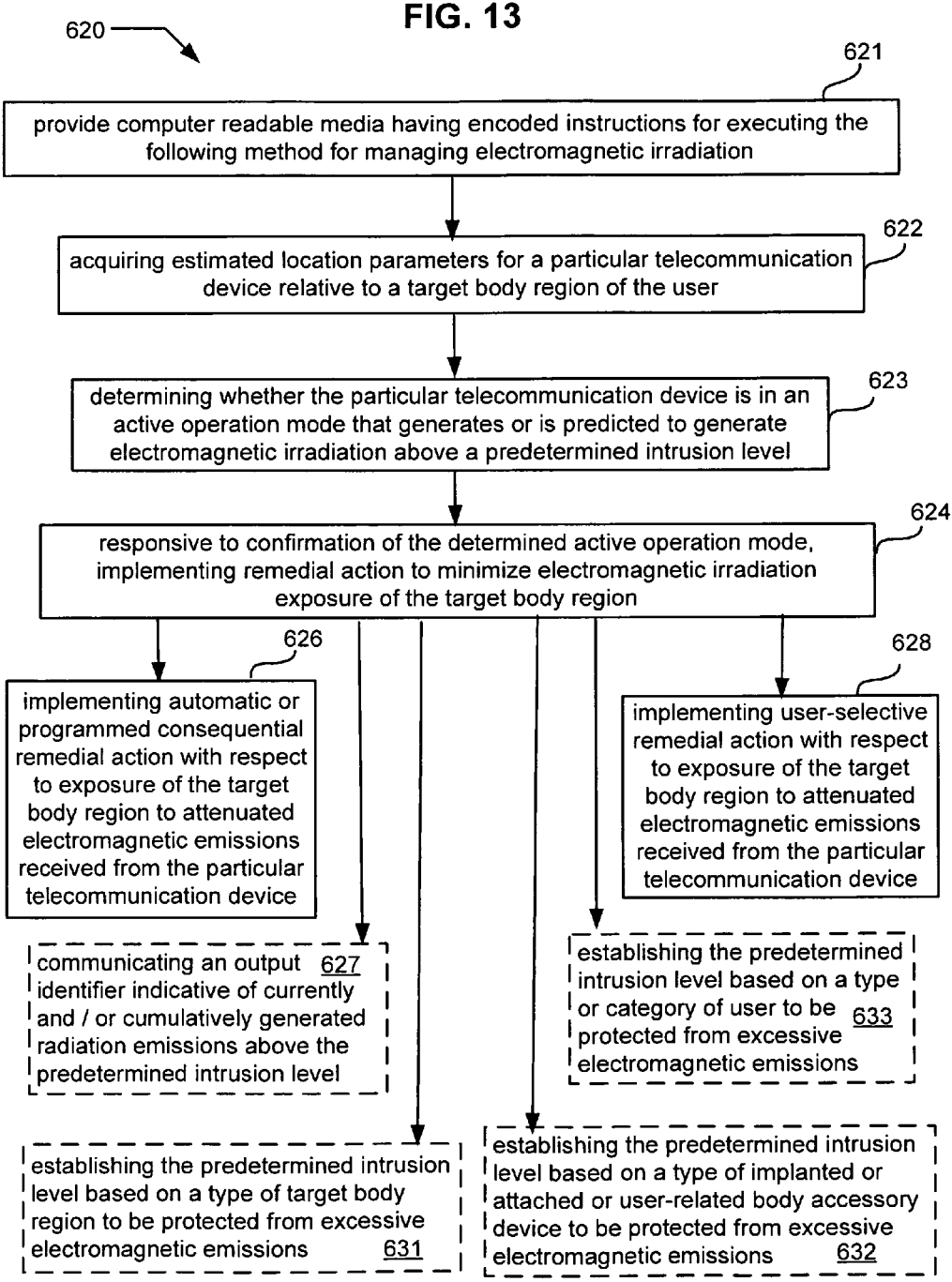
FIG. 13 is a diagrammatic flow chart for exemplary computer readable media embodiment features.

FIG. 13 is a diagrammatic flow chart for an exemplary computer program product 620 that provides computer readable media having encoded instructions for executing a method (block 621), wherein the method may include acquiring estimated location parameters for a particular telecommunication device relative to a target body region of a user (block 622); determining whether the particular telecommunication device is in an active operation mode that generates or is predicted to generate electromagnetic irradiation above a predetermined intrusion level (block 623); and responsive to confirmation of the determined active operation mode, implementing remedial action to minimize the electromagnetic irradiation of the target body region (block 624).

Further possible method features to minimize electromagnetic irradiation may include implementing automatic or programmed consequential remedial action with respect to exposure of the target body region to attenuated electromagnetic emissions received from the particular telecommunication device (block 626), and implementing user-selective remedial action with respect to exposure of the target body region to attenuated electromagnetic emissions received from the particular telecommunication device (block 628).

Other exemplary aspects may include communicating an output identifier indicative of currently and/or cumulatively generated radiation emissions above the predetermined intrusion level (block 627). Further possible process features may include establishing the predetermined intrusion level based on a type of target body region to be protected from excessive electromagnetic emissions (block 631). In some instances an exemplary process feature may include establishing the predetermined intrusion level based on a type of implanted or attached or user-related body accessory device to be protected from excessive electromagnetic emissions (block 632). A further possible aspect may include establishing the predetermined intrusion level based on a type or category of user to be protected from excessive electromagnetic emissions (block 633).

Figure 14:
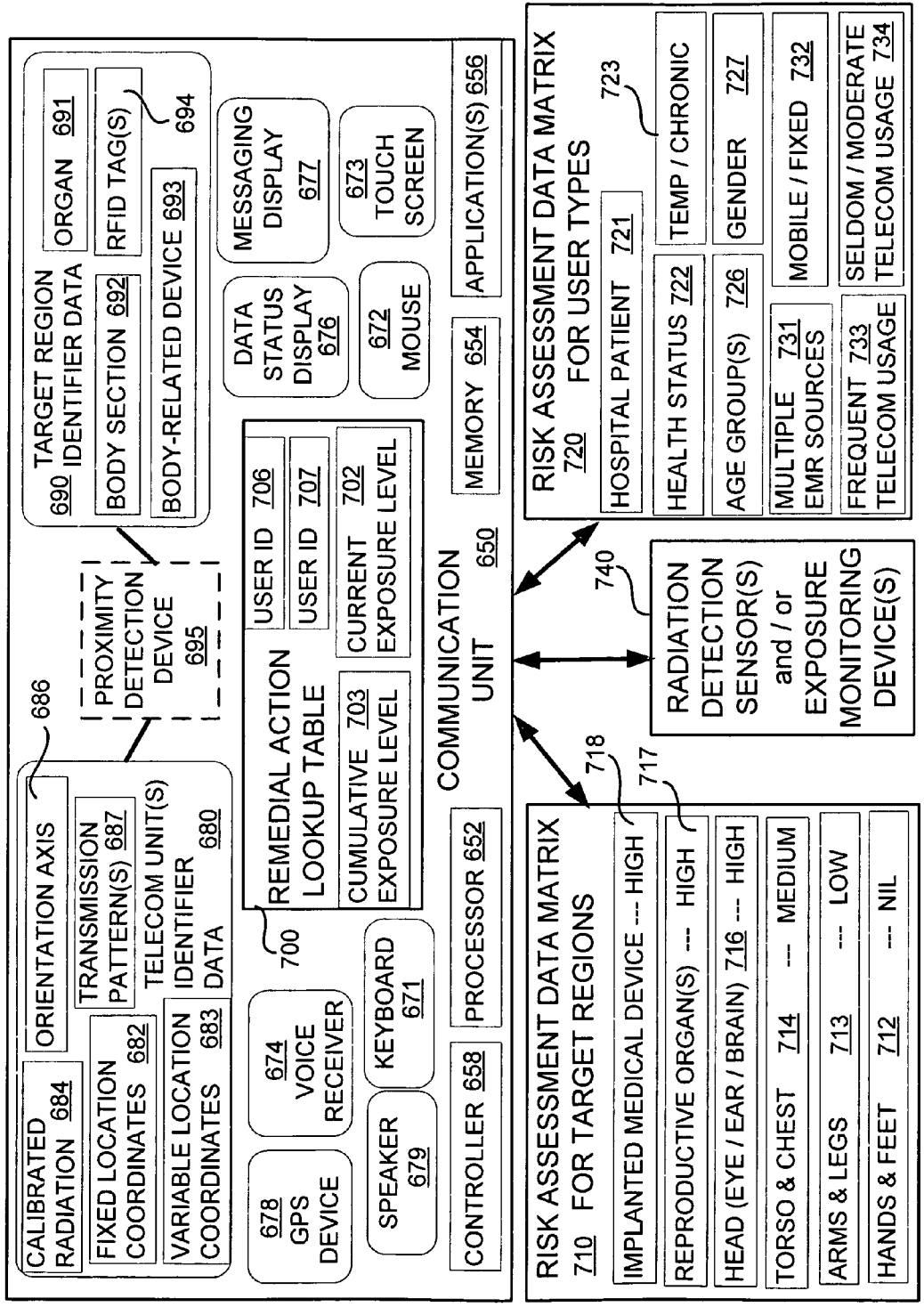
FIG. 14 is a schematic block system diagram for exemplary irradiation protection embodiment features.

Referring to the schematic block diagram of FIG. 14, an exemplary system embodiment for irradiation protection may include communication unit 650 having processor 652, memory 654, one or more program applications 656, and controller 658. The communication unit 650 may be a separate unit or may be incorporated as part of a user's telecom device that generates EMR. Various types of user interfaces may be incorporated in or operably coupled with the communication unit 650 including but not limited to keyboard 671, mouse 672, touch screen 673, voice receiver 674, data/status display 676, messaging display 677, GPS device 678, and speaker 779 to facilitate interactive communications by one or more users associated with the communication module 650.

Various types of updated informational data may be maintained to be accessible to the communication unit 650 including telecom unit(s) identifier data 680, target region identifier data 690, and remedial action lookup table 700. Exemplary telecom unit identifier data 680 may include fixed location coordinates 682, variable location coordinates 683, calibrated radiation 684, orientation axis 686, and transmission pattern(s) 687. Exemplary target region identifier data 690 may include a body organ 691, body section 692, body-related device 693, and one or more radio frequency identification (RFID) tags 694. The exemplary remedial action lookup table may include current exposure level 702, cumulative exposure level 703, first user ID 706, and second user ID 707.

An integral or remote detection module 695 may be operably connected with the target region identifier module 690 and with the telecom location module 680 to enable determination of a separation distance between a particular telecommunication unit and a target body region.

Some exemplary embodiment features may provide a transmission link between the communication unit 650 and as least one radiation detection sensor (see 740) adapted to detect attenuated radiation emissions generated from a telecom unit. Other exemplary embodiment features may provide a transmission link between the communication unit 650 and at least one exposure monitoring device (see 740) adapted to monitor irradiation exposure of a targeted body region.

As illustrated in FIG. 14, the communication unit 650 in some system embodiments may be operably connected with a risk assessment data matrix for target regions 710 wherein some types of bodily-related target regions are deemed to be more vulnerable to electromagnetic irradiation than others. For example, hands and feet may be designated as "nil" risk 712; arms and legs may be designated as "low" risk 713; and torso and chest may be designated as "medium" risk 714. In contrast, sections of the head (e.g., eye, ear, brain) may be designated as "high" risk 716; and reproductive organs may be designated as "high" risk 717. As a further example, a target body region that includes an implanted medical device may be designated as "high" risk 718.

The communication unit 650 in other system embodiments may be operably connected with a risk assessment data matrix for user types 720 wherein some types or categories of people are deemed to be more vulnerable to electromagnetic irradiation than others. For example, different levels of risk assessment may be assigned to a person classified as a hospital patient 721, or a person with a particular health status 722 (e.g, temporary illness or chronic disease 723). As a further example, different levels of risk assessment may be assigned based on one or more age groups 726 or a person's gender 727.

In some situations a different level of risk assessment may be assigned to a person living or working in a place subject to multiple EMR radiation sources 731. Whether the radiation generating device is either mobile or fixed 732 may be a factor in determining an EMR risk assessment. A person in a category of "frequent telecom usage" 733 may be assessed at a higher risk for excessive irradiation exposure than a person in a category of "seldom/moderate telecom usage" 734.

Depending on the circumstances, the various system components including communication unit 650, telecom unit identifier data 680, target region identifier data 690, proximity detection device 695, remedial action lookup table 700, risk assessment data matrices 710, 720 and radiation detection sensors & exposure monitoring devices 740 may be incorporated as part of a user's telecommunication device and/or located externally (e.g., remotely) from such telecommunication device. In some instances certain components may be located at a facility associated with providing irradiation protection services, and/or located in a vehicle or residence or building or workplace of the user. Other locations are possible, and various types of communication links may be provided including but not limited to wireless, cable, satellite, Internet, public networks, private networks, and the like.

It will be further understood from the various embodiment features disclosed herein that certain exemplary data processing functions may be provided by a unitary communication unit 650, and other specified exemplary processing functions may be carried out by separate computerized processing modules.

It will also be understood that the exemplary system embodiments disclosed herein for facilitating irradiation protection for a specified target body region may include data record means (e.g, priority tables 310, 365, identifier data 690, risk assessment data matrix 710) for identifying the specified target body region of a user that is proximate to a particular communication device capable of generating electromagnetic emissions that subject the specified target body region to irradiation exposure; monitoring and/or detection means (e.g., radiation monitors and/or sensors 260, sensors and/or devices 740) for establishing whether such irradiation exposure does exceed or is predicted to exceed a safety threshold correlated with the specified target body region; and control circuit means (e.g., EMR control module 250, communication unit 650) that is activated based on such established irradiation exposure having a dosage value above the safety threshold, wherein such control circuit means is configured to provide a responsive output based on a possible risk relative to such irradiation exposure.

The high level flow chart of FIG. 15 depicts exemplary embodiment features 800 regarding a method of facilitating irradiation protection for a specified target body region (block 801), wherein the method may include identifying the specified target body region of a user that is proximate to a particular communication device capable of generating electromagnetic emissions that subject the specified target body region to irradiation exposure (block 802); establishing whether such irradiation exposure does exceed or is predicted to exceed a safety threshold correlated with the specified target body region (block 803); and if such irradiation exposure has a dosage value above the safety threshold, providing a responsive output based on a possible risk relative to such irradiation exposure (block 804). Another possible feature may include enabling a user to choose the safety threshold correlated with the specified target body region (block 806).

Additional possible process features may include establishing an automatic or programmed safety threshold that is correlated with the specified target body region (block 807), and enabling a user to choose the specified target body region correlated with the safety threshold (block 808). In some instance exemplary embodiment features may include sending the responsive output to a base station or cell tower or service provider or network node or other off-device destination (block 811). Other possible features may include sending the responsive output to a third party for monitoring, and/or record keeping, and/or decision making regarding possible remedial action (block 812).

Also depicted in FIG. 15 are exemplary aspects that include sending the responsive output to one or more of the following types of third party: parent, family member, friend, insurance entity, physician, nurse, health care entity (block 813). Further possible aspects may include sending the responsive output to the particular communication device, wherein the particular device suggests to the user a time limit for a call and/or a change in body location relative to the particular communication device and/or a change in orientation of the particular communication device (block 814).

Figure 16:
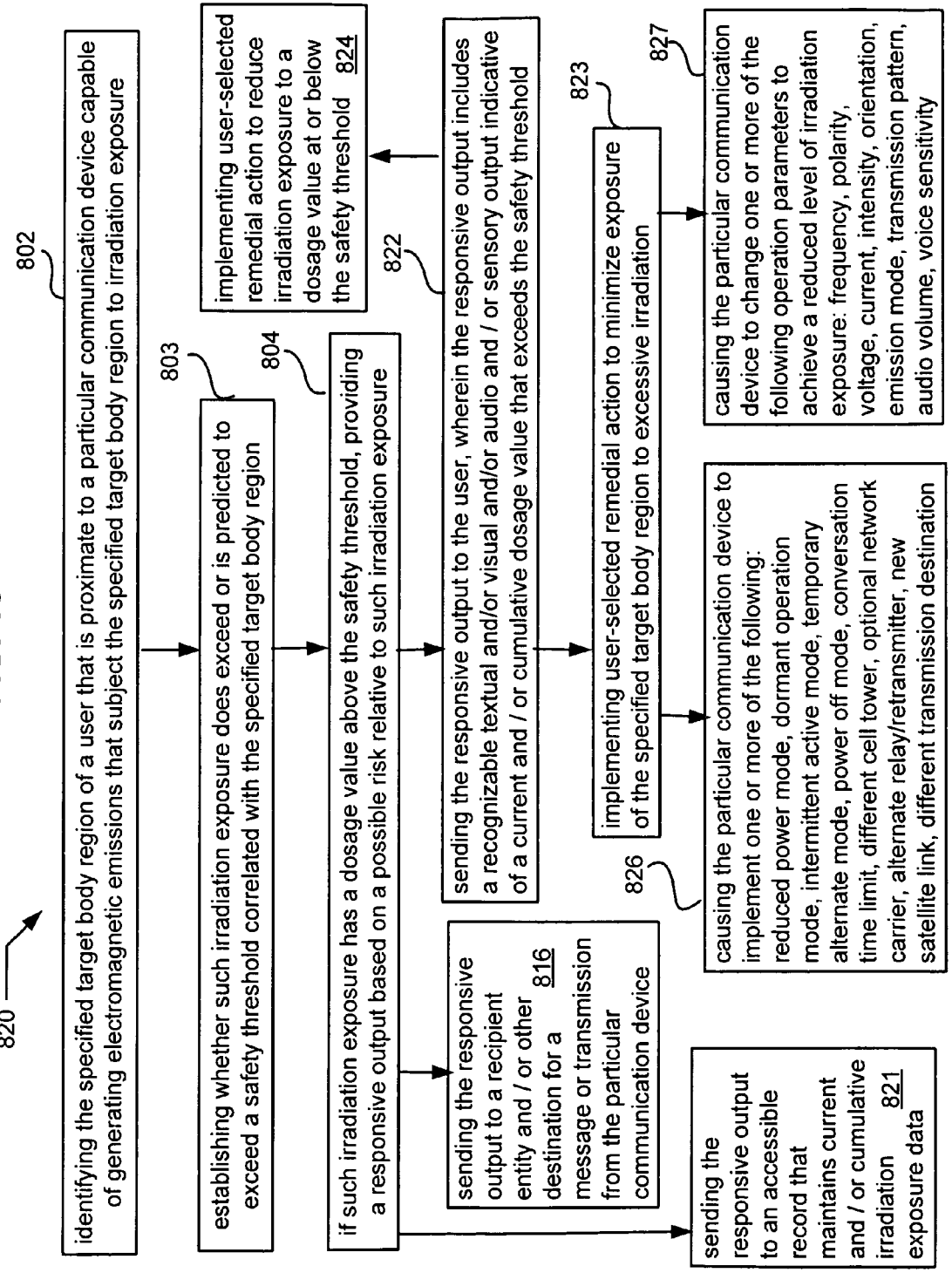
FIGS. 16-22 are detailed flow charts illustrating further exemplary process aspects regarding irradiation protection.

Referring to the flow chart of FIG. 16, various exemplary embodiment features 820 are depicted including previous described aspects 802, 803, 804 along with sending the responsive output to a recipient entity and/or other destination for a message or transmission from the particular communication device (block 816). Additional exemplary features may include sending the responsive output to an accessible record that maintains current and/or cumulative irradiation exposure data (block 821). Other possible process aspects may include sending the responsive output to the user, wherein the responsive output includes a recognizable textual and/or visual and/or audio and/or sensory output indicative of a current and/or cumulative dosage value that exceeds the safety threshold (block 822).

Additional exemplary aspects may include implementing user-selected remedial action to reduce irradiation exposure to a dosage value at or below the safety threshold (block 824), and in some instances may provide for implementing user-selected remedial action to minimize exposure of the specified target body region to excessive irradiation (block 823). Other process aspects may include causing the particular communication device to implement one or more of the following: reduced power mode, dormant operation mode, intermittent active mode, temporary alternate mode, power off mode, conversation time limit, different cell tower, optional network carrier, alternate relay/retransmitter, new satellite link, different transmission destination (block 826). Further exemplary features may include causing the particular communication device to change one or more of the following operation parameters to achieve a reduced level of irradiation exposure: frequency, polarity, voltage, current, intensity, orientation, emission mode, transmission pattern, audio volume, voice sensitivity (block 827).

Figure 17:
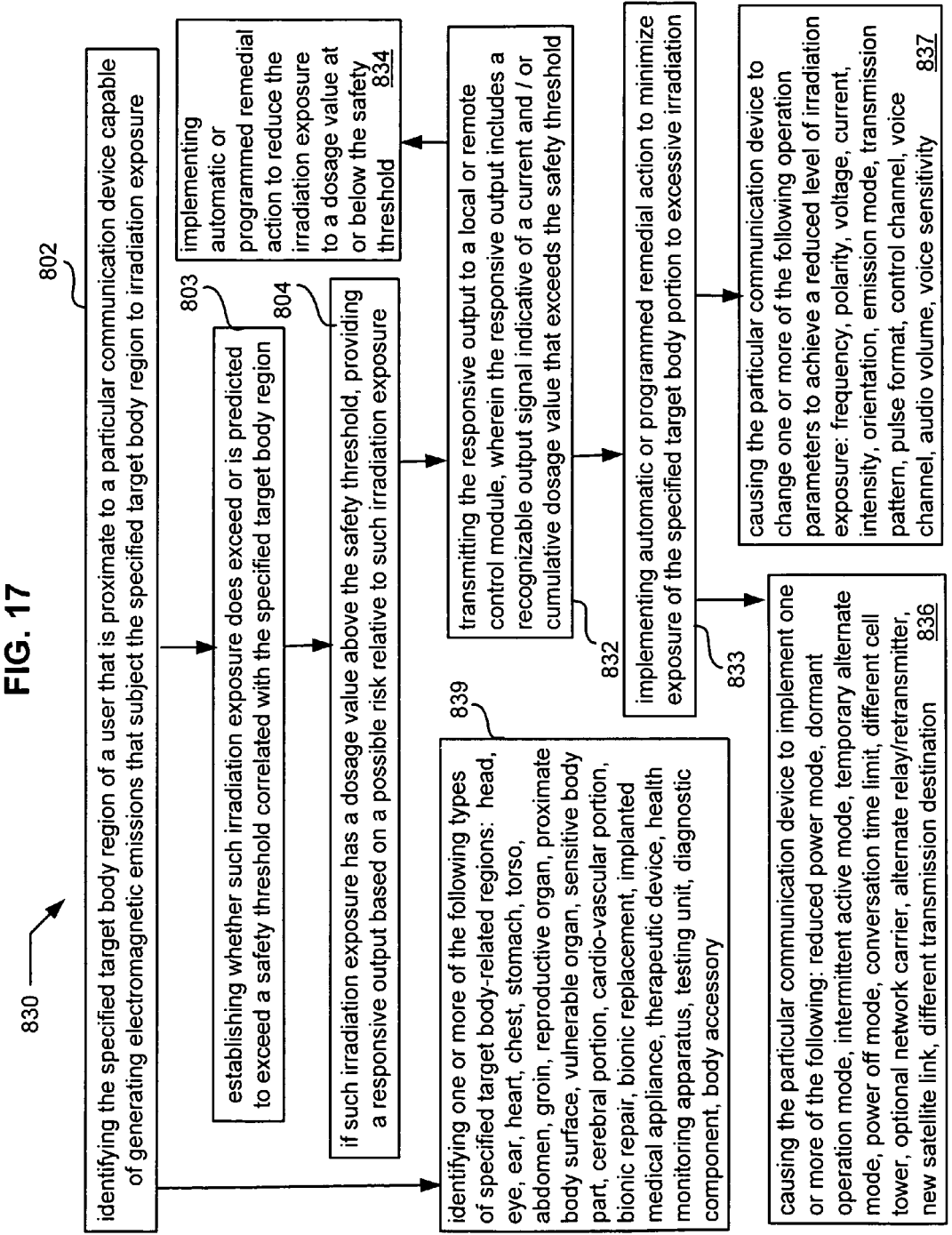

Various exemplary process features 830 are illustrated in the flow chart of FIG. 17 including previous described features 802, 803, 804 in combination with transmitting the responsive output to a local or remote control module, wherein the responsive output includes a recognizable output signal indicative of a current and/or cumulative dosage value that exceeds the safety threshold (block 832). Additional aspects may include implementing automatic or programmed remedial action to reduce the irradiation exposure to a dosage value at or below the safety threshold (block 834). A further possibility may provide for implementing automatic or programmed remedial action to minimize exposure of the specified target body portion to excessive irradiation (block 833).

Some embodiments may include causing the particular communication device to implement one or more of the following: reduced power mode, dormant operation mode, intermittent active mode, temporary alternate mode, power off mode, conversation time limit, different cell tower, optional network carrier, alternate relay/retransmitter, new satellite link, different transmission destination (block 836). Other embodiments may include causing the particular communication device to change one or more of the following operation parameters to achieve a reduced level of irradiation exposure: frequency, polarity, voltage, current, intensity, orientation, emission mode, transmission pattern, pulse format, control channel, voice channel, audio volume, voice sensitivity (block 837).

Additional exemplary aspects shown in FIG. 17 regarding target body regions may include identifying one or more of the following types of specified target body-related regions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory (block 839).

Figure 18:
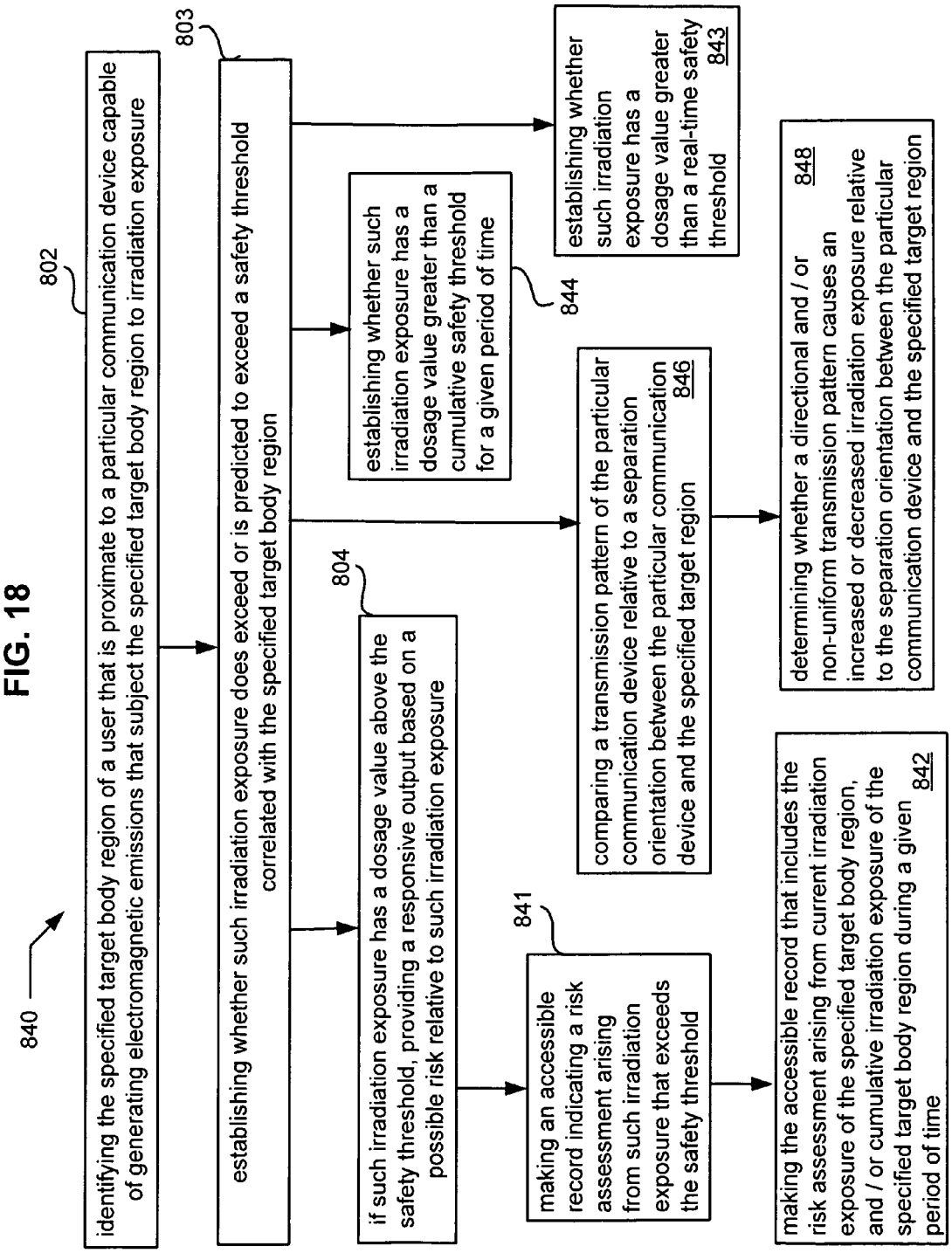

The flow chart of FIG. 18 depicts various exemplary features 840 including previously described features 802, 803, 804 along with making an accessible record indicating a risk assessment arising from such irradiation exposure that exceeds the safety threshold (block 841). Related possibilities may include making the accessible record that includes the risk assessment arising from current irradiation exposure of the specified target body region, and/or cumulative irradiation exposure of the specified target body region during a given period of time (block 842). Further aspects may include establishing whether such irradiation exposure has a dosage value greater than a real-time safety threshold (block 843), and in some instance may further include establishing whether such irradiation exposure has a dosage value greater than a cumulative safety threshold for a given period of time (block 844).

Additional exemplary aspects may include comparing a transmission pattern of the particular communication device relative to a separation orientation between the particular communication device and the specified target region (block 846). Related possible aspects may include determining whether a directional and/or non-uniform transmission pattern causes an increased or decreased irradiation exposure relative to the separation orientation between the particular communication device and the specified target region (block 848).

Figure 19:
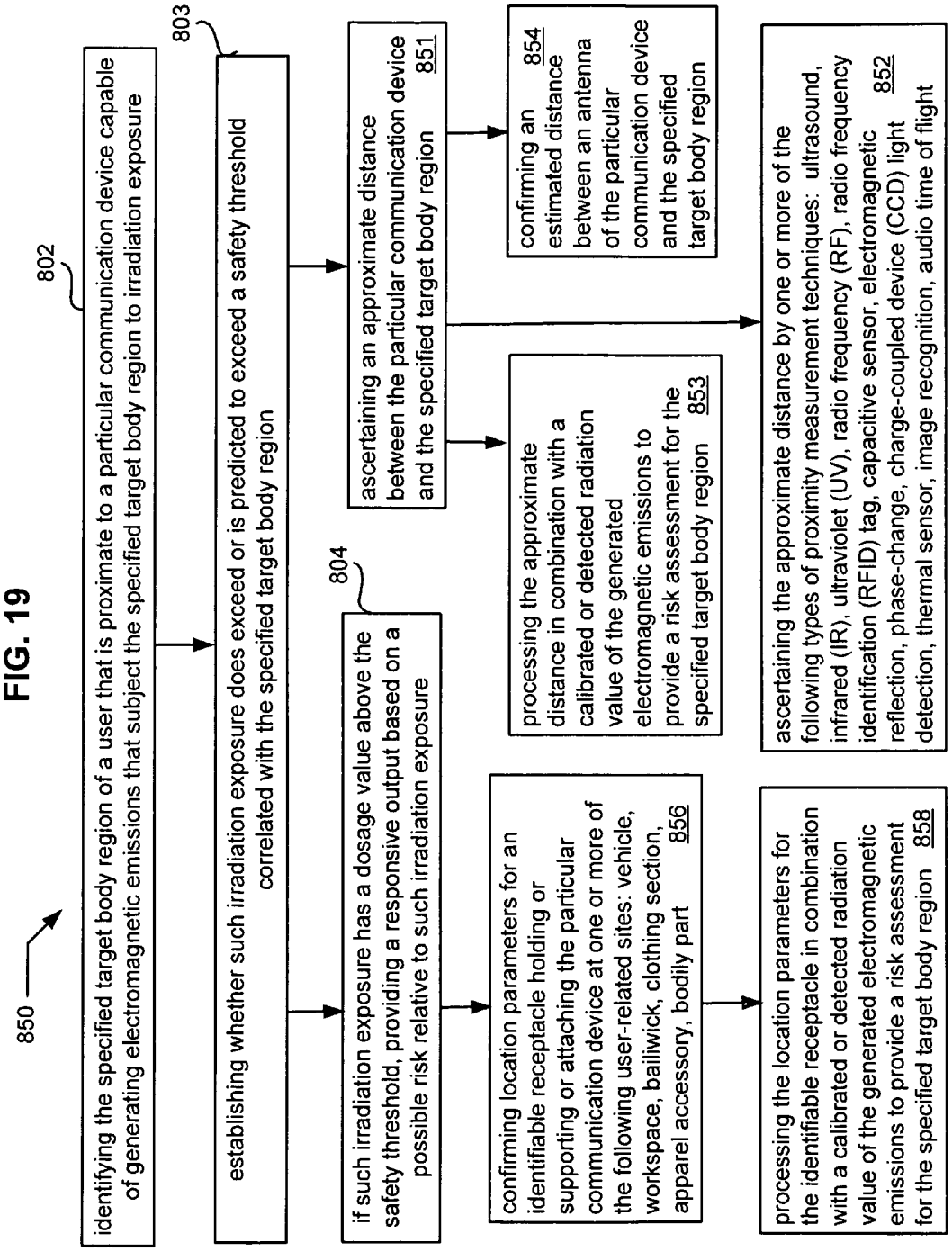

Referring to the exemplary process features 850 shown in the flow chart of FIG. 19, some embodiments may include previously describe aspects 802, 803, 804 in combination with ascertaining an approximate distance between the particular communication device and the specified target body region (block 851). Related process features may include ascertaining the approximate distance by one or more of the following types of proximity measurement techniques: ultrasound, infrared (IR), ultraviolet (UV), radio frequency (RF), radio frequency identification (RFID) tag, capacitive sensor, electromagnetic reflection, phase-change, charge-coupled device (CCD) light detection, thermal sensor, image recognition, audio time of flight (block 852).

Further related process aspects may include processing the approximate distance in combination with a calibrated or detected radiation value of the generated electromagnetic emissions to provide a risk assessment for the specified target body region (block 853). Some embodiments may include confirming an estimated distance between an antenna of the particular communication device and the specified target body region (block 854).

In some instances an exemplary embodiment may include confirming location parameters for an identifiable receptacle holding or supporting or attaching the particular communication device at one or more of the following user-related sites: vehicle, workspace, bailiwick, clothing section, apparel accessory, bodily part (block 856). Further exemplary features may include processing the location parameters for the identifiable receptacle in combination with a calibrated or detected radiation value of the generated electromagnetic emissions to provide a risk assessment for the specified target body region (block 858).

Figure 20:
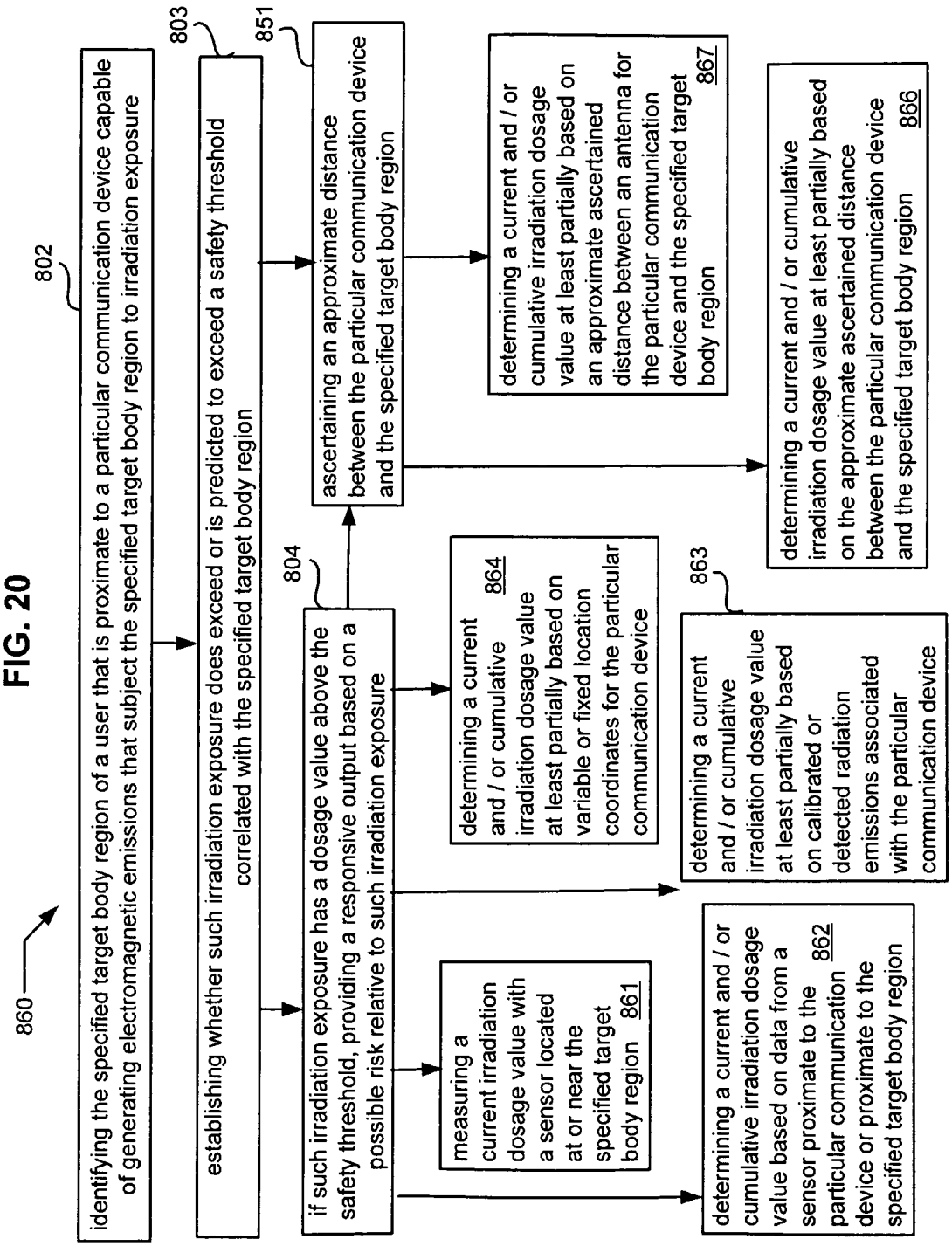

Referring to the flow chart of FIG. 20, possible process features 860 may include previously described aspects 802, 803, 804, 851 as well as determining a current and/or cumulative irradiation dosage value at least partially based on an approximate ascertained distance between the particular communication device and the specified target body region (block 866). In some instances exemplary process features may include determining a current and/or cumulative irradiation dosage value at least partially based on an approximate ascertained distance between an antenna for the particular communication device and the specified target body region (block 867).

Further possible aspects regarding appropriate irradiation exposure dosage values may include measuring a current irradiation dosage value with a sensor located at or near the specified target body region (block 861). Other possible process features may include determining a current and/or cumulative irradiation dosage value based on data from a sensor proximate to the particular communication device or proximate to the specified target body region (block 862).

Some embodiments may include determining a current and/or cumulative irradiation dosage value at least partially based on calibrated or detected radiation emissions associated with the particular communication device (block 863). Other possible embodiment features may include determining a current and/or cumulative irradiation dosage value at least partially based on variable or fixed location coordinates for the particular communication device (block 864). Further related process features (see FIG. 21) may include determining a current and/or cumulative irradiation dosage value at least partially based on an approximate orientation of a transmission pattern of the particular communication device relative to the specified target body region (block 869).

Figure 21:
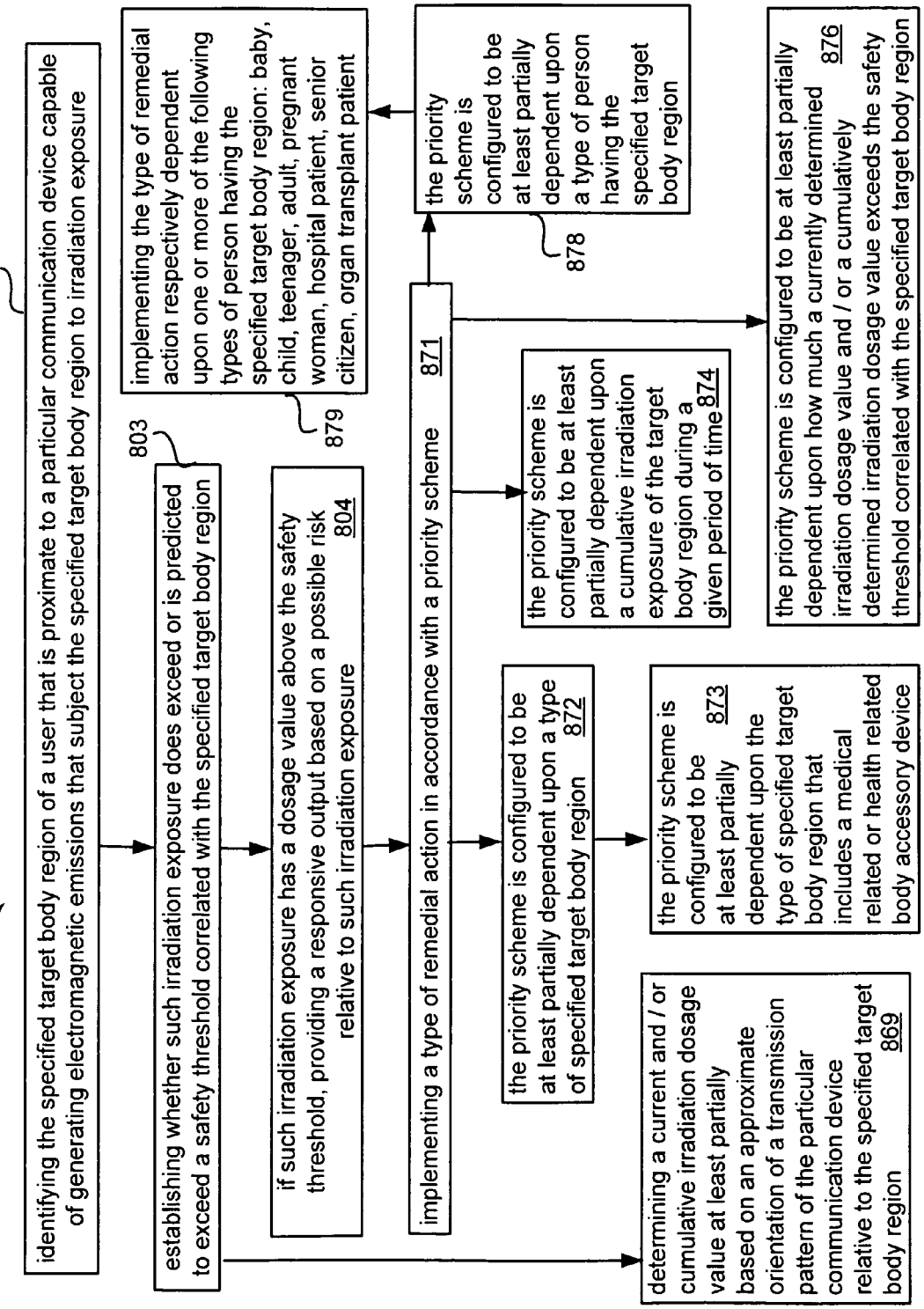

The flow chart of FIG. 21 illustrates additional possible process features 870 including previously described aspects 802, 803, 804 in combination with implementing a type of remedial action accordance with a priority scheme (block 871). Various exemplary priority schemes may be implemented in software and/or circuitry configurations. For example, an exemplary priority scheme may be configured to be implementing a type of remedial action in accordance with a priority scheme configured to be at least partially dependent upon a type of specified target body region (block 872). A related aspect may include implementing the type of remedial action in accordance with the priority scheme configured to be at least partially dependent upon the type of specified target body region that includes a medical related or health related body accessory device (block 873).

Additional embodiment features may include implementing a type of remedial action in accordance with a priority scheme configured to be at least partially dependent upon a cumulative irradiation exposure of the target body region during a given period of time (block 874). In some instances a type of remedial action may be implemented in accordance with a priority scheme configured to be at least partially dependent upon how much a currently determined irradiation dosage value and/or a cumulatively determined irradiation dosage value exceeds the safety threshold correlated with the specified target body region (block 876).

Other possible process aspects may include implementing a type of remedial action accordance with a priority scheme configured to be at least partially dependent upon a type of person having the specified target body region (block 878). For example, an exemplary embodiment may include implementing the type of remedial action respectively dependent upon one or more of the following types of person having the specified target body region: baby, child, teenager, adult, pregnant woman, hospital patient, senior citizen, organ transplant patient (block 879).

Figure 22:
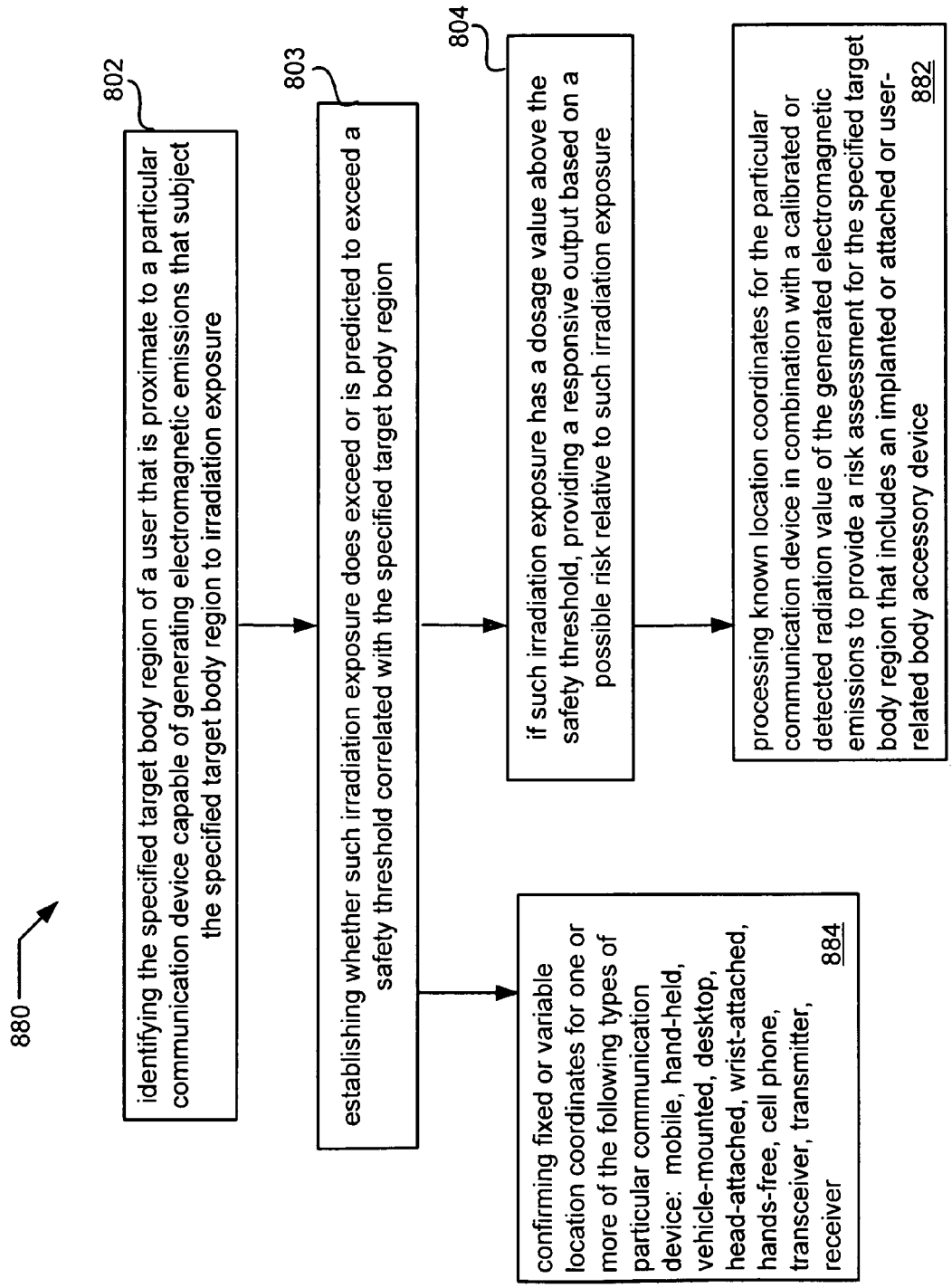

Further exemplary aspects 880 are illustrated in FIG. 22, including previously described aspects 802, 803, 804 as well as processing known location coordinates for the particular communication device in combination with a calibrated or detected radiation value of the generated electromatentic emissions to provide a risk assessment for the specified target body region that includes an implanted or attached or user-related body accessory device (block 882). In some instances, exemplary aspects may include confirming fixed or variable location coordinates for one or more of the following types of particular communication device: mobile, hand-held, vehicle-mounted, desktop, head-attached, wrist-attached, hands-free, cell phone, transceiver, transmitter, receiver (block 884).

Figure 23:
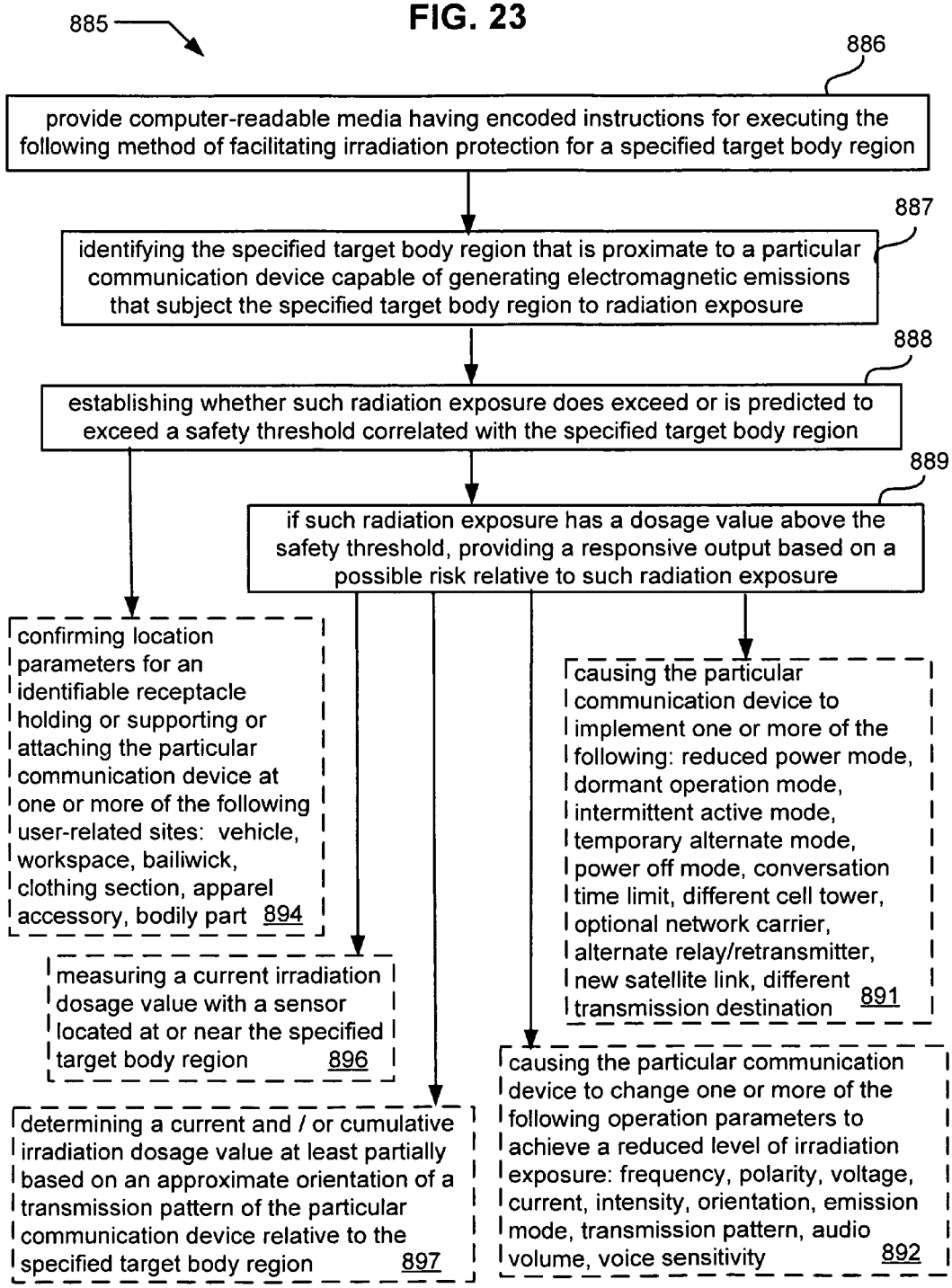
FIG. 23 is a diagrammatic flow chart for other exemplary computer readable media embodiment features.

Exemplary computer program product features 885 depicted in FIG. 23 may include providing computer-readable media having encoded instructions for executing a method of facilitating irradiation protection for a specified target body region (block 886), wherein a possible method may include identifying the specified target body region that is proximate to a particular communication device capable of generating electromagnetic emissions that subject the specified target body region to radiation exposure (block 887), and establishing whether such radiation exposure does exceed or is predicted to exceed a safety threshold correlated with the specified target body region (block 888). Some exemplary embodiments may further include if such radiation exposure has a dosage value above the safety threshold, providing a responsive output based on a possible risk relative to such radiation exposure (block 889).

Other exemplary programmed process features regarding remedial action may include causing the particular communication device to implement one or more of the following: reduced power mode, dormant operation mode, intermittent active mode, temporary alternate mode, power off mode, conversation time limit, different cell tower, optional network carrier, alternate relay/retransmitter, new satellite link, different transmission destination (block 891). Further possible programmed process features regarding remedial action may include causing the particular communication device to change one or more of the following operation parameters to achieve a reduced level of radiation: frequency, polarity, voltage, current, intensity, orientation, emission mode, transmission pattern, audio volume, voice sensitivity (block 892).

Some embodiments may include programmed process features that include confirming location parameters for an identifiable receptacle holding or supporting or attaching the particular communication device at one or more of the following user-related sites: vehicle, workspace, bailiwick, clothing section, apparel accessory, bodily part (block 894). Additional possible programmed process features may include measuring a current irradiation dosage value with a sensor located at or near the specified target body region (block 896). Other exemplary programmed process aspects may include determining a current and/or cumulative irradiation dosage value at least partially based on an approximate orientation of a transmission pattern of the particular communication device relative to the specified target body region (block 897).

Figure 24:
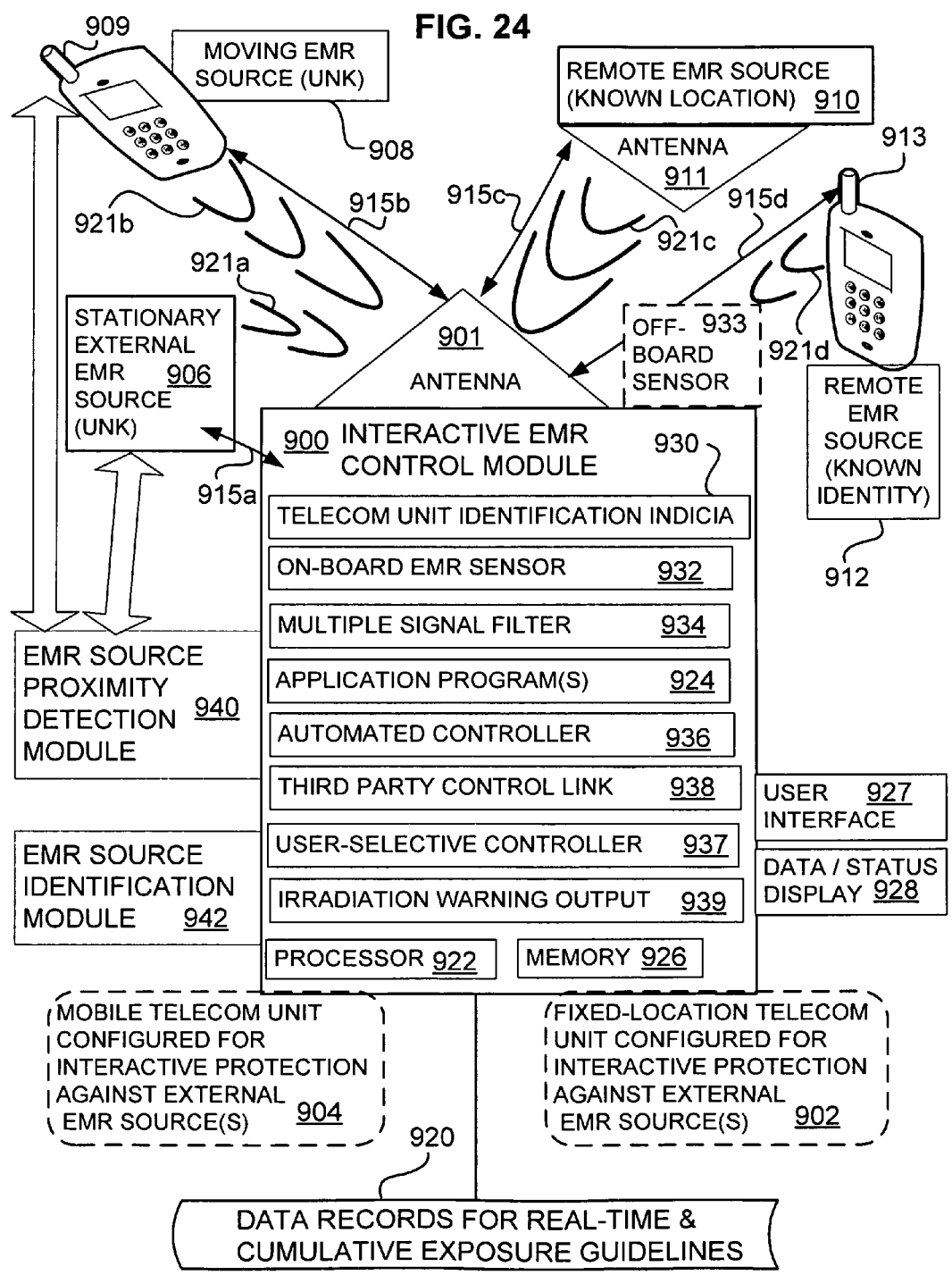
FIG. 24 is a schematic block diagram depicting exemplary interaction aspects regarding a source of electromagnetic radiation (EMR) emissions.

Referring to the schematic block diagram of FIG. 24, an illustrative system embodiment may include interactive EMR control module 900 including processor 922, one or more application programs 924, memory 926, user interface 927, and data/status display 928. The EMR control module 900 may be incorporated with a fixed-location telecommunication unit 902 configured for interactive protection against one or more external EMR sources, or in some instances incorporated with a mobile telecommunication unit 904 configured for interactive protection against one or more external EMR sources.

Illustrated examples of external EMR sources depicted in FIG. 24 include an unknown stationary external EMR source 906 generating emissions 921*a*, an unknown moving EMR source 908 (e.g., cellphone) generating emissions 921*b*, a remote EMR source 910 at a known location that generates emissions 921*c*, and a remote EMR source 912 of known identity that generates emissions 921*d*. The interactive EMR control module 900 may have a direct communication link 915*a* with stationary EMR source 906. The interactive EMR control module 900 may also include antenna 901 that enables a wireless communication link 915*b* with moving EMR source 908 via its antenna 909, and enables another wireless communication link 915*c* with remote EMR source 910 via its antenna 911, and enables a further wireless communication link with remote EMR source 912 via an associated cellphone antenna 913.

It will be understood the illustrated embodiment features of FIG. 24 enable selective transmission of communication signals and/or messages with one or more EMR sources 906, 908, 910, 912 regarding undesirable or interfering irradiation exposure at a user-related site associated with the interactive EMR control module 900. Such irradiation exposure can be detected by an on-board EMR sensor 932 of the EMR control module 900, and in some instances by an off-board sensor 933 that may be located in closer proximity to a protected user-related target area.

It will be understood that the user-related sites and/or target areas disclosed herein are for purposes of illustration only. Various other types of user-related fixed and/or user-related mobile target areas may be protected against undesirable and/or interfering EMR emissions in accordance with the principles and practices set forth herein.

A possible request for remedial action to alleviate or otherwise compensate for the detected exposure at the user-related site may be dependent on a safety threshold or intrusion level that is correlated with a protected user-related site. Such safety threshold and intrusion level information may be maintained in data records for real-time and cumulative exposure guidelines 920 operably linked to the EMR control module 900.

Some remedial action requests may occur automatically (e.g., pursuant to default guidelines), and other remedial action requests may be determined on a case-by-case basis. In that regard, the EMR control module 900 may be configured with circuitry or other processing components for management of irradiation data, wherein the EMR control module 900 may include telecom unit identification data 930, multiple signal filter 934 to differentiate between different electromagnetic emissions, automated controller 936, user-selective controller 937, a third party control link 938, and an irradiation warning output 939.

Proper identification of the various EMR sources 906, 908, 910, 912 for purposes of evaluation and follow-up communication requests may be facilitated by additional system components operably coupled with the EMR control module 900, including for example EMR source proximity detection module 940, and in some instances including an EMR source identification module 942 that may be linked to applicable websites and/or pertinent database records.

Figure 25:
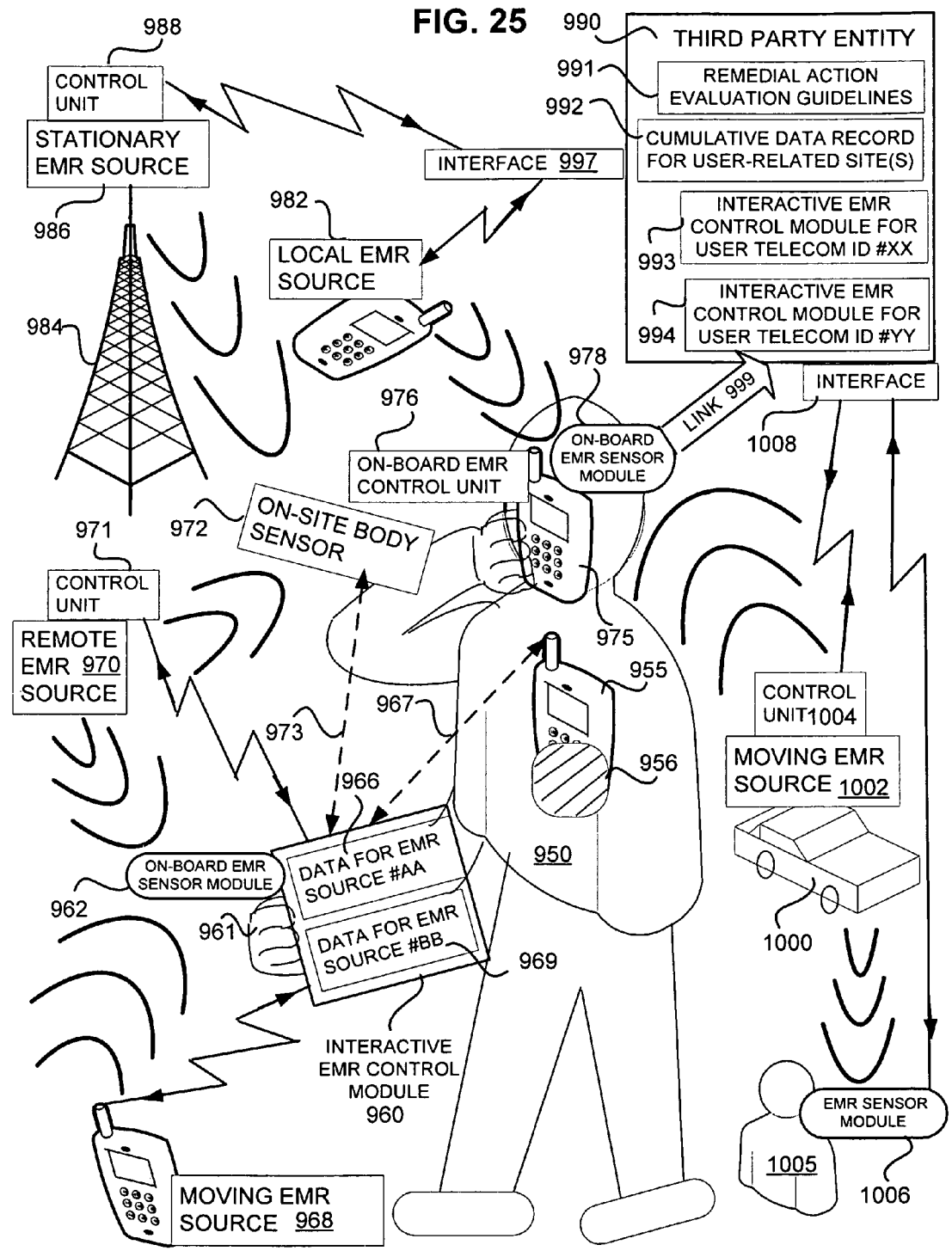
FIG. 25 is a schematic block diagram depicting further exemplary embodiment features regarding alleviation of irradiation exposure.

Referring to the schematic block diagram of FIG. 25, an illustrative system embodiment for a particular user 950 that constitutes a user-related site may include a handheld 961 mobile interactive EMR control module 960 including an on-board EMR sensor module 961 for detection of emissions from one or more external sources such as from moving EMR source 968 (e.g., cellphone) and from a remote EMR source 970. The interactive EMR control module 960 may also be linked 973 with an on-site body sensor 972 closely proximate to a target bodily portion, wherein the on-site body sensor 972 can detect emissions from various sources including remote EMR source 970 as well as from a stationary EMR source 986 such as a network transmission tower 984.

Actual real-time and/or cumulative irradiation exposure levels may be collected and stored by the interactive EMR control module 960 for each different emission source such as data for EMR source #AA 966 and data for EMR source #BB 969. Another possible link 967 may be provided from the interactive EMR control module 960 to a user cell phone device 955 (e.g., held by pocket 956 or otherwise affixed to apparel) for additional retrieval and/or management of irradation exposure levels. Requests for possible remedial action (e.g., alleviation, compensation, offsetting consideration) may be transmitted to control units 971, 988 respectively associated with remote EMR source 970 and stationary EMR source 986.

Some user cellphone devices 975 for a user-related site may include an on-board EMR control unit 976 as well as an on-board EMR sensor module 978 that monitors emissions from one or more sources such as local EMR source 982 and moving EMR source 1002 (e.g., vehicle 1000). An evaluation process regarding possible irradiation remedial action may be accomplished by the on-board control unit 976 for user cellphone device 975, or in some instances via communication link 999 by an evaluation process conducted by a third party entity 990. For example, such a third party entity 990 may have access to a set of remedial action evaluation guidelines 991 as well as access to cumulative data records 992 that are respectively applicable for one or more user-related sites (e.g., 950, 1005) which are subject to undesirable or interfering EMR exposure.

The third party entity 990 may in some instances provide evaluation and management services regarding irradiation exposure for multiple user-related sites. For example, the third party entity 990 may provide an interactive EMR control module 993 for a particular user-related site 950 having telecom unit ID #XX, wherein the third party entity 990 communicates via interface 997 in order to request and/or obtain remedial action regarding emissions from stationary EMR source 986 as well as remedial action regarding emissions from local EMR source 982, and in some instances remedial action regarding emissions from moving EMR source 1002.

As a further example, the third party entity 990 may provide another interactive EMR control module 994 for a user-related site 1005 having telecom unit ID #YY, wherein the third party entity 990 communicates via interface 1008 with a control unit 10004 in order to request and/or obtain remedial action regarding emissions from the moving EMR source 1002 (e.g., vehicle 1000). An EMR sensor module 1006 may be configured to send monitored irradiation dosage levels via interface 1008 to the third party entity 990, and in some instances configured to implement remedial action pursuant to emission management signals from the interactive EMR control module 994.

Referring to the schematic block diagram of FIG. 26, a mobile user-related site (e.g., passenger vehicle, land conveyance, watergoing vessel, airborne transport, etc.) may carry driver 1030 and passenger 1031 who may both be subjected to irradiation dosage exposure from a cellphone 1023 fixedly or removably mounted in a vehicle transceiver support holder 1027. Additional exposure risks to driver 1030 and passenger 1031 may arise from radiation emissions generated from stationary external EMR source #CC 1021 and from local EMR source #DD 1022. A target body sensor 1033 may be located proximate to driver 1030 or located in a default position proximate to both driver 1030 and passenger 1031.

The embodiment features of FIG. 26 may include an interactive EMR control module operably coupled through link 1026 via vehicle transceiver support holder 1027 to an updatable data record indicating real-time vehicle location parameters 1028 as determined by GPS unit 1029. The interactive EMR control module may also be operably connected via communication channel 1062 to receive irradiation inputs from the target body sensor 1033, and may also be operably connected via communication link 1063 to a cumulative radiation record 1065 for various users associated with the vehicle.

Typical user types having their own individual radiation records may include driver owner 1069, driver teenager 1068, passenger #1 1067, and passenger #2 1066. Irradiation protection limits that are correlated with the cumulative radiation record 1065 by the interactive EMR control module 1025 may be provided for the driver owner 1056, driver teenager 1057, passenger #1 1058, and passenger #2 1059. In some instances an irradiation protection limit that defines a default standard 1055 may be provided based on applicable regulatory or medical or safety guidelines. It will be understood that EMR exposure data may be obtained from various types of irradiation detection sensors 1035 that may be incorporated with or linked to the interactive EMR control module 1025.

Additional components for processing irradiation exposure data and implementing possible remedial action by the interactive EMR control module 1025 may include processor 1040, one or more application programs 1041, user interface 1042, and data/status display 1043. Other components may include EMR source proximity detection module 1045, EMR source identification module 1046, and warning indicator 1048. Further examples of pertinent data records may include a data table for internal vehicle EMR source 1050, data table for EMR source #CC 1052, and data table for EMR source #DD 1054.

It will be understood that irradiation exposure at a user-related site can be caused by various types of electromagnetic emission sources. In that regard FIGS. 27-28 depict examples of information that could be maintained in an accessible data table of EMR sources for evaluation of irradiation exposure as well as determining possible responsive remedial action.

Referring to FIG. 27, the representative data table may include multiple data categories such as EMR identity 1080, EMR source locale 1081, contact address 1082 for a particular emission source, type of device 1083 generating the emissions, an estimated irradiation risk 1084, an emission time variation 1086, requested remedial action 1087, and possible reciprocation terms 1088.

For example, data entries regarding a particular user-related site may include an EMR source identified as an "entry security scanner" 1090 located at "federal office building" 1091 having a contact address "scan #123@ct.com" 1092 with regard to an "x-ray & metal detector" 1093 that creates an estimated "low level" 1094 irradiation risk during a "weekdays 9 AM-6 PM" 1095 time period. Further data entries for the particular user-related site may include an EMR source identified as "clinical treatment apparatus" 1099 located at "college medical center" 1101 having a contact address "safety@umd.edu" 1102 with regard to a "radiation therapy units" 1103 that create an estimated "high level" 1104 irradiation risk during "random" 1105 time periods.

As further examples, other data entries regarding the particular user-related site may include an EMR source identified as a "hi-volume computer system" 1109 located at "central data center" 1111 having a contact address "dept web page" 1112 with regard to "satellite microwave units" 1113 that create "variable levels" 1114 of irradiation risk during "mega project usage" 1115 time periods. Other data entries for the particular user-related site may include an EMR source identified as "cellphone base station" 1118 located at "nearby tower" 1119 having a contact address "1-888-445-5444" 1120 with regard to a "high power antenna" 1121 that creates "variable levels" 1122 of irradiation risk during "peak daytime hours" 1123.

As additional examples, other data entries regarding the particular user-related site may include an EMR source identified as "nearby activated phones" 1126 located at "WiFi public area" 1127 having a contact address at "WiFi.com" 1128 with regard to a "WiFi relay unit" 1129 that creates "variable levels" 1130 of irradiation risk during "random" 1131 time periods. Some data entries for the particular user-related site may include an EMR source identified as "unknown EMR sources" 1134 located at "medical waiting rooms" 1135 having a contact address "hospital hot line 1-800-##" 1136 with regard to "multiple treatment devices" 1137 that create "unknown" 1138 irradiation risks during "all hours 24/7" 1139.

As part of an interactive protocol regarding possible irradiation risk management for a particular user-related site, additional illustrative data entries for objectionable emissions from an "entry security scanner" 1090 may include "bypass scanner per keycard" 1096 as possible remedial action pursuant to reciprocation "fees assessed to law firm attys & staff" 1097. Further illustrative data entries for objectionable emissions from "clinical treatment apparatus" 1099 may include "temporary dormant mode" 1106 as a possible remedial action based on a reciprocation requirement to "become health plan member" 1107. Some illustrative data entries for objectionable emissions from a "hi-volume computer system" 1109 may include "remote temp office usage" 1116 as possible remedial action based on a user reciprocation agreement to "pay extra health plan fee" 1117.

Other illustrative data entries for objectionable emissions from a "cellphone base station" 1118 may include "no EMR change required" 1124 as a possible remedial action wherein a reciprocation term allows the user to "received discount cellphone service" 1125. Additional illustrative data entries for objectionable emissions from "nearby activated phones" 1126 may include "access to low EMR Wi-Fi room" 1132 as a possible remedial action in accordance with a reciprocation requirement for "payment of time-based user fee" 1133. Some illustrative data entries for objectionable emissions from "unknown EMR sources" 1134 may include "no EMR change required" 1140 as a possible remedial action in exchange for a reciprocated "reimbursement of parking fees" 1141.

Referring to FIG. 28, the representative data table may include multiple data categories such as EMR source type 1145, approximate separation distance 1146 from user-related site, identified location 1147 of the EMR source, emission level 148 of the EMR source, a moving or non-moving source 1149, real-time action status 1150 of irradiation exposure, remedial action terms 1151, and cumulative risk status 1152 of user-related site.

For example, data entries for a particular user-related site may include a "known source type #FF" 1153 with an estimated separation distance of "less than two feet" 1154 and an identified location in a "north/west direction" 1155, and having an emission level that is "sporadic between low & high level" 1156, and wherein such source is deemed to be "moving" 1157. Further data entries for the particular user-related site may include a "known source type #GG" 1160 with an estimated separation distance of "more than two feet" 1161 and an identified location in "an upper office" 1162, and having an emission level that is "low & increasing" 1163, and wherein such source is deemed to be "not moving" 1164.

As further examples, additional data entries for the particular user-related site may include an "unknown source type #HH" 1167 with an estimated separation distance of "more than ten feet" 1168 and an identified location in an "adjacent street" 1169, and having an emission level that is "above user threshold level" 1170, and wherein such source is deemed to be "moving" 1171". Other data entries for the particular user-related site may include an "unknown source type #JJ" 1181 with an estimated separation distance of "about seventy feet" 1175 and an identified location at "power transmission station on State Street" 1176, and having an emission level that is "high and constant" 1177, and wherein such source is deemed to be "not moving" 1178. More data entries for the particular user-related site may include a "known source type #KK" 1181 without any estimated separation distance "N/A" 1182 and an identified location "high voltage tower" 1183, and having an emission level that is "low & constant" 1184, and wherein such source is deemed to be "not moving" 1185.

As part of an evaluation process regarding an irradiation exposure risk for a particular user-related site, additional illustrative data entries for objectionable emissions from a "known source type #FF" 1153 may include an "ignore" 1158 real-time action status, with a possible "pre-arranged low power mode" 1166 also available. Further illustrative data entries for objectionable emissions from a "known source type #GG" 1160 may include an action status of "send action request to source" 1165 regarding an available "pre-arranged monetary credit" 1166 remedy. Other illustrative data entries for objectionable emissions from an "unknown source #HH" 1167 may include a "transmit warning alarm to user" 1172 real-time action status in view of a remedial entry "not any remedy available" 1173.

Further illustrative data entries for objectionable emissions from an "unknown source #JJ" 1174 may include a "show optional route map to user" 1179 real-time action status based on a remedial entry "no remedial action available" 1180. Additional illustrative data entries for "known source #KK" 1181 may include an "ignore" 1186 real-time action status based on an entry "new request required" 1186 to obtain possible beneficial remedial terms.

In some instances the data table may indicate an updated cumulative risk status based on irradiation dosage exposure from one or more emission sources during a given time period. For example, a possible data entry may indicate "cumulative daily dosage for user Phil already exceeds evaluation guidelines" 1190. As a further example, a possible data entry may indicate "cumulative hourly dosage for user Erin is below evaluation guidelines" 1192. As another example, a possible data entry may indicate "cumulative weekly dosage for this user site is below preferred government standard" 1194.

It will be understood that the informational parameters shown in the data tables of FIGS. 27-28 are for purposes of illustration only, and may be expanded or altered in some embodiments and may be shortened or omitted in other embodiments depending on the circumstances.

As disclosed herein, a system for obtaining responsive action regarding electromagnetic irradiation may include a sensor or monitor device (e.g., 932, 933, 972, 978, 1033) configured for detecting at a user-related site an undesirable or interfering exposure to electromagnetic radiation (EMR) caused by emissions from one or more external sources (e.g., 906, 908, 910, 912, 968, 970, 982, 984, 1004). Another possible system element may include a communication module (e.g. 900, 960, 975) operably coupled to the sensor or monitor device, wherein the communication module is configured for transmitting directly (e.g., 915a, 915c) or indirectly (e.g., 915b, 915d, 999) to the one or more external sources a request for remedial action to alleviate or otherwise compensate for the detected exposure at the user-related site.

Also disclosed herein is an exemplary system of interaction concerning electromagnetic radiation (EMR) which may include a communication interface (e.g., 997, 1008, 1026, 1062) for receiving informational data regarding undesirable or interfering EMR exposure detected at a user-related site (e.g., 950, 1020, 1030), and computerized processing components (e.g., 993, 994, 1040, 1041, 1052, 1054) for evaluating the informational data regarding the EMR exposure in accordance with applicable guidelines (e.g., 991, 992, 1055, 1056) to establish whether or not any remedial action is appropriate. Another possible system feature may include a communication module operably coupled to the computerized processing components and configured to implement remedial action based on the evaluation of the informational data (e.g., see FIGS. 27-28).

Some system embodiments for facilitating responsive action regarding electromagnetic irradiation may include an interface component (e.g., 997, 1008, 1026) for receiving a communication from or on behalf of a user-related site that is subject to irradiation exposure from undesirable or interfering electromagnetic emissions, and data processing module features (e.g., 940, 942, 960, 966, 968, 1025, 1045, 1046) for determining a possible source of the undesirable or interfering electromagnetic emissions. A further system component may include a communication module (e.g., 960, 1025) configured to send a request for remedial action to an entity associated with the possible source.

Further possible system aspects disclosed herein may include system components for obtaining responsive action regarding undesirable or interfering electromagnetic irradiation. In that regard, possible system features may include sensor or monitor devices (e.g., 978) for detecting a level of irradiation exposure at a user-related site, and a communication component (e.g., 999) configured for transmitting empirical data regarding the level of irradiation to a designated entity (e.g., 990) for evaluation. Further possible system features may include computer processing elements (e.g., 993, 994) operably linked to receive the transmitted empirical data and configured for evaluation (e.g., 992, 991) of the level of irradiation, and wherein based on a result of such evaluation the computer processing elements are enabled to request remedial action for implementation (e.g., 971, 988, 1004) by an identified source of the undesirable or interfering electromagnetic emissions.

Referring to the high level flow chart of FIG. 29, an illustrated process embodiment 1200 may provide a method of interaction with a source of electromagnetic emissions (block 1201), including detecting at a user-related site an undesirable or interfering exposure to electromagnetic radiation (EMR) caused by emissions from one or more external sources (block 1202), and transmitting directly or indirectly to the one or more external sources a request for remedial action to alleviate the detected exposure at the user-related site (block 1204). Other possible features may include measuring a level of EMR exposure with a telecommunication device configured to monitor irradiation at or near the user-related site (block 1206). In some instances a related feature may include measuring a level of EMR exposure with a sensor located at or near the user-related site (block 1208).

Additional aspects may include prior to said transmitting, establishing whether such exposure to EMR exceeds or is predicted to exceed a current and/or cumulative threshold correlated with an applicable regulatory standard (block 1211). Other aspects may include prior to the transmitting, establishing whether such exposure to EMR exceeds or is predicted to exceed a current and/or cumulative threshold correlated with the user-related site (block 1212). Additional embodiment features may include prior to the transmitting, establishing whether such exposure to EMR exceeds or is predicted to exceed an intrusion level or safety threshold which is determined by one or more of the following: user selection, program module, radiation sensor, calibrated communication device, user telecommunication device, user health status, body accessory, user medical device, physician recommendation, regulatory standard, network guidelines (block 1213).

As further depicted in FIG. 29, other possible operational features may include providing to the one or more external sources certain self-identifying information regarding the user-related site (block 1216). Some embodiments may include providing to the one or more external sources certain irradiation data indicative of an aspect of the EMR that causes the undesirable or interfering exposure (block 1217). Other possible features may include providing to the external source one or more of the following EMR aspects: intensity, frequency, radiation level, radiation duration, cumulative radiation, directionality, polarization, transmission pattern, time-scheduled radiation, time of occurrence, duration of occurrence after request (block 1218).

Figure 30:
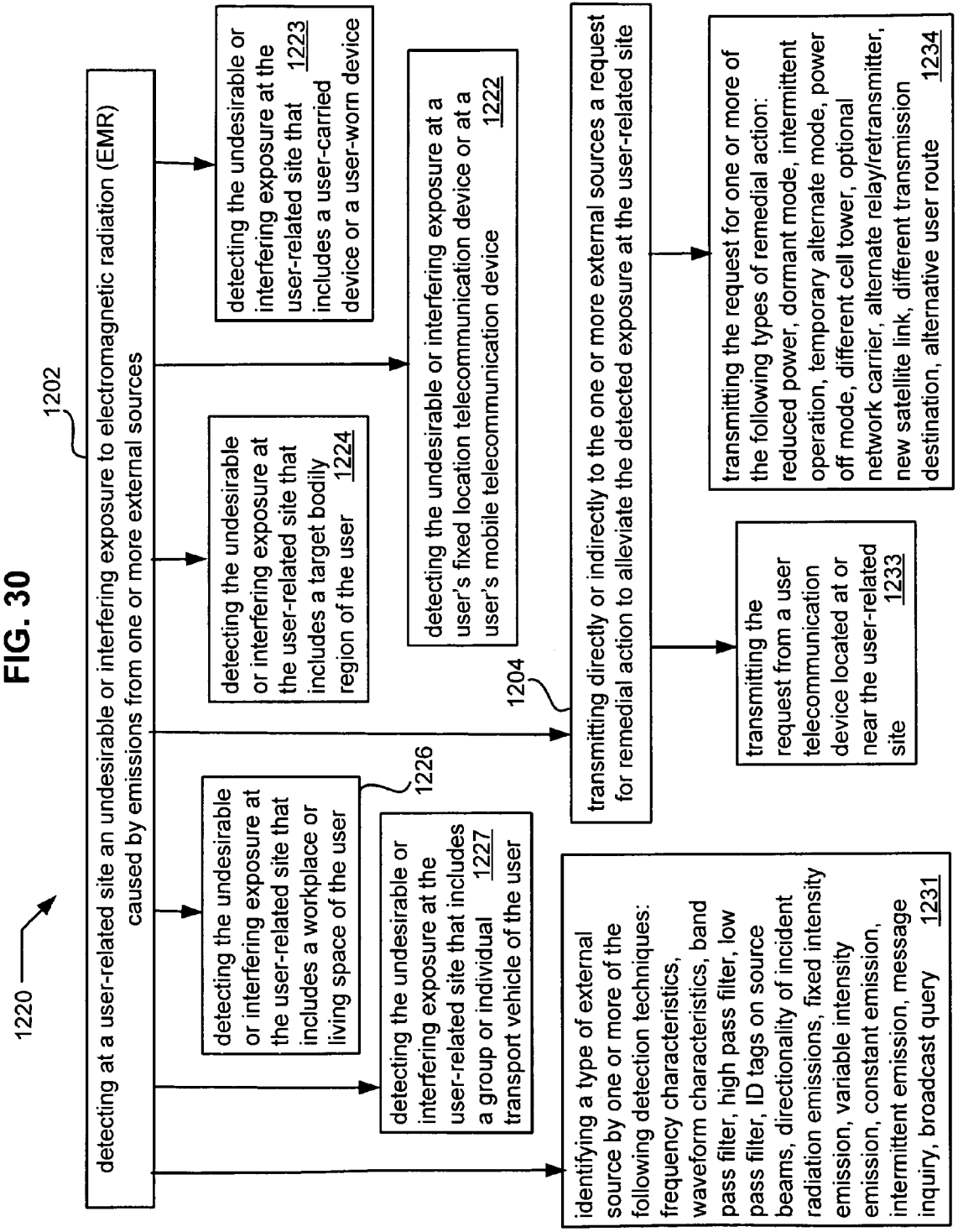
FIGS. 30-33 are detailed flow charts illustrating further possible irradiation protection techniques.

The more detailed flow chart of FIG. 30 illustrates further exemplary embodiment features 1220 including previously described process components 1202, 1204 along with detecting undesirable or interfering exposure at a user's fixed location telecommunication device or at a user's mobile telecommunication device (block 1222). Further illustrated aspects may include detecting the undesirable or interfering exposure at the user-related site that includes a target bodily region of the user (block 1223), or detecting the undesirable or interfering exposure at the user-related site that includes a user-carried device or a user-worn device (block 1224).

Additional process features may include detecting the undesirable or interfering exposure at the user-related site that includes a workplace or living space of the user (block 1226), and in some instances detecting the undesirable or interfering exposure at the user-related site that includes a group or individual transport vehicle of the user (block 1227). Other possible process features may include identifying a type of external source by one or more of the following detection techniques: frequency characteristics, waveform characteristics, band pass filter, high pass filter, low pass filter, ID tags on source beams, directionality of incident radiation emissions, fixed intensity emission, variable intensity emission, constant emission, intermittent emission, message inquiry, broadcast query (block 1231).

Some embodiments may include additional provisions for transmitting the request for remdial action. For example, one possible aspect may include transmitting the request from a user telecommunication device located at or near the user-related site (block 1233). As another example, a further possible aspect may include transmitting the request for one or more of the following types of remedial action: reduced power, dormant mode, intermittent operation, temporary alternate mode, power off mode, different cell tower, optional network carrier, alternate relay/retransmitter, new satellite link, different transmission destination, alternative user route (block 1234).

Figure 31:
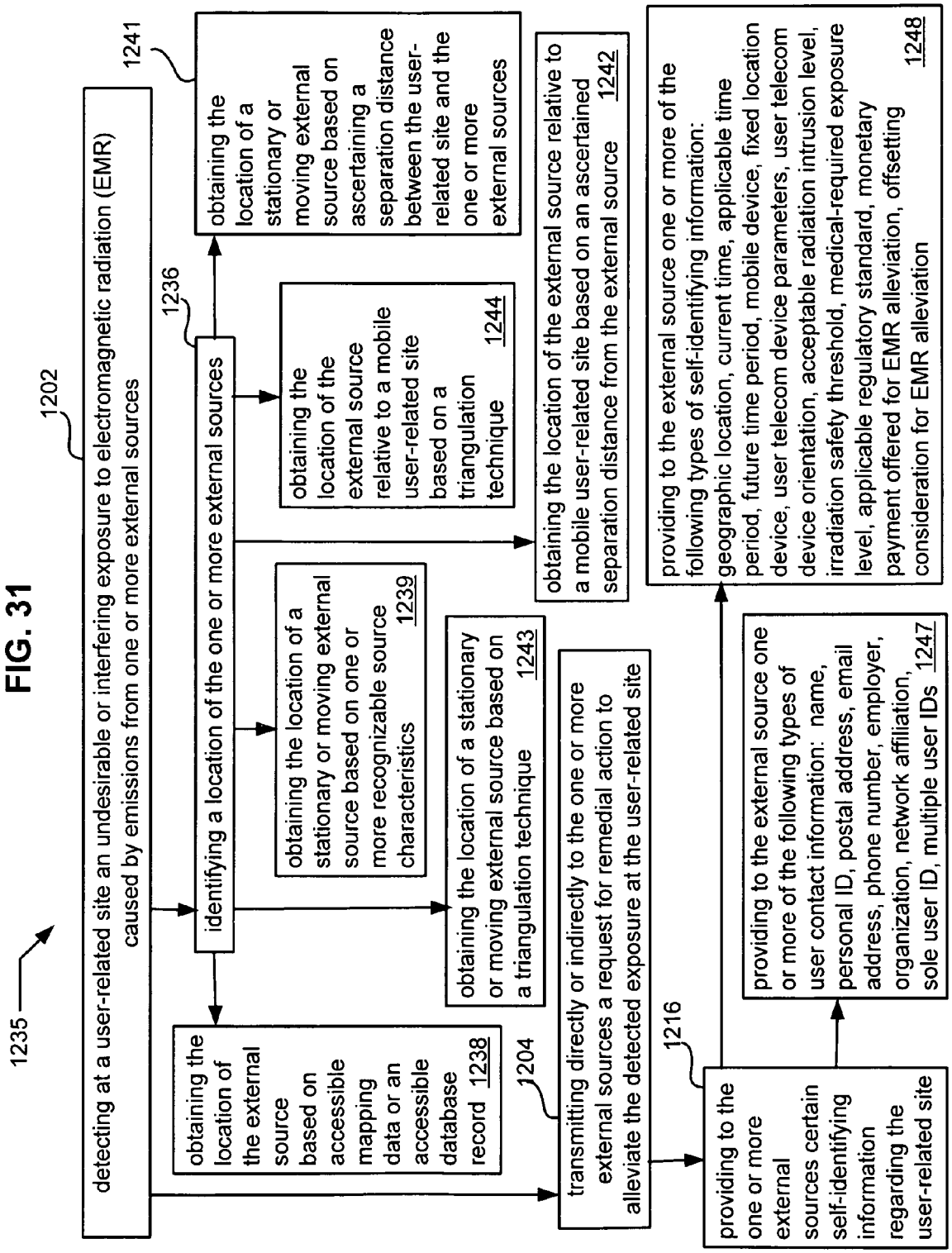

The embodiment features 1235 depicted in the detailed flow chart of FIG. 31 include previously described operations 1202, 1204, 1216 in combination with providing to the external source one or more of the following types of user contact information: name, personal ID, postal address, email address, phone number, employer, organization, network affiliation, sole user ID, multiple user IDs (block 1247). Other related exemplary operations may include providing to the external source one or more of the following types of self-identifying information: geographic location, current time, applicable time period, future time period, mobile device, fixed location device, user telecom device parameters, user telecom device orientation, acceptable radiation intrusion level, irradiation safety threshold, medical-required exposure level, applicable regulatory standard, monetary payment offered for EMR alleviation, offsetting consideration for EMR alleviation (block 1248).

Additional operational aspects may include identifying a location of the one or more external sources (block 1236). Related aspects may include obtaining the location of the external source based on accessible mapping data or an accessible database record (block 1238), and may further include obtaining the location of a stationary or moving external source based on one or more recognizable source characteristics (block 1239).

Some embodiments may further include obtaining the location of the external source relative to a mobile user-related site based on an ascertained separation distance from the external source (block 1242). A related aspect may include obtaining the location of a stationary or moving external source based on ascertaining a separation distance between the user-related site and the one or more external sources (block 1241). As another example, some process components may include obtaining the location of a stationary or moving external source based on a triangulation technique (block 1243). A related process component may include obtaining the location of the external source relative to a mobile user-related site based on a triangulation technique (block 1244).

Figure 32:
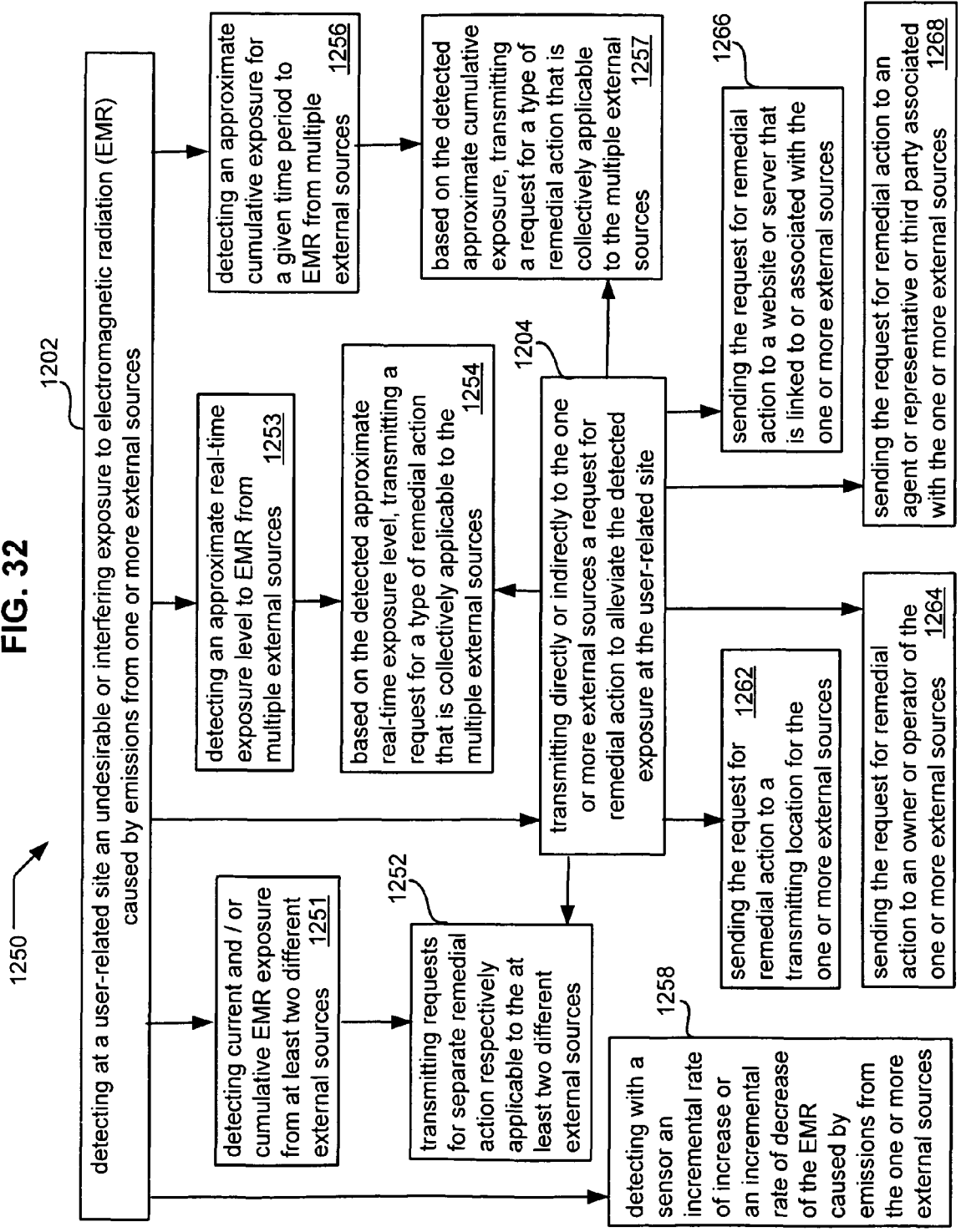

Referring to the illustrated embodiment features 1250 of FIG. 32, an exemplary process may include previously described operations 1202, 1204 along with detecting current and/or cumulative EMR exposure from at least two different external sources (block 1251). A related aspect may include transmitting requests for separate remedial action respectively applicable to the at least two different external sources (block 1252). Further aspects may include detecting an approximate real-time exposure level to EMR from multiple external sources (block 1253), and based on the detected approximate real-time exposure level, transmitting a request for a type of remedial action that is collectively applicable to the multiple external sources (block 1254).

Some process implementations may further include detecting an approximate cumulative exposure for a given time period to EMR from multiple external sources (block 1256), and based on the detected approximate cumulative exposure, transmitting a request for a type of remedial action that is collectively applicable to the multiple external sources (block 1257). Another possible process feature may include detecting with a sensor an incremental rate of increase or an incremental rate of decrease of the EMR caused by emissions from the one or more external sources (block 1258).

Additional aspects shown in FIG. 32 may include sending the request for remedial action to a transmitting location for the one or more external sources (block 1262), and in some instances sending the request for remedial action to an owner or operator of the one or more external sources (block 1263). Other further aspects may include sending the request for remedial action to a website or server that is linked to or associated with the one or more external sources (block 1266). Another exemplary aspect may include sending the request for remedial action to an agent or representative or third party associated with the one or more external sources (block 1268).

Figure 33:
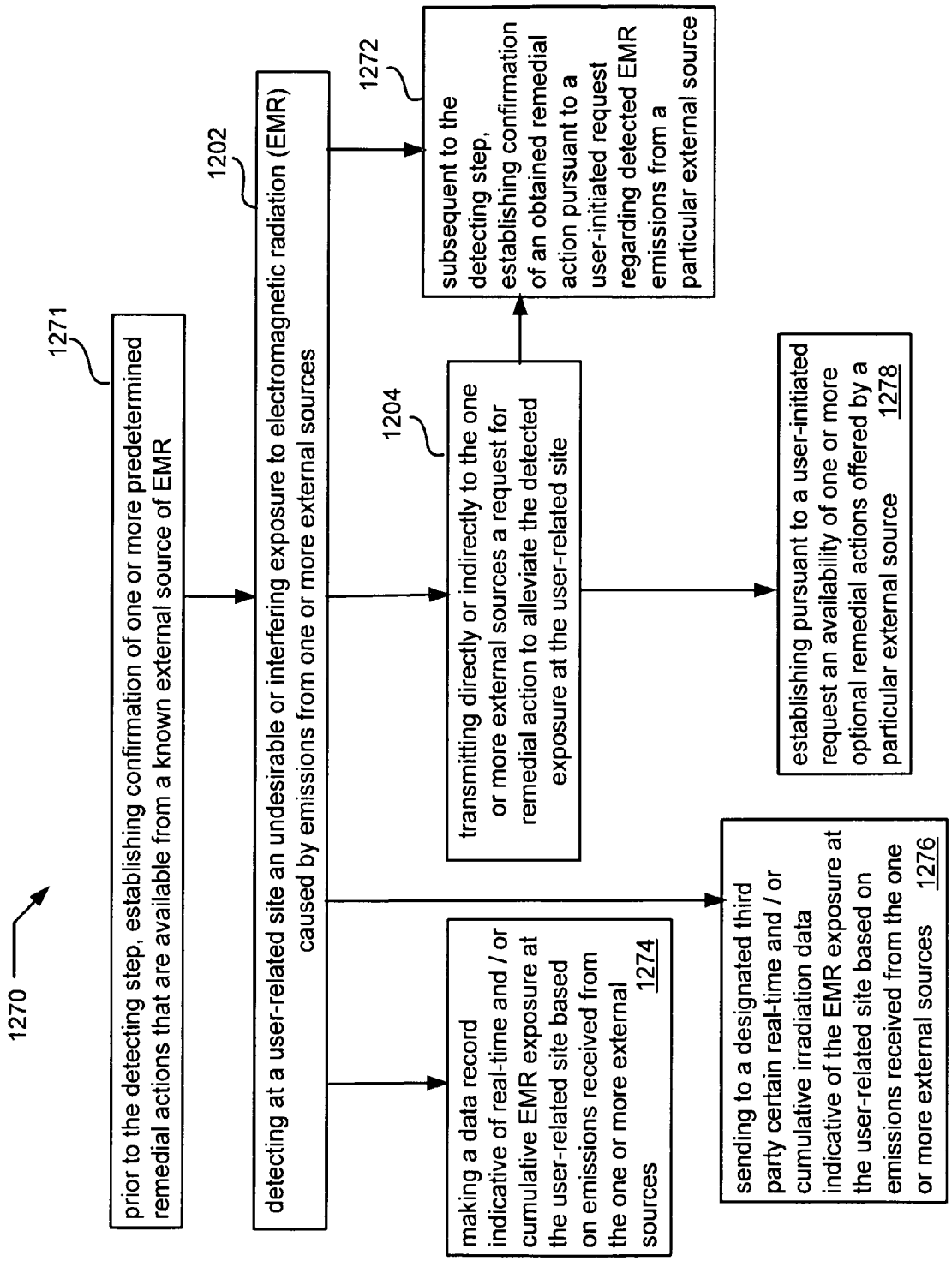

The detailed flow chart of FIG. 33 depicts exemplary embodiment aspects 1270 that include previously described process features 1202, 1204 in combination with making a data record indicative of real-time and/or cumulative EMR exposure at the user-related site based on emissions received from the one or more external sources (block 1274). Another process aspect may include sending to a designated third party certain real-time and/or cumulative irradiation data indicative of the EMR exposure at the user-related site based on emissions received from the one or more external sources (block 1276).

Other process features relating to possible remedial action responsive to irradiation exposure risks may include establishing pursuant to a user-initiated request an availability of one or more optional remedial actions offered by a particular external source (block 1278). In some instances a process feature may provide prior to the exposure detecting step, establishing confirmation of one or more predetermined remedial actions that are available from a known external source of EMR (block 1271). In some circumstances another process feature may provide subsequent to said detecting step, establishing confirmation of an obtained remedial action pursuant to a user-initiated request regarding detected EMR emissions from a particular external source (block 1272).

Figure 34:
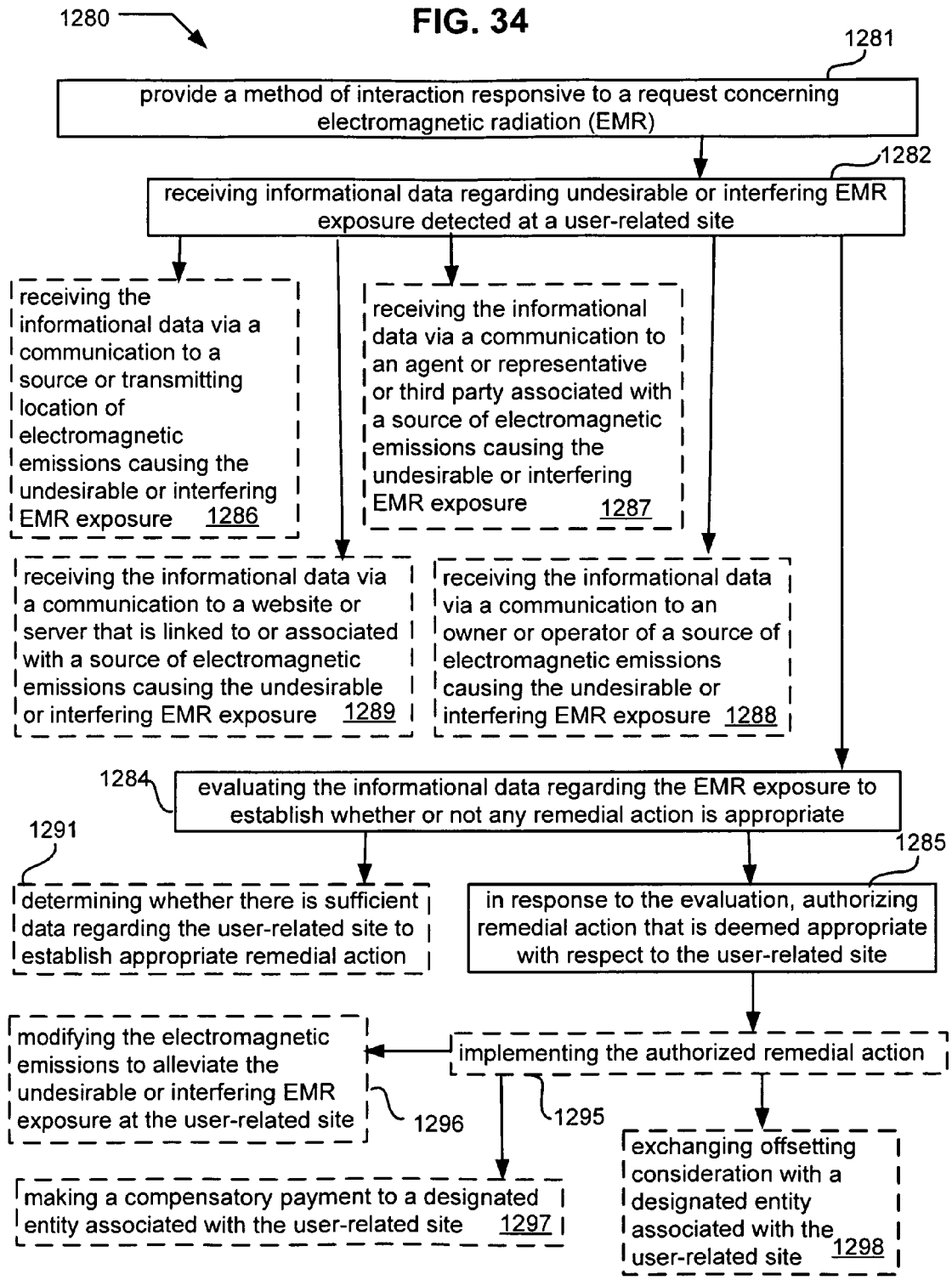
FIG. 34 is a high level flow chart illustrating other possible interactive techniques for irradiation protection.

Referring to the flow chart of FIG. 34, illustrated embodiment features 1280 may provide a method of interaction responsive to a request concerning electromagnetic radiation (EMR) (block 1281), wherein possible process features may include receiving informational data regarding undesirable or interfering EMR exposure detected at a user-related site (block 1282), and may further include evaluating the informational data regarding the EMR exposure to establish whether or not any remedial action is appropriate (block 1284). Another exemplary process aspect may provide in response to the evaluation, authorizing remedial action that is deemed appropriate with respect to the user-related site (block 1285).

Other possible process aspects may include receiving the informational data via a communication to a source or transmitting location of electromagnetic emissions causing the undesirable or interfering EMR exposure (block 1286). A further exemplary aspect may include receiving the informational data via a communication to a website or server that is linked to or associated with a source of electromagnetic emissions causing the undesirable or interfering EMR exposure (block 1289). In some instances another possible aspect may include receiving the informational data via a communication to an agent or representative or third party associated with a source of electromagnetic emissions causing the undesirable or interfering EMR exposure (block 1287).

Additional process features shown in FIG. 34 may include receiving the informational data via a communication to an owner or operator of a source of electromagnetic emissions causing the undesirable or interfering EMR exposure (block 1288). Another process aspect may include determining whether there is sufficient data regarding the user-related site to establish appropriate remedial action (block 1291). Another possible feature may include implementing the authorized remedial action (block 1295).

Some embodiments may include modifying the electromagnetic emissions to alleviate the undesirable or interfering EMR exposure at the user-related site (block 1296). A further aspect may include making a compensatory payment to a designated entity associated with the user-related site (block 1297). Another process aspect may include exchanging offsetting consideration with a designated entity associated with the user-related site (block 1298).

Figure 35:
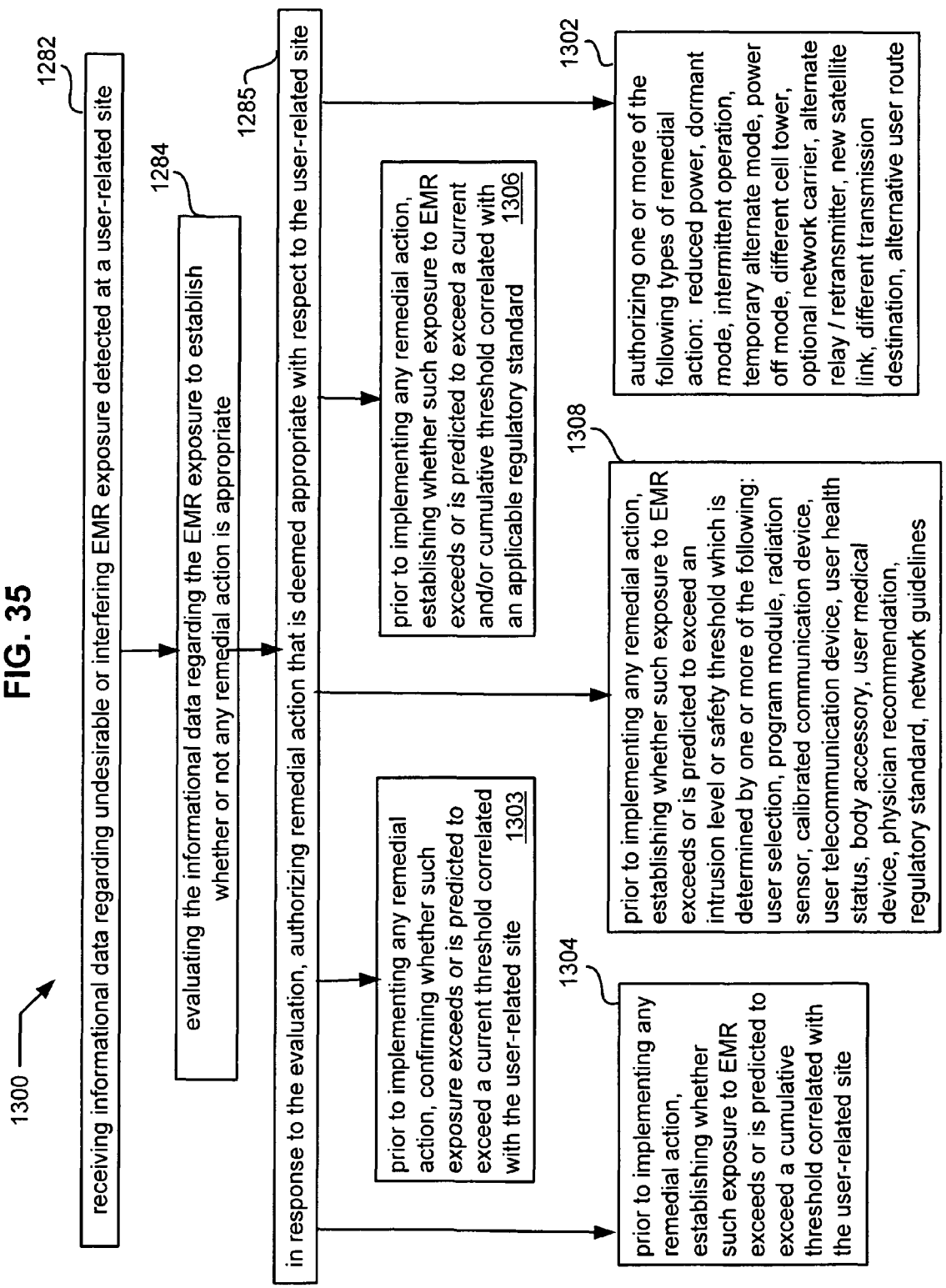
FIGS. 35-38 are detailed flow charts illustrating further possible irradiation protection techniques.

The exemplary process embodiment features 1300 depicted in FIG. 35 may include previously described aspects 1282, 1284, 1285 in combination with authorizing one or more of the following types of remedial action: reduced power, dormant mode, intermittent operation, temporary alternate mode, power off mode, different cell tower, optional network carrier, alternate relay/retransmitter, new satellite link, different transmission destination, alternative user route (block 1302). In some instances a possible process aspect may include prior to implementing any remedial action, confirming whether such exposure exceeds or is predicted to exceed a current threshold correlated with the user-related site (block 1303). A further possible process aspect may include prior to implementing any remedial action, establishing whether such exposure to EMR exceeds or is predicted to exceed a cumulative threshold correlated with the user-related site (block 1304).

Additional exemplary process operations may include prior to implementing any remedial action, establishing whether such exposure to EMR exceeds or is predicted to exceed a current and/or cumulative threshold correlated with an applicable regulatory standard (block 1306). Other possible process features may include prior to implementing any remedial action, establishing whether such exposure to EMR exceeds or is predicted to exceed an intrusion level or safety threshold which is determined by one or more of the following: user selection, program module, radiation sensor, calibrated communication device, user telecommunication device, user health status, body accessory, user medical device, physician recommendation, regulatory standard, network guidelines (block 1308).

Figure 36:
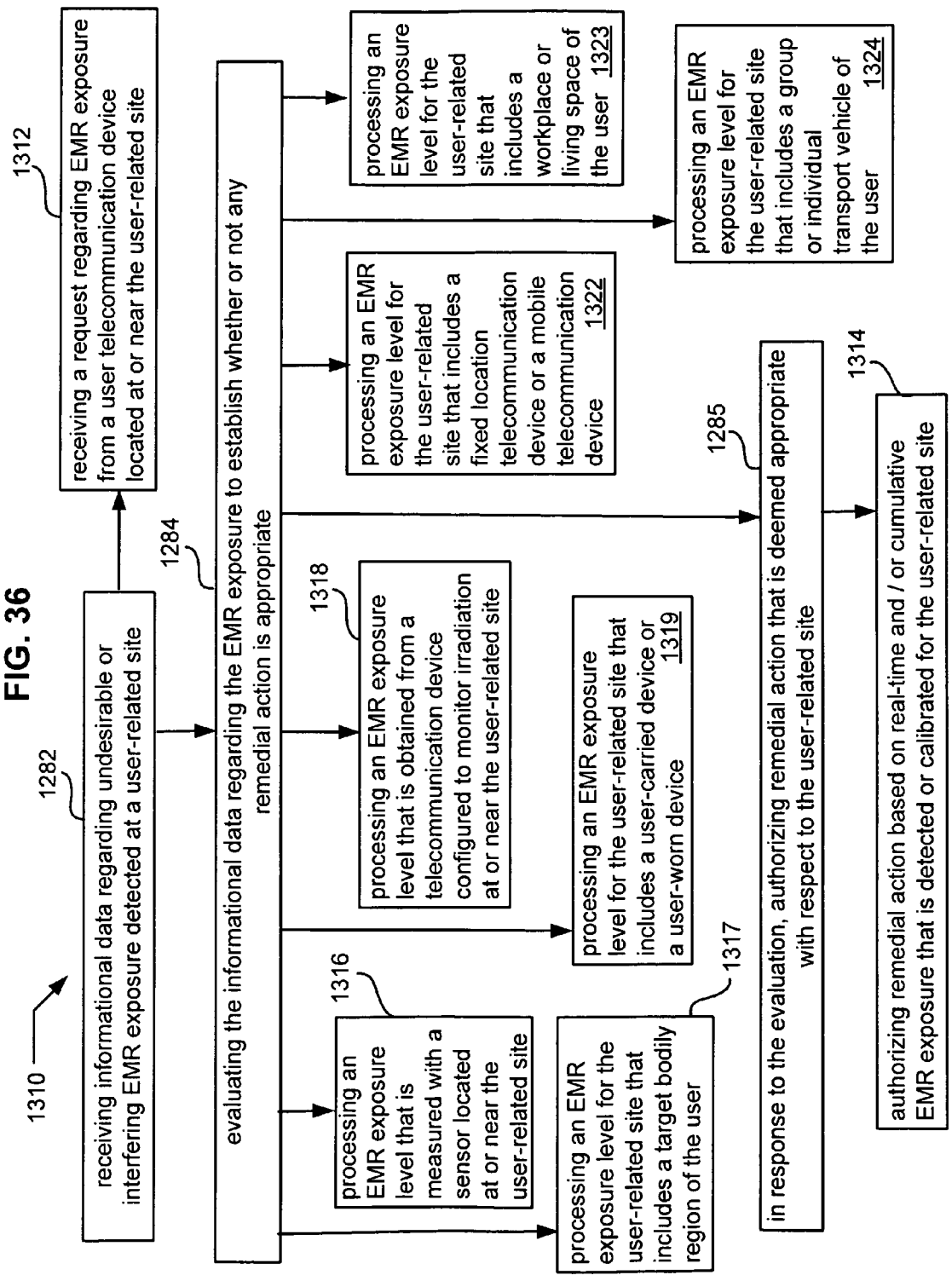

Referring to the flow chart of FIG. 36, various exemplary process embodiment features 1310 are depicted including previously described operations 1282, 1284, 1285 along with authorizing remedial action based on real-time and/or cumulative EMR exposure that is detected or calibrated for the user-related site (block 1314). Other possible operations may include processing an EMR exposure level that is measured with a sensor located at or near the user-related site (block 1316), and may further include processing an EMR exposure level for the user-related site that includes a target bodily region of the user (block 1317).

Another embodiment feature may include receiving a request regarding EMR exposure from a user telecommunication device located at or near the user-related site (block 1312). Another possible aspect may include processing an EMR exposure level that is obtained from a telecommunication device configured to monitor irradiation at or near the user-related site (block 1318). In some instances a further exemplary aspect may include processing an EMR exposure level for the user-related site that includes a user-carried device or a user-worn device (block 1319).

The flow chart of FIG. 36 illustrates additional possible features including processing an EMR exposure level for the user-related site that includes a fixed location telecommunication device or a mobile telecommunication device (block 1322). Other exemplary aspects may include processing an EMR exposure level for the user-related site that includes a workplace or living space of the user (block 1323), as well as processing an EMR exposure level for the user-related site that includes a group or individual transport vehicle of the user (block 1324).

Figure 37:
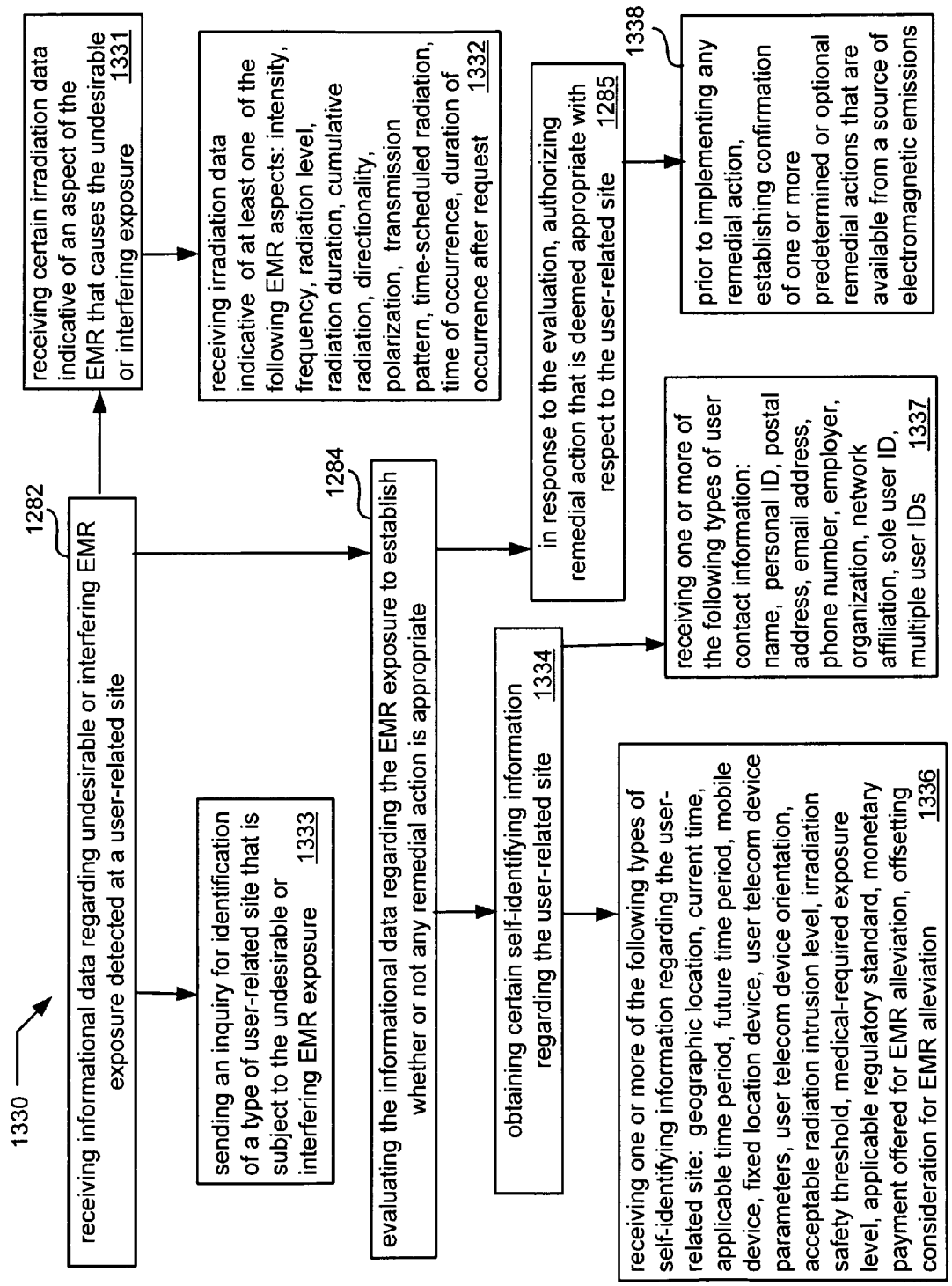

The detailed flow chart of FIG. 37 shows illustrated embodiment features 1330 that include previously described process operations 1282, 1284, 1285 as well as other possible features including receiving certain irradiation data indicative of an aspect of the EMR that causes the undesirable or interfering exposure (block 1331). A related process aspect may include receiving irradiation data indicative of at least one of the following EMR aspects: intensity, frequency, radiation level, radiation duration, cumulative radiation, directionality, polarization, transmission pattern, time-scheduled radiation, time of occurrence, duration of occurrence after request (block 1332).

Some process embodiments may include sending an inquiry for identification of a type of user-related site that is subject to the undesirable or interfering EMR exposure (block 1333). Further possible aspects may include obtaining certain self-identifying information regarding the user-related site (block 1334). In some instances exemplary operations may include receiving one or more of the following types of self-identifying information regarding the user-related site: geographic location, current time, applicable time period, future time period, mobile device, fixed location device, user telecom device parameters, user telecom device orientation, acceptable radiation intrusion level, irradiation safety threshold, medical-required exposure level, applicable regulatory standard, monetary payment offered for EMR alleviation, offsetting consideration for EMR alleviation (block 1336).

Further exemplary process features may include receiving one or more of the following types of user contact information: name, personal ID, postal address, email address, phone number, employer, organization, network affiliation, sole user ID, multiple user IDs (block 1337). Additional aspects may include prior to implementing any remedial action, establishing confirmation of one or more predetermined or optional remedial actions that are available from a source of electromagnetic emissions (block 1338).

Figure 38:
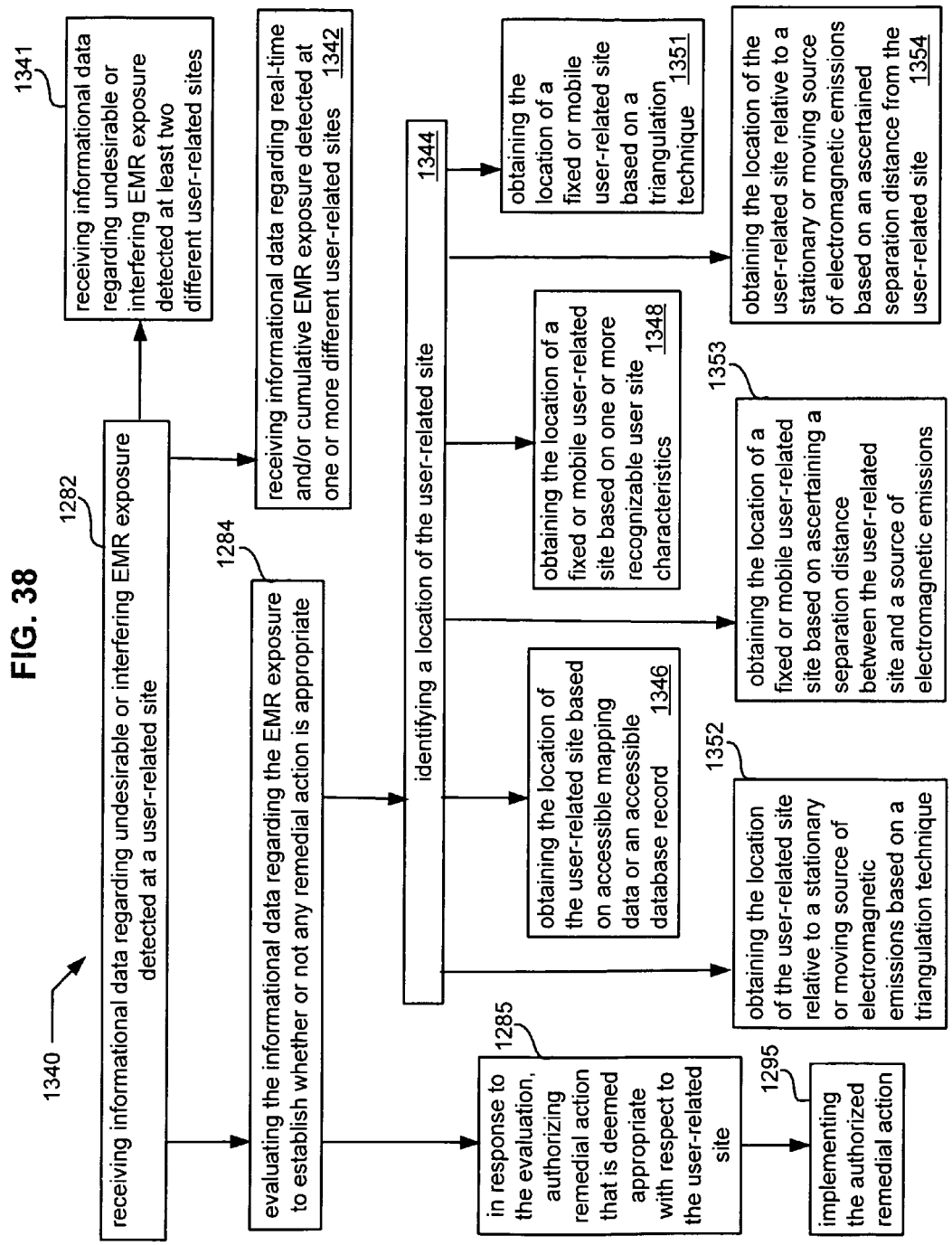

Referring to the detailed flow chart of FIG. 38, various possible embodiment features 1340 are illustrated including previously described aspects 1282, 1284, 1285, 1295 in combination with identifying a location of the user-related site (block 1344). Some exemplary aspects may include receiving informational data regarding undesirable or interfering EMR exposure detected at least two different user-related sites (block 1341). Other possible aspects may include receiving informational data regarding real-time and/or cumulative EMR exposure detected at one or more different user-related sites (block 1342).

Some process embodiments may include obtaining the location of the user-related site based on accessible mapping data or an accessible database record (block 1346). Additional process features may include obtaining the location of a fixed or mobile user-related site based on one or more recognizable user site characteristics (block 1348). Some exemplary aspects may include obtaining the location of a fixed or mobile user-related site based on a triangulation technique (block 1351). A related aspect may include obtaining the location of the user-related site relative to a stationary or moving source of electromagnetic emissions based on a triangulation technique (block 1352).

Also depicted in FIG. 38 are possible aspects that include obtaining the location of a fixed or mobile user-related site based on ascertaining a separation distance between the user-related site and a source of electromagnetic emissions (block 1353). Further possible aspects may include obtaining the location of the user-related site relative to a stationary or moving source of electromagnetic emissions based on an ascertained separation distance from the user-related site (block 1354).

Figure 39:
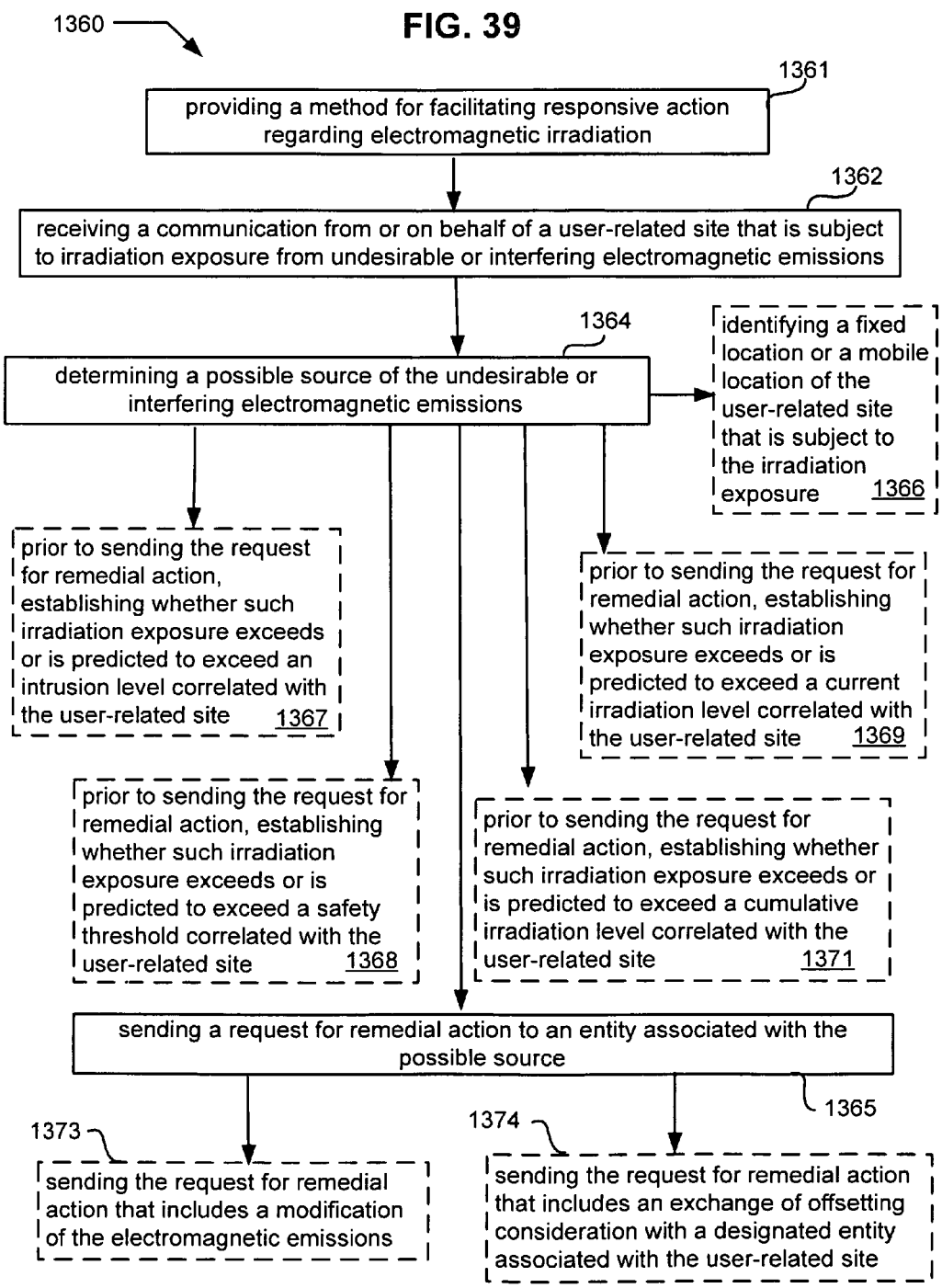
FIGS. 39-40 are flow charts illustrating additional examples of interactive techniques regarding irradiation protection.

Referring to FIG. 39, an illustrated process embodiment 1360 may provide a method for facilitating responsive action regarding electromagnetic irradiation (block 1361), including receiving a communication from or on behalf of a user-related site that is subject to irradiation exposure from undesirable or interfering electromagnetic emissions (block 1362), determining a possible source of the undesirable or interfering electromagnetic emissions (block 1364), and sending a request for remedial action to an entity associated with the possible source (block 1365). Another possible process aspect may include identifying a fixed location or a mobile location of the user-related site that is subject to the irradiation exposure (block 1366).

Additional process features may include prior to sending the request for remedial action, establishing whether such irradiation exposure exceeds or is predicted to exceed an intrusion level correlated with the user-related site (block 1367), or whether such irradiation exposure exceeds or is predicted to exceed a safety threshold correlated with the user-related site (block 1368). Further possible process features may include prior to sending the request for remedial action, establishing whether such irradiation exposure exceeds or is predicted to exceed a current irradiation level correlated with the user-related site (block 1369), or whether such irradiation exposure exceeds or is predicted to exceed a cumulative irradiation level correlated with the user-related site (block 1371).

In some instances an exemplary aspect may include sending the request for remedial action that includes a modification of the electromagnetic emissions (block 1373). Another exemplary aspect may include sending the request for remedial action that includes an exchange of offsetting consideration with a designated entity associated with the user-related site (block 1374).

Figure 40:
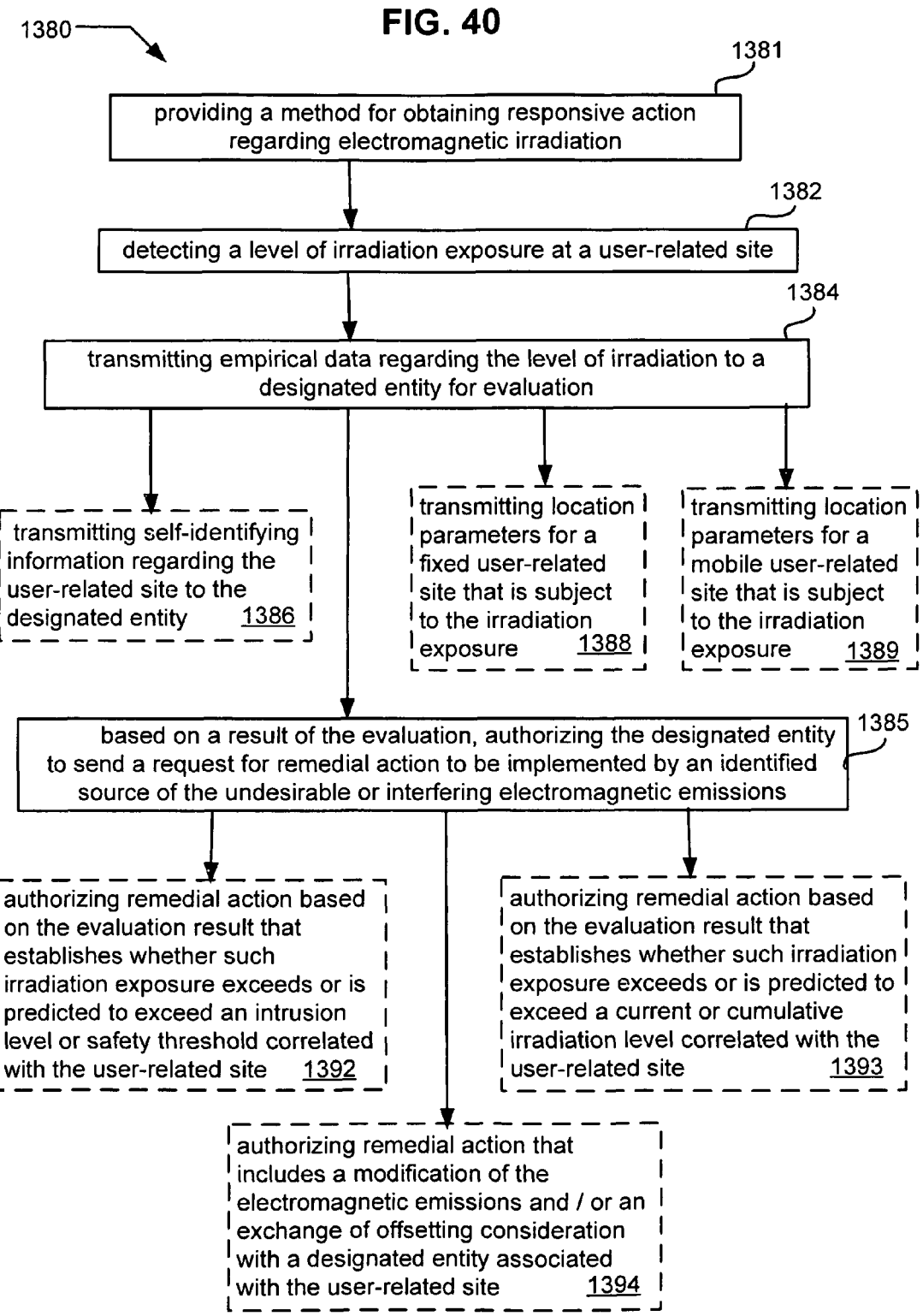
Figure 41:
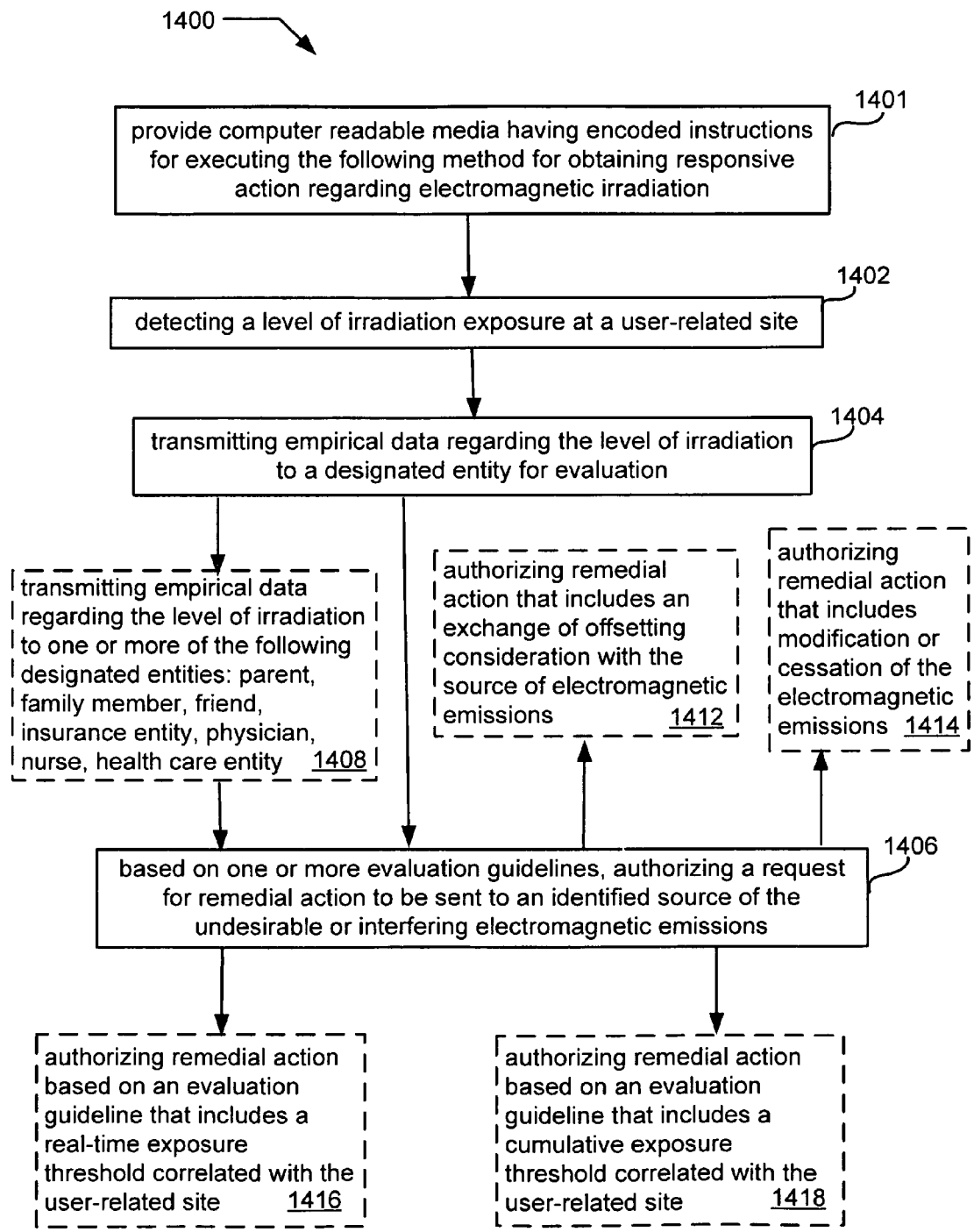
FIGS. 41-44 are diagrammatic flow charts illustrating other possible computer program product features.

The illustrated embodiment features 1380 of FIG. 40 depict a possible process for obtaining responsive action regarding electromagnetic irradiation (block 1381), including detecting a level of irradiation exposure at a user-related site (block 1382), and transmitting empirical data regarding the level of irradiation to a designated entity for evaluation (block 1384). Another possible aspect may provide based on a result of the evaluation, authorizing the designated entity to send a request for remedial action to be implemented by an identified source of the undesirable or interfering electromagnetic emissions (block 1385).

Additional process aspects may include transmitting self-identifying information regarding the user-related site to the designated entity (block 1386). Further exemplary aspects may include transmitting location parameters for a fixed user-related site that is subject to the irradiation exposure (block 1388), and in some instances transmitting location parameters for a mobile user-related site that is subject to the irradiation exposure (block 1389).

Other possible features may include authorizing remedial action based on the evaluation result that establishes whether such irradiation exposure exceeds or is predicted to exceed an intrusion level or safety threshold correlated with the user-related site (block 1392). In some instances a possible aspect may include authorizing remedial action based on the evaluation result that establishes whether such irradiation exposure exceeds or is predicted to exceed a current or cumulative irradiation level correlated with the user-related site (block 1393). A further aspect may include authorizing remedial action that includes a modification of the electromagnetic emissions and/or an exchange of offsetting consideration with a designated entity associated with the user-related site (block 1394).

The illustrated embodiments of FIGS. 41-44 depict exemplary aspects of computer program products that incorporate executable instructions in computer readable media. For example, the diagrammatic flow chart features 1400 shown in FIG. 41 may be incorporated in an article of manufacture which provides computer readable media having encoded instructions for executing a method of obtaining responsive action regarding electromagnetic irradiation (block 1401), wherein the method may include detecting a level of irradiation exposure at a user-related site (block 1402), and transmitting empirical data regarding the level of irradiation to a designated entity for evaluation (block 1404). Other method features may provide based on one or more evaluation guidelines, authorizing a request for remedial action to be sent to an identified source of the undesirable or interfering electromagnetic emissions (block 1406).

Some embodiments may further provide encoded instructions for transmitting empirical data regarding the level of irradiation to one or more of the following designated entities: parent, family member, friend, insurance entity, physician, nurse, health care entity (block 1408). Additional possible aspects may include encoded instructions for authorizing remedial action that an exchange of offsetting consideration with the source of electromagnetic emissions (block 1412).

Other possible method aspects may provide encoded instructions for authorizing remedial action based on an evaluation guideline that includes a real-time exposure threshold correlated with the user-related site (block 1416), or in some instances wherein the evaluation guideline includes a cumulative exposure threshold correlated with the user-related site (block 1418). Additional method aspects may provide encoded instructions for authorizing remedial action that includes a modification or cessation of the electromagnetic emissions (block 1414).

Figure 42:
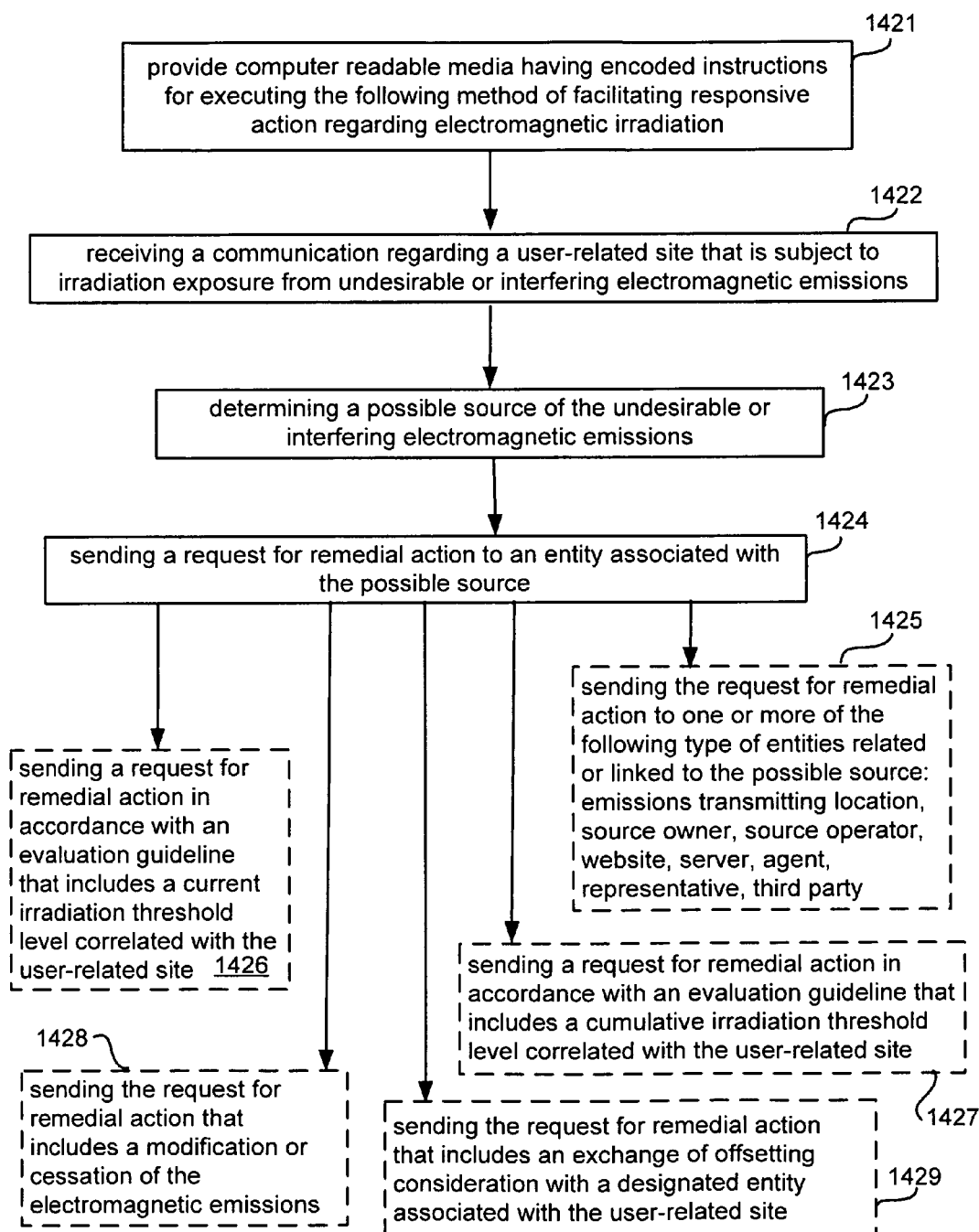

As a further example, the diagrammatic flow chart features 1420 shown in FIG. 42 may be incorporated in an article of manufacture which provides computer readable media having encoded instructions for executing a method of facilitating responsive action regarding electromagnetic irradiation (block 1421), wherein the method includes receiving a communication regarding a user-related site that is subject to irradiation exposure from undesirable or interfering electromagnetic emissions (block 1422), and determining a possible source of the undesirable or interfering electromagnetic emissions (block 1423). Other method features may include sending a request for remedial action to an entity associated with the possible source (block 1424).

Additional aspects may include encoded instructions for sending the request for remedial action to one or more of the following type of entities related or linked to the possible source: emissions transmitting location, source owner, source operator, website, server, agent, representative, third party (block 1425). Further method aspects may include sending the request for remedial action that includes a modification or cessation of the electromagnetic emissions (block 1428). Another possible method access may include sending the request for remedial action that includes an exchange of off-setting consideration with a designated entity associated with the user-related site (block 1429).

Further possible aspects may include encoded instructions for sending a request for remedial action in accordance with an evaluation guideline that includes a real-time exposure threshold correlated with the user-related site (block 1426). Additional exemplary aspects may include sending a request for remedial action in accordance with an evaluation guideline that includes a cumulative exposure threshold correlated with the user-related site (block 1427).

Figure 43:
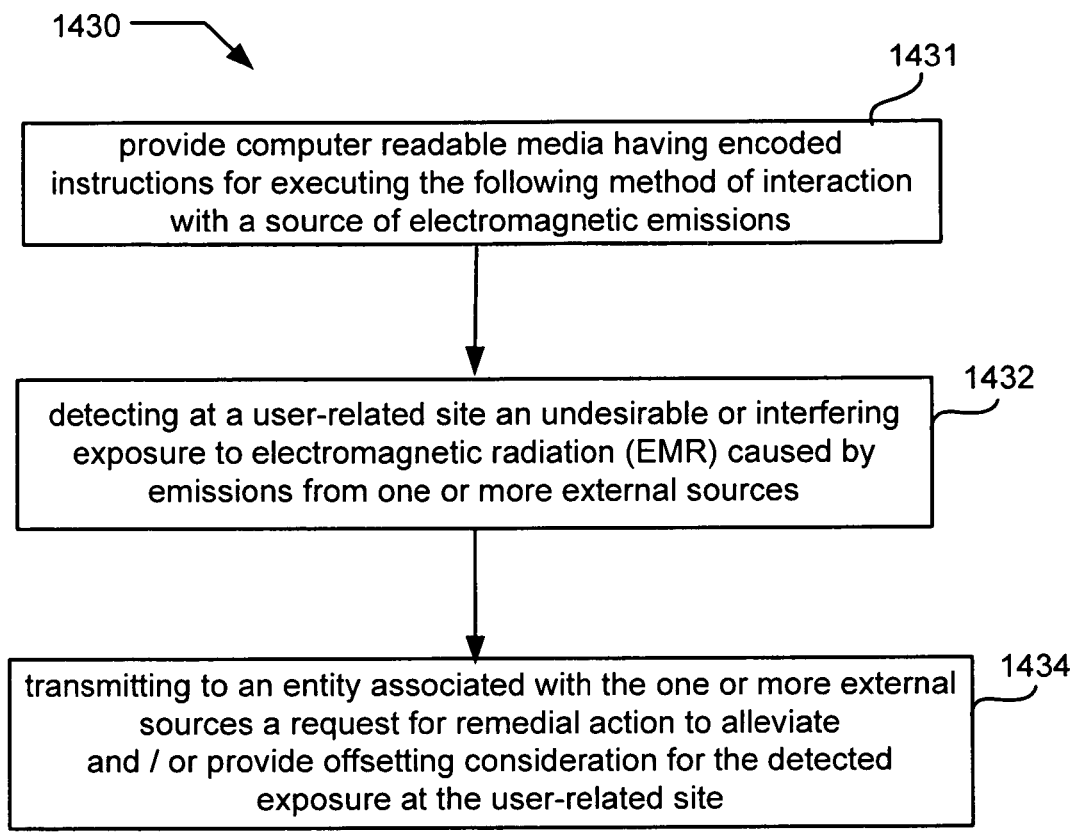

As another example, the diagrammatic flow chart features 1430 shown in FIG. 43 may be incorporated in an article of manufacture which provides computer readable media having encoded instructions for executing a method of interaction with a source of electromagnetic emissions (block 1431), wherein the method includes detecting at a user-related site an undesirable or interfering exposure to electromagnetic radiation (EMR) caused by emissions from one or more external sources (block 1432). A further possible method aspect may include transmitting to an entity associated with the one or more external sources a request for remedial action to alleviate the detected exposure at the user-related site (block 1434).

Figure 44:
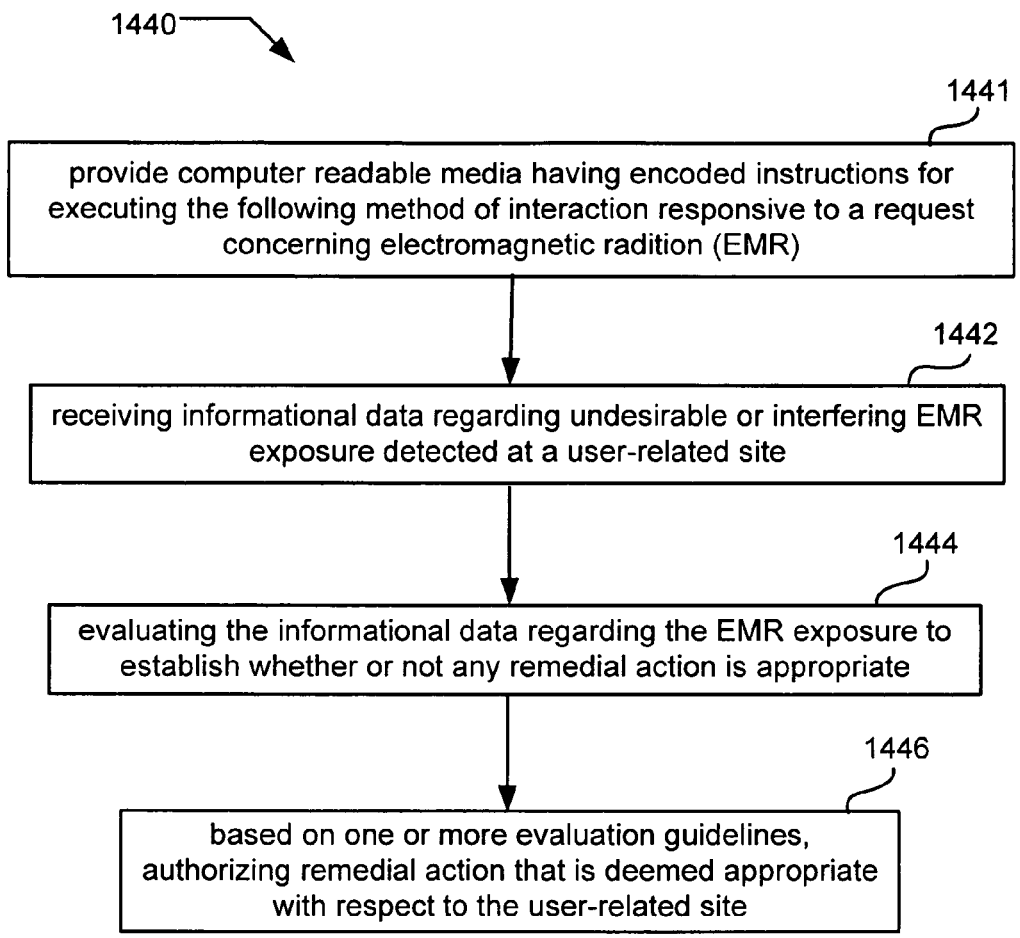

As an additional example, the diagrammatic flow chart features 1440 shown in FIG. 44 may be incorporated in an article of manufacture which provides computer readable media having encoded instructions for executing a method of interaction responsive to a request concerning electromagnetic radiation (EMR) (block 1442), wherein the method includes receiving informational data regarding undesirable or interfering EMR exposure detected at a user-related site (block 1442), and evaluating the informational data regarding the EMR exposure to establish whether or not any remedial action is appropriate (block 1444). Another possible method aspect may include based on one or more evaluation guidelines, authorizing remedial action that is deemed appropriate with respect to the user-related site (block 1446).

It will be understood by those skilled in the art that the various components and elements disclosed in the system and schematic diagrams herein as well as the various steps and sub-steps disclosed in the flow charts herein may be incorporated together in different claimed combinations in order to enhance possible benefits and advantages.

The exemplary system, apparatus, and computer program product embodiments disclosed herein including FIGS. 1-4, FIGS. 13-14, FIGS. 23-28 and FIGS. 41-44 along with other components, devices, know-how, skill and techniques known in the art have the capability of implementing and practicing the methods and processes that are depicted in FIGS. 5-12, FIGS. 15-22 and FIGS. 29-40. However it is to be further understood by those skilled in the art that other systems, apparatus and technology may be used to implement and practice such methods and processes.

Exemplary methods, systems and components disclosed herein enable detection and/or monitoring and/or control of electromagnetic radiation (EMR) exposure of target body-related portions of a user operating a telecommunication device. It is understood that some embodiments may include a risk-assessment output that is provided based on a safety threshold or predetermined intrusion level of EMR exposure. A further aspect may include interaction with external EMR sources regarding possible modification of emissions as well as possible arrangements for other types of remedial action.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of interaction with a source of electromagnetic emissions, comprising:
   detecting at a user-related site an undesirable or interfering exposure to electromagnetic radiation (EMR) caused by emissions from one or more external sources; and
   transmitting directly or indirectly to the one or more external sources a request for remedial action to alleviate the detected exposure at the user-related site.

2. The method of claim 1 further comprising:
   prior to said transmitting, establishing whether such exposure to EMR exceeds or is predicted to exceed a current and/or cumulative threshold correlated with the user-related site.

3. The method of claim 1 further comprising:
   prior to said transmitting, establishing whether such exposure to EMR exceeds or is predicted to exceed an intrusion level or safety threshold which is determined by one or more of the following: user selection, program module, radiation sensor, calibrated communication device, user telecommunication device, user health status, body accessory, user medical device, physician recommendation, regulatory standard, network guidelines.

4. The method of claim 1 further comprising:
   prior to said transmitting, establishing whether such exposure to EMR exceeds or is predicted to exceed a current and/or cumulative threshold correlated with an applicable regulatory standard.

5. The method of claim 1 wherein said detecting at the user-related site includes:
   measuring a level of EMR exposure with a sensor located at or near the user-related site.

6. The method of claim 1 wherein said detecting at the user-related site includes:
   measuring a level of EMR exposure with a telecommunication device configured to monitor irradiation at or near the user-related site.

7. The method of claim 1 wherein said detecting at the user-related site includes:
   detecting the undesirable or interfering exposure at the user-related site that includes a target bodily region of the user.

8. The method of claim 1 wherein said detecting at the user-related site includes:

detecting the undesirable or interfering exposure at the user-related site that includes a user-carried device or a user-worn device.

9. The method of claim 1 wherein said detecting at the user-related site includes:
   detecting the undesirable or interfering exposure at a user's fixed location telecommunication device or at a user's mobile telecommunication device.

10. The method of claim 1 wherein said detecting at the user-related site includes:
    detecting the undesirable or interfering exposure at the user-related site that includes a workplace or living space of the user.

11. The method of claim 1 wherein said detecting at the user-related site includes:
    detecting the undesirable or interfering exposure at the user-related site that includes a group or individual transport vehicle of the user.

12. The method of claim 1 wherein said transmitting the request for remedial action includes:
    transmitting the request for one or more of the following types of remedial action: reduced power, dormant mode, intermittent operation, temporary alternate mode, power off mode, different cell tower, optional network carrier, alternate relay/retransmitter, new satellite link, different transmission destination, alternative user route.

13. The method of claim 1 wherein said transmitting the request for remedial action includes:
    transmitting the request from a user telecommunication device located at or near the user-related site.

14. The method of claim 1 further comprising:
    providing to the one or more external sources certain irradiation data indicative of an aspect of the EMR that causes the undesirable or interfering exposure.

15. The method of claim 14 wherein said providing certain irradiation data indicative of the aspect of the EMR includes:
    providing to the external source one or more of the following EMR aspects: intensity, frequency, radiation level, radiation duration, cumulative radiation, directionality, polarization, transmission pattern, time-scheduled radiation, time of occurrence, duration of occurrence after request.

16. The method of claim 1 further comprising:
    providing to the one or more external sources certain self-identifying information regarding the user-related site.

17. The method of claim 16 wherein said providing certain self-identifying information regarding the user-related site includes:
    providing to the external source one or more of the following types of self-identifying information: geographic location, current time, applicable time period, future time period, mobile device, fixed location device, user telecom device parameters, user telecom device orientation, acceptable radiation intrusion level, irradiation safety threshold, medical-required exposure level, applicable regulatory standard, monetary payment offered for EMR alleviation, offsetting consideration for EMR alleviation.

18. The method of claim 16 wherein said providing certain self-identifying information regarding the user-related site includes:
    providing to the external source one or more of the following types of user contact information: name, personal ID, postal address, email address, phone number, employer, organization, network affiliation, sole user ID, multiple user IDs.

19. The method of claim 1 further comprising:
    identifying a location of the one or more external sources.

20. The method of claim 19 wherein said identifying the location of the one or more external sources includes:
    obtaining the location of the external source based on accessible mapping data or an accessible database record.

21. The method of claim 19 wherein said identifying the location of the one or more external sources includes:
    obtaining the location of a stationary or moving external source based on one or more recognizable source characteristics.

22. The method of claim 19 wherein said identifying the location of the one or more external sources includes:
    obtaining the location of a stationary or moving external source based on a triangulation technique.

23. The method of claim 19 wherein said obtaining the location one or more external sources includes:
    obtaining the location of the external source relative to a mobile user-related site based on a triangulation technique.

24. The method of claim 19 wherein said identifying the location of the one or more external sources includes:
    obtaining the location of a stationary or moving external source based on ascertaining a separation distance between the user-related site and the one or more external sources.

25. The method of claim 19 wherein said obtaining the location of one or more external sources includes:
    obtaining the location of the external source relative to a mobile user-related site based on an ascertained separation distance from the external source.

26. The method of claim 1 further comprising:
    identifying a type of external source by one or more of the following detection techniques: frequency characteristics, waveform characteristics, band pass filter, high pass filter, low pass filter, ID tags on source beams, directionality of incident radiation emissions, fixed intensity emission, variable intensity emission, constant emission, intermittent emission, message inquiry, broadcast query.

27. The method of claim 1 wherein said detecting at the user-related site includes:
    detecting with a sensor an incremental rate of increase or an incremental rate of decrease of the EMR caused by emissions from the one or more external sources.

28. The method of claim 1 wherein said detecting at the user-related site includes:
    detecting current and/or cumulative EMR exposure from at least two different external sources.

29. The method of claim 28 wherein said transmitting directly or indirectly includes:
    transmitting requests for separate remedial action respectively applicable to the at least two different external sources.

30. The method of claim 1 wherein said detecting at the user-related site includes:
    detecting an approximate real-time exposure level to EMR from multiple external sources; and
    based on the detected approximate real-time exposure level, transmitting a request for a type of remedial action that is collectively applicable to the multiple external sources.

31. The method of claim 1 wherein said detecting at the user-related site includes:
    detecting an approximate cumulative exposure for a given time period to EMR from multiple external sources; and based on the detected approximate cumulative exposure, transmitting a request for a type of remedial action that is collectively applicable to the multiple external sources.

32. The method of claim 1 further comprising:
making a data record indicative of real-time and/or cumulative EMR exposure at the user-related site based on emissions received from the one or more external sources.

33. The method of claim 1 further comprising:
sending to a designated third party certain real-time and/or cumulative irradiation data indicative of the EMR exposure at the user-related site based on emissions received from the one or more external sources.

34. The method of claim 1 wherein said transmitting directly or indirectly includes:
sending the request for remedial action to a transmitting location for the one or more external sources.

35. The method of claim 1 wherein said transmitting directly or indirectly includes:
sending the request for remedial action to an owner or operator of the one or more external sources.

36. The method of claim 1 wherein said transmitting directly or indirectly includes:
sending the request for remedial action to an agent or representative or third party associated with the one or more external sources.

37. The method of claim 1 wherein said transmitting directly or indirectly includes:
sending the request for remedial action to a website or server that is linked to or associated with the one or more external sources.

38. The method of claim 1 further including:
prior to said detecting step, establishing confirmation of one or more predetermined remedial actions that are available from a known external source of EMR.

39. The method of claim 1 further including:
subsequent to said detecting step, establishing confirmation of an obtained remedial action pursuant to a user-initiated request regarding detected EMR emissions from a particular external source.

40. The method of claim 1 further including:
establishing pursuant to a user-initiated request an availability of one or more optional remedial actions offered by a particular external source.

41. A method for obtaining responsive action regarding electromagnetic irradiation, comprising:
detecting a level of irradiation exposure at a user-related site;
transmitting empirical data regarding the level of irradiation to a designated entity for evaluation; and
based on a result of the evaluation, authorizing the designated entity to send a request for remedial action to be implemented by an identified source of the undesirable or interfering electromagnetic emissions.

42. The method of claim 41 further comprising:
transmitting self-identifying information regarding the user-related site to the designated entity.

43. The method of claim 41 further comprising:
transmitting location parameters for a fixed user-related site that is subject to the irradiation exposure.

44. The method of claim 41 further comprising:
transmitting location parameters for a mobile user-related site that is subject to the irradiation exposure.

45. The method of claim 41 said authorizing the sending of the request for remedial action includes:
authorizing remedial action based on the evaluation result that establishes whether such irradiation exposure exceeds or is predicted to exceed an intrusion level or safety threshold correlated with the user-related site.

46. The method of claim 41 said authorizing the sending of the request for remedial action includes:
authorizing remedial action based on the evaluation result that establishes whether such irradiation exposure exceeds or is predicted to exceed a current or cumulative irradiation level correlated with the user-related site.

47. The method of claim 41 wherein said authorizing the sending of the request for remedial action includes:
authorizing remedial action that includes a modification of the electromagnetic emissions and/or an exchange of offsetting consideration with a designated entity associated with the user-related site.

48. A non-transitory computer readable storage medium having encoded instructions for executing a method of obtaining responsive action regarding electromagnetic irradiation, wherein the method includes
detecting a level of irradiation exposure at a user-related site;
transmitting empirical data regarding the level of irradiation to a designated entity for evaluation; and
based on one or more evaluation guidelines, authorizing a request for remedial action to be sent to an identified source of the undesirable or interfering electromagnetic emissions.

49. The non-transitory computer readable storage medium of claim 48 wherein the method further includes:
transmitting self-identifying information regarding the user-related site to the designated entity.

50. The non-transitory computer readable storage medium of claim 48 wherein the method further includes:
transmitting location parameters for a fixed user-related site that is subject to the irradiation exposure.

51. The non-transitory computer readable storage medium of claim 48 wherein the method further includes:
transmitting location parameters for a mobile user-related site that is subject to the irradiation exposure.

52. The non-transitory computer readable storage medium of claim 48 wherein the method feature transmitting empirical data regarding the level of irradiation includes:
transmitting empirical data regarding the level of irradiation to one or more of the following designated entities: parent, family member, friend, insurance entity, physician, nurse, health care entity.

53. The non-transitory computer readable storage medium of claim 48 wherein the method feature authorizing the sending of the request for remedial action includes:
authorizing remedial action based on at least one evaluation guideline that establishes whether such irradiation exposure exceeds or is predicted to exceed an intrusion level or safety threshold correlated with the user-related site.

54. The non-transitory computer readable storage medium of claim 48 wherein the method feature authorizing the sending of the request for remedial action includes:
authorizing remedial action based on at least one evaluation guideline that establishes whether such irradiation exposure exceeds or is predicted to exceed a current or cumulative irradiation level correlated with the user-related site.

55. The non-transitory computer readable storage medium of claim 48 wherein the method feature authorizing the sending of the request for remedial action includes:

authorizing remedial action that includes a modification or cessation of the electromagnetic emissions and/or an exchange of offsetting consideration with the source of electromagnetic emissions.

56. The non-transitory computer readable storage medium of claim 48 wherein the method feature authorizing the sending of the request for remedial action includes:

authorizing remedial action based on an evaluation guideline that includes a current exposure threshold correlated with the user-related site.

57. The non-transitory computer readable storage medium of claim 48 wherein the method feature authorizing the sending of the request for remedial action includes:

authorizing remedial action based on an evaluation guideline that includes a cumulative irradiation threshold correlated with the user-related site.

58. A system for obtaining responsive action regarding electromagnetic irradiation, comprising:

sensor means for detecting at a user-related site an undesirable or interfering exposure to electromagnetic radiation (EMR) caused by emissions from one or more external sources; and a communication module operably coupled to the sensor means, wherein the communication module is configured for transmitting directly or indirectly to the one or more external sources a request for remedial action to alleviate or otherwise compensate for the detected exposure at the user-related site.

* * * * *